United States Patent [19]

Smith et al.

[11] Patent Number: 5,047,044
[45] Date of Patent: Sep. 10, 1991

[54] MEDICAL DROPLET WHOLE BLOOD AND LIKE MONITORING

[75] Inventors: Roger E. Smith, Bountiful; Mark E. Astill, Centerville; Jay L. Smith, Ogden; Gale H. Thorne, Bountiful, all of Utah

[73] Assignee: Thorne, Smith, Astill Technologies, Inc., Ogden, Utah

[21] Appl. No.: 484,154

[22] Filed: Feb. 23, 1990

Related U.S. Application Data

[62] Division of Ser. No. 256,678, Oct. 12, 1988.

[51] Int. Cl.⁵ .............................................. A61B 17/32
[52] U.S. Cl. ................................................. 606/182
[58] Field of Search ...................... 128/760, 762, 771; 606/181–183; 204/206; 206/569–571

[56] References Cited

U.S. PATENT DOCUMENTS

| | | | |
|---|---|---|---|
| 3,030,959 | 4/1962 | Grunest | 606/182 |
| 3,358,689 | 12/1967 | Higgins | 606/181 |
| 4,203,446 | 5/1980 | Hofert et al. | 606/182 |
| 4,379,456 | 4/1983 | Cornell et al. | 606/182 |
| 4,653,513 | 3/1987 | Dombrowski | 606/182 |
| 4,817,603 | 4/1989 | Turner et al. | 606/182 |

Primary Examiner—Max Hindenburg
Attorney, Agent, or Firm—K. S. Cornaby

[57] ABSTRACT

An assay employing a tracer comprising a ligand having a mercury label wherein mercury label is released from at least one of a bound or free tracer phase and interacts with a metal. Analyte is determined by a change in at least one property of the metal caused by such interaction. The invention also relates to a device for such an assay wherein mercury ions released from a free or bound tracer are caused to eventually amalgamate with a metal, and the presence and/or amount of analyte is determined by changes in the metal resulting from the eventual amalgamation which may be measured electrically or by other means. The invention also relates to novel assay instruments, novel lancets, assay sensors, assay sensor packets, instrumentation and combinations of assay components, and related methods.

18 Claims, 20 Drawing Sheets

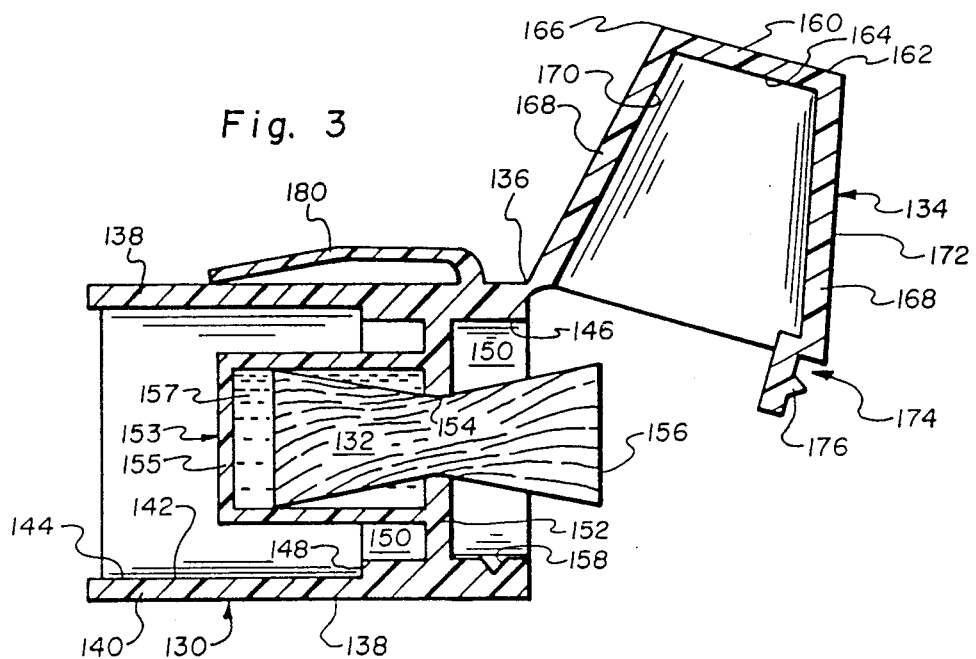
Fig. 3
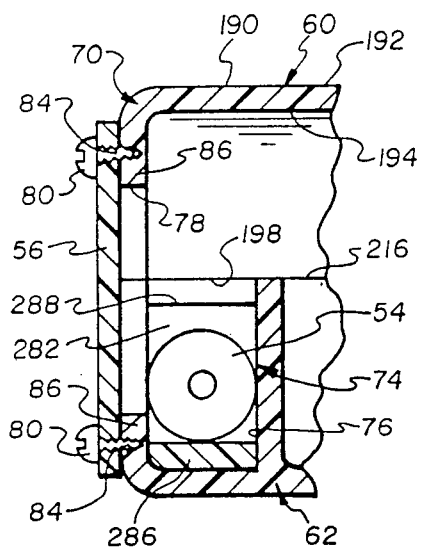
Fig. 4
Fig. 15
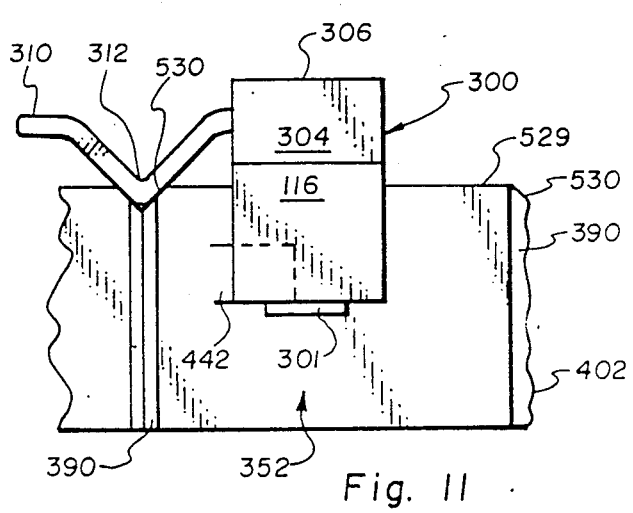
Fig. 11

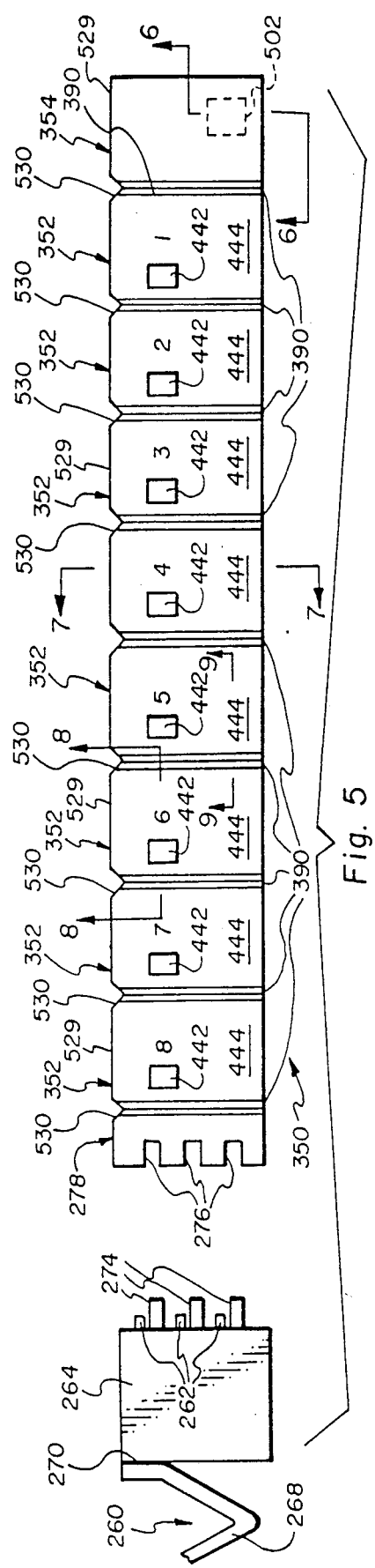
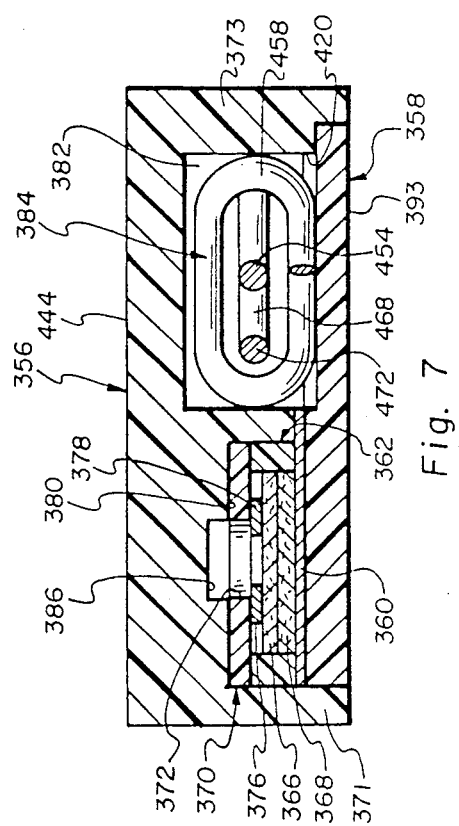
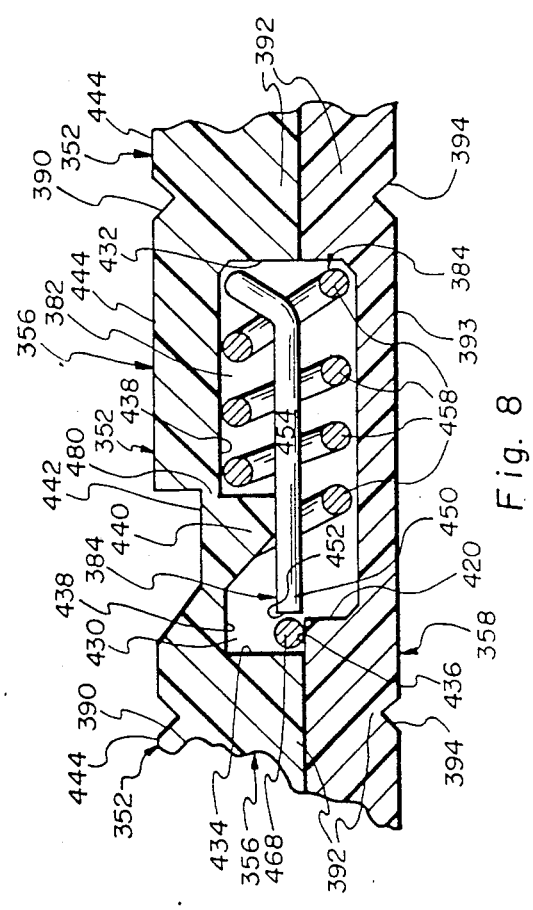
Fig. 5
Fig. 7
Fig. 8

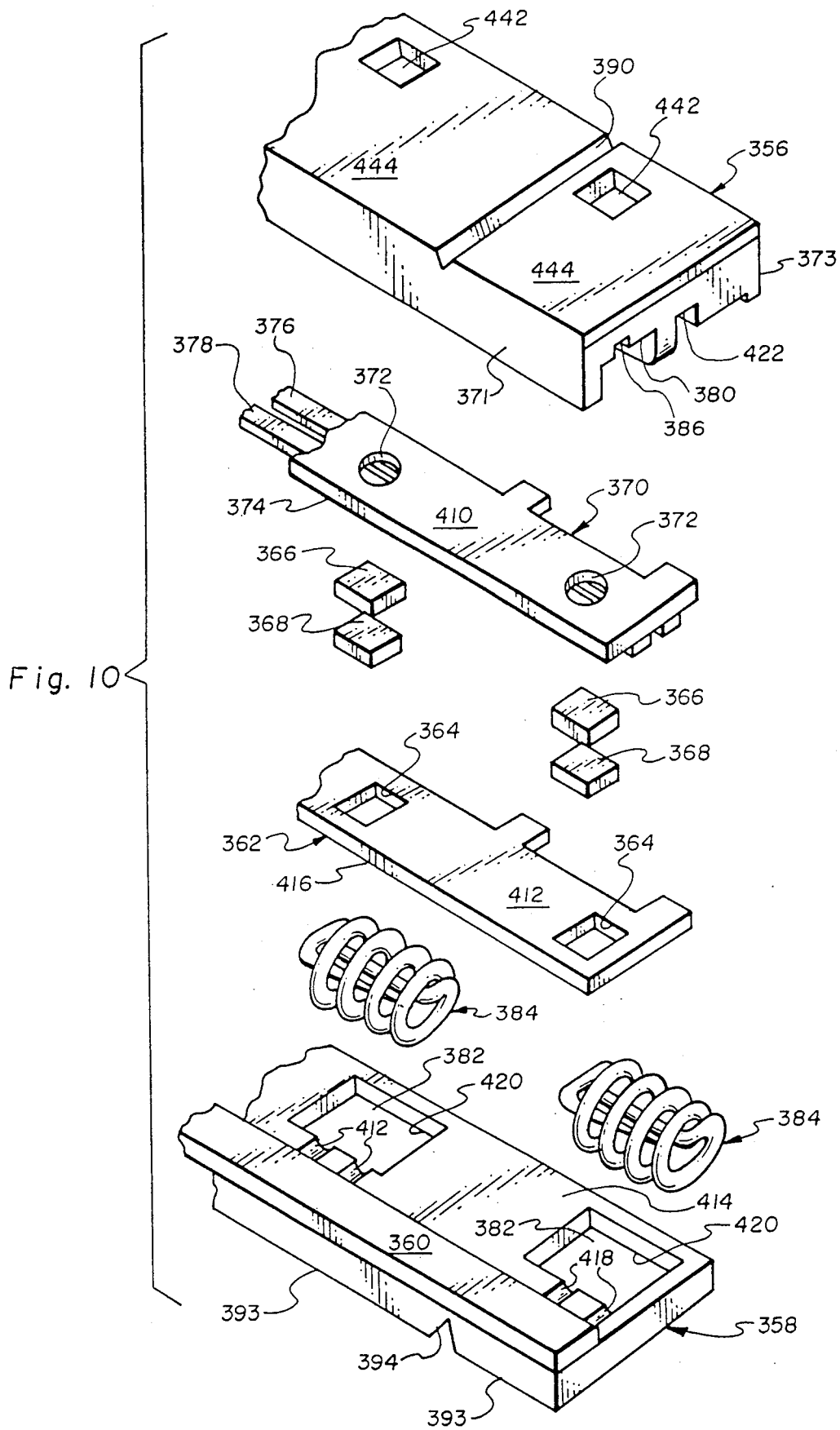

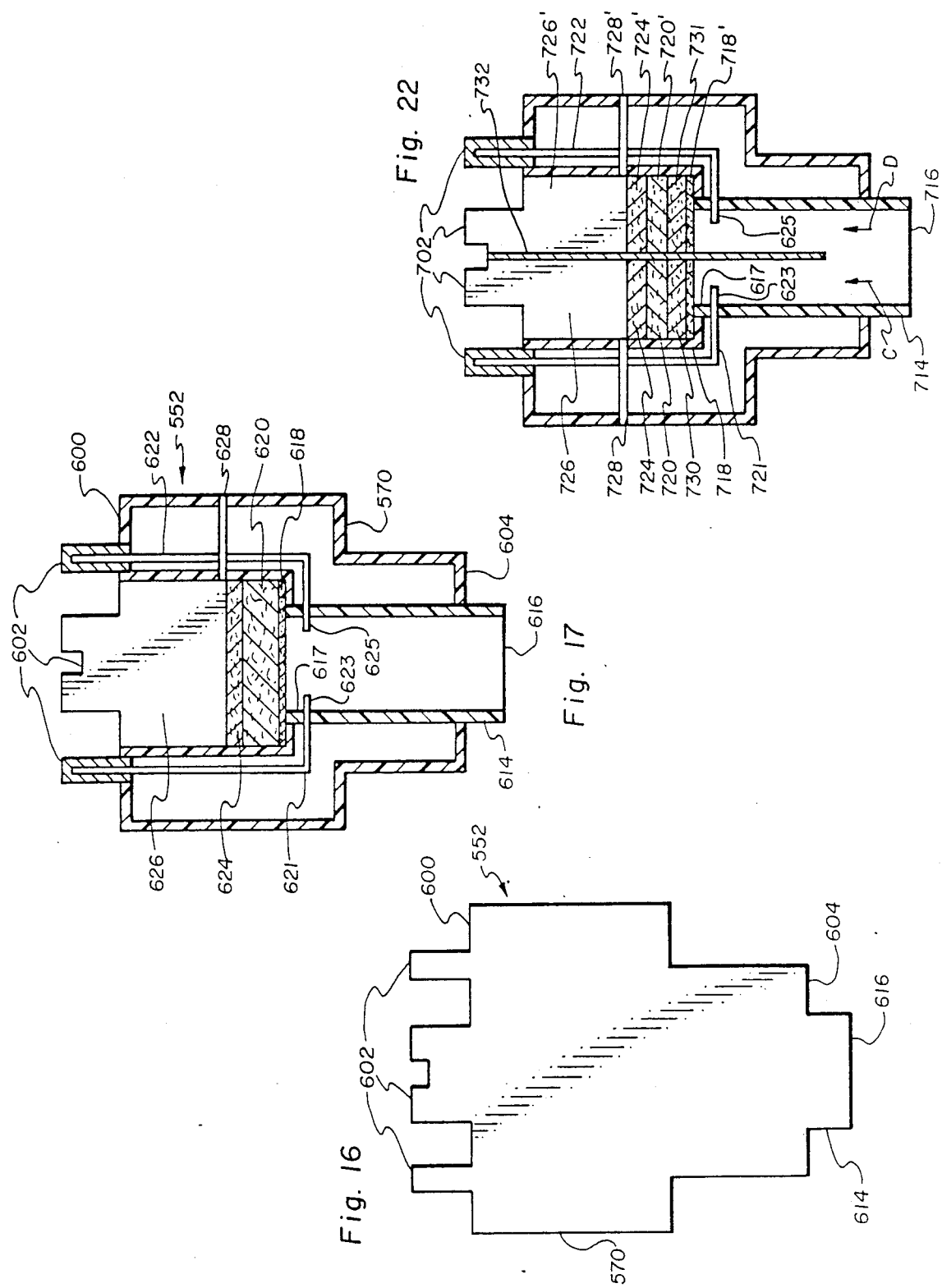

MEDICAL DROPLET WHOLE BLOOD AND LIKE MONITORING

CONTINUITY

This application is a division of our copending U.S. patent application Ser. No. 256,678, filed Oct. 12, 1988, now pending.

FIELD OF INVENTION

This invention relates to assays for determining an analyte, and to sensing means used in conjunction with such assays. More particularly, this invention relates to assays for analytes which employ as a tracer in the assays a ligand labeled with mercury or labeled with mercury releasing means and to an assay kit containing this tracer. The present invention also relates generally to the field of quantitative analysis of a desired constituent within a liquid and more particularly to a novel system by which one or more constituents within or forming part of a whole blood specimen from a medical patient or an animal or like liquid sample may be quantitatively ascertained inexpensively, for example, using a finger prick droplet blood specimen, at a site selected by the user, including the immediate vicinity of the patient, at the time shortly after the liquid specimen is obtained.

PRIOR ART

Various types of assays for analytes such as glucose, theophylline, phenytoin, cyclosporin, digoxin, cholesterol, and drugs of abuse (e.g. marijuana, cocaine) are known in the art. These assays may employ enzyme, radioactive, fluorescent, chemiluminescent, or other markers. The samples tested for analyte in conjunction with these assays include blood, cerebral spinal fluid, and urine. The types of assays described above, however, cannot be easily undertaken using a portable device which also enables one to obtain almost immediate results.

Except for a few blood testing instruments, which are nonanalogous to the present invention, the medical profession, with all of its expertise and massive funding of research, has been critically dependent upon centralized medical laboratory testing of blood and like liquid specimens at a site remote from the patient. Such laboratory testing of blood normally uses centrifuging to separate the serum from the remainder of the blood and then often processes the serum through a complex multiple channel machine. There are major disadvantages to such centralized testing, especially when considering nearly all such liquid samples are obtained at home, at a physician's office or clinic and at bedside in a hospital or a like facility. These central laboratory disadvantages include a sometimes intolerable but mandated lag time of many hours if not a day or more in obtaining the test results. Thus, treatment of contraindications may be delayed contrary to the best interests of the patient. Furthermore, since the constituency of the blood or other liquid in the body is a function of metabolism, among other things, the condition of the blood or other liquid in the body may have materially changed between specimen acquisition and availability of test results, thereby making treatment of contraindications potentially erroneous, and sometimes hazardous. Because each specimen must be passed through many hands, there is a recognized risk of error and the cost of delivering such services is very expensive. Correlation between the patient and the specimen can be misplaced, resulting in treatment being extended to the wrong patient. The risk that part or all of a specimen may be lost is increased by the need for many people to handle the sample. Loss of an entire sample necessitates that the acquisition and testing process be repeated, incurring further patient trauma, delays and additional significant costs. At times the large size of blood specimens required by central medical testing laboratories makes it very difficult to repeatedly monitor the blood characteristics of neonates and persons who are in a weakened state or who are critically ill.

Certainly, given the disadvantages cited above and others as well, if a better blood and/or other liquid screening, monitoring and testing system had been heretofore apparent to those of ordinary or inventive skill in the medical arts, it would be in place and available for use. Instead, almost universal dependency on central laboratory testing has for years been and remains the standard in the industry.

A single specific example will be helpful in focusing upon the weaknesses of central laboratory testing of blood. Directions given in the Physician's Register when prescribing theophylline for the asthmatic or emphysemic patient state that it is toxic above 20 mcg/ml and should be monitored when taken. It is prescribed for use in the home, but no instrument is available for such testing in the home today. Likewise, it may be monitored when taken in a doctor's office or when the patient is confined to a hospital or nursing home only through use of expensive equipment. As a consequence, the level of theophylline reaching the bloodstream of a patient may be ineffectively monitored, if at all, only on a deferred or delayed basis. The same type of problems exist using the central laboratory approach in testing the blood of a patient for other constituents, such as gentamicin, tobramicin, cholesterol, phenytoin (dilantin), phenobarbital, carbamezapine, cyclosporin, cocaine and, cannabis (marijuana).

Aside from central laboratory testing, several different systems or instruments are currently being employed in or have been proposed for the measurement of the many analytes found in blood. Each of these have shortcomings which restrict their breadth of use to areas other than whole blood assays. Almost all are not adaptable to small (pocket portable), simple to operate, or inexpensive one step instruments. Following is a list of these systems or instruments with a brief description of the shortcomings of each as they relate to whole blood assay:

| Nature of Assay | Shortcomings |
| --- | --- |
| Enzymatic | Difficult to use in whole blood. Dependent upon color change or generation, absorption and reflectance. Requires power consuming light source and optical systems and media is serum, csf (cerebral spinal fluid) or urine. Has been used with whole blood, using membrane separation techniques. Use has been limited to glucose and other assays compatible with enzyme chemistry |
| Nephelometry | Cannot be used in whole blood. Requires a nephelometric detection system which is not amenable to a small, portable instrument and media is serum, csf or urine. |
| Radioactive markers | Costly disposal process. Not considered safe to handle by untrained personnel. Requires shielded detector. Is large, not portable. Reagents have limited shelf life. Can test whole blood only when used in heterogeneous assays. |

-continued

| Nature of Assay | Shortcomings |
| --- | --- |
| Fluorescence | Difficult to use in whole blood. Requires power consuming light sources and optical systems and, therefore, cannot be small and portable. Media is usually serum, urine or csf. |
| Chemi-luminescence | Cannot be used in whole blood. Reagents are not stable enough for commercial applications. Requires photon counting for sensitivity. Media is serum, urine or csf. |
| Ion Selective Electrodes | Can be used in whole blood, but membrane and other related maintenance prevents use as a simple instrument. Media is serum, urine or csf. |
| Biosensor Electrodes | Use restricted to glucose. Barrier is the cost and complexity manufacture of the sensors themselves. |
| Spectrographic Analysis | High instrument cost, high power required and high volume (space) required. Only clear liquids can be tested. |
| Chemfet | Relatively high cost nondisposable sensors are required. No useful test available, even though technology is more than a decade old. |
| Surface Phenomena | Commercial testing projected to be more than ten years away. |

Today, there are very few bedside tests, even though testing in hospitals is performed in relatively large volumes and serves an important need when caring for the critically ill. Some of the reasons for few bedside tests are:

(a) Costs of instruments to perform the tests require centralization of the test laboratory to allow the instrument cost to be spread across many tests;

(b) The high degree of expertise required to run the test, including the need for regular calibration procedures, requiring a high degree of training and quality control;

(c) The dangers of test materials being used (e.g. radioactive assays), requiring special handling and disposal;

(d) The amount and time of processing, making such activities incompatible with bedside care; and (e) Data reduction and interpretation, requiring special laboratory personnel.

There is an almost universal blood testing requirement that the red cells be separated from the serum to accommodate testing using today's laboratory equipment. Centralized laboratory procedures require the saving of samples for follow-on testing, the establishment of standardized procedures for efficiently handling large volumes of tests, scheduling of test processing, dealing with sample and patient identification, test requesting, and result reporting. Most of these procedures and operations have resulted from the fact that satisfactory patient testing with accurate results available quickly at the bedside has not been technically achievable prior to the present invention.

Of course, there are many tests which can be performed at the bedside today. Patient vital signs, including heart rate, temperature, respiratory rate, etc. are routinely part of bedside test procedures. In some cases, tests for therapeutic drug monitoring are becoming available. An example is the immunochromatographic theophylline test ("Acculevel", by Syntex Medical Diagnostics) which is manually performed. It is reported easy to use (Clinical Chemistry, Vol. 34, No. 2, 1988, Page 428), but is labor intensive, requiring the user to perform a number of steps, even though it is advertised as a "single step chemistry". The blood is required to be accurately pipetted (in the range of 20 ul samples), it must be mixed with a reagent, and the whole reaction must be accurately timed (20 minutes), stopped and read. This test is visually interpreted, requiring training to achieve acceptably precise results.

Even with the advent of some bedside and home testing (e.g. glucose), the major volume of tests are still performed in the clinical laboratory, primarily because of economic and skilled personnel restrictions.

In summary, fluorescence, nephelometry, most color methods, radioimmunoassay, chemiluminescence, and spectrographic analysis are unacceptable for large scale use because of the complexity of processing both the whole blood and serum before and during the measurement. This complexity has resulted in high cost, though high throughput, instruments which are not economically justifiable for field applications (remote from clinical laboratory). Recent work in glucose measurement with the Johnson and Johnson "One Touch" and the "ExacTech" by Baxter Laboratories have provided so called single step glucose measurements in instruments targeted for the home diabetic market. The "One Touch" and "ExacTech" technologies are not directly applicable to competitive immunochemistry testing, however. Both are enzyme dependent.

From the foregoing, there has existed for a protracted period of time a need for a whole blood and other liquid analyzer having the following attributes and characteristics: the test results may be known at bedside or to the patient at home shortly after a specimen is taken; the test requires only a droplet of blood or other liquid for analysis; the test requires no separation of the constituents of the blood; the test instrument is simple to use requiring little training and obviating complex procedures; the test instrument is portable and preferably pocket portable; the test reagents are low cost and disposable; the technology produces significant sensitivity and accurate test results in an instrument which is error free in its operation and not strictly enzyme dependent; the test disposable provides a long shelf life; the test technology performs clinically acceptable, competitive immunochemistry for a large number of assays respecting a wide spectrum of analytes; the instrument use does not present calibration problems; and the results stored in the instrument can be readily transferred to computer data system of a hospital, doctor's office computer or the like.

BRIEF SUMMARY AND OBJECTS OF THE INVENTION

In brief summary, the present invention overcomes or substantially alleviates the aforesaid problems of the prior art and comprises a novel medical whole blood and other liquid analyzing system whereby: assay test results may be known at bedside or to the patient at home shortly after a specimen is taken; the test requires only a droplet of blood or other liquid for analysis; the test requires no separation of the constituents of the blood; the test instrument is simple to use requiring little training and obviating complex procedures; the test instrument is portable, preferably pocket portable; the test reagents are low cost and disposable after a single use; the technology produces significant sensitivity and accurate test results in an instrument the operation of which is error free and not strictly enzyme dependent; the test disposable provides a long shelf life; the test technology performs clinically acceptable, competitive immunochemistry for a large number of assays respecting a wide spectrum of analytes; the instrument use does not present calibration problems; and the results stored in the instrument can be readily transferred to the computer data system of a hospital or the like.

This invention comprises a mercury-aluminum sensor which mercury materials are used in concentrations not found in living beings (humans and other animals). Mercury [Hg] is initially attached to a tracer backbone or nucleus forming the source of the tracer. The tracer is used in a competitive immunochemistry or similar reaction, where the tracer is competitively freed by binding of the test analyte. Mercury attached to the released tracer is selectively released by a reagent, e.g. a metal salt (for example, nickel [Ni] in the presence of ammonium ions [$NH_{4+}$]) near an aluminum [Al] electrode. The mercury disturbs the aluminum oxide and hydroxide layers allowing electrical current to flow in patterns described hereinafter, which are functions of the mercury concentration at the surface, the concentration gradient of the mercury tracer in the liquid above the aluminum surface and, to a lesser extent, the concentration of the mercury releasing metal salt.

Measurable and analytically meaningful quantities of mercury are delivered to the surface of the aluminum electrode to produce the sensor activity. Competitive chemistry techniques, employing a specific analyte tracer and reagents for each assay type, are used. All chemical reagents and sensor parts are preferably packaged within a disposable sensor housing. The mercury containing analyte tracer comprising a specific molecule or synthetic polymer, is selectively released (usually competitively with the test analyte) within the sample fluid and is transported with the liquid specimen to the aluminum surface. The released mercury interacts with the activated aluminum surface to produce the detectable signal of the sensed reaction, which is a known function of the amount of the constituent (analyte) of the liquid specimen being quantitatively determined.

The instrument is a self-contained on-site clinical laboratory.

The sensor may be disposably housed in a hand-held instrument. Where blood is the medium to be tested, the instrument, as presently contemplated, comprises a lancet used to pierce the skin allowing transcutaneous blood flow for sample acquisition. The instrument receives the blood droplet sample, processes the test, reduces the sample data, and reports or displays the results automatically, requiring only the sensor be momentarily touched to the blood droplet sample after it accumulates at the surface of the skin. Thus, only very small volume liquid samples are required, i.e. less than 50 microliters.

The sensor has a broad field of effectiveness in accurately determining the quantity of any one of several analytes in the liquid sample. The sensitivity of the sensor is useful across a wide spectrum of analytes, e.g. from glucose to theophylline in blood samples. The operation of the instrument is simple, requiring little if any training and yet yields reliable and reproducible results. The instrument and sensor may be self-calibrating or have an internal feature to compensate for time dependent changes or sample variations. In most if not all applications, measurable results are known at the sample-taking site or at another desired site in less than five minutes. Even though only very small specimens are required, the sensor functions substantially independently of sample volume, surface wetting, hematocrit, sensor orientation, sample volume and intrasensor transport time, temperature, and other patient-to-patient variations. The instrument has a long shelf life and the accuracy of the test results are not materially effected by the time the sensor is stored prior to use. The instrument produces results which are clinically acceptable in terms of accuracy, precision and sensitivity across the full range for each assay available. The sensor is a low cost disposable; however, its field of use does not exclude the laboratory because its use there would greatly simplify laboratory procedures. For example, the present system does not require centrifuging of a liquid specimen.

The present invention accommodates a single instrument/single analyte approach as well as detection of several analytes using a manifold of instruments embodying the present invention.

It is contemplated that a magazine within the instrument may be loaded with a chain or packet of disposable sensors which are thereafter used successively from time-to-time until the supply is exhausted and all the remaining sensor chain or packet is ejected, at which time another chain or packet of sensors is introduced into the instrument.

The present invention, in further brief summary, is characterized by novel assay and sensing inventions for determining analyte in a liquid, particularly in whole blood and other biological specimens.

With the foregoing in mind, it is a primary object of the present invention to overcome or substantially alleviate the above-stated problems of the prior art.

Another significant object of the invention is the provision of a novel medical whole blood and other liquid analyzing system, and related methods.

It is a further dominant object to provide a whole blood and other liquid analysis system having one or more of the following features: test results may be known at bedside or to the patient at home shortly after a specimen is taken; the test requires only a droplet of human or animal blood or other liquid for analysis; the test requires no separation of the constituents of a blood specimen; the test instrument is simple to use, requiring little training; the technology obviates complex procedures and is not strictly enzyme dependent; the test instrument is portable preferably pocket portable; the test reagents are low cost and disposable after a single use; the technology produces significant sensitivity and accurate test results quickly in an instrument the operation of which is error free; the test disposable provides a long shelf life; the test technology performs clinically-acceptable competitive immunochemistry for a large number of assays respecting a wide spectrum of analytes; the instrument use does not present calibration problems; the results stored in the instrument can be readily transferred to the computer data system of a hospital or the like; the sensor accommodates use away from as well as in the laboratory; the instrument comprising a mercury and aluminum sensor which generates a signal representative of the quantity of a predetermined analyte present in the liquid specimen; the technology does not require centrifuging of the liquid specimen; the sensor utilizes a mercury containing analyte tracer chemically released so as to create electrode surface activity which can be detected, e.g. production of a signal at an electrode representative of the quantity of the test analyte present in the liquid specimen; the instrument measures and records time and date, the instrument generates data which can be stored and recalled with the recorded time and date of the test; the sensor functions accurately notwithstanding variations in rate of surface wetting, hematocrit, sensor orientation, sample volume, internal transport times, temperature and other patient-to-patient differences; the sensor may be self-calibrating or internally referenced to compensate for any time dependent change or specimen variation; the sensor operates in many biological liquids, such as whole blood, serum, urine and cerebral spinal fluid (csf); the sensor has sufficient gain to produce detectable results with competitive precision at low analyte concentration levels; the tracer involves chemical coupling to the analyte of interest without markedly effecting the activity of the attached analyte; the tracer has low non-specific reagent binding; the assay chemistry is sufficiently broad to accommodate a large number of assays. Enzyme independence, as used herein, means that enzyme use is not essential to the carrying out of the present invention and does not obviate use of one or more enzymes to increase sensitivity or reduce reagent cost.

It is another dominant object to provide a bioassay instrument which receives a plurality of disposable sensors which are used successively from time-to-time by the user until the supply is exhausted and ejected, following which the process is repeated.

It is another paramount object to provide a bioassay instrument which can be used alone to quantitatively detect a predetermined analyte in a liquid sample, provided, however, a plurality of the instruments may be used at a single site to quantitatively detect several predetermined analytes in a liquid sample at a common point in time.

It is another paramount object of the present invention to provide an assay for an analyte which can be readily carried out, and to provide for a portable and easy to operate sensing means for conducting such assays.

In accordance with one aspect of the present invention, there is provided an assay for an analyte which employs as a tracer in the assay a ligand labeled with mercury or mercury releasing means. The ligand used in producing the tracer is one which is bound directly or indirectly to the analyte or to a binder for the analyte. More particularly, an analyte is determined by an immunoassay or competitive or displacement binding procedure (sometimes referred to as a protein binding assay) wherein the tracer employed in the assay is labeled with mercury or mercury releasing means and the presence and/or amount of analyte is determined by determining a change in at least one property or characteristic of a metal which interacts with mercury directly or indirectly from the tracer.

The term mercury as used herein generally refers to mercury as a salt, and/or in an ionic form, and/or in a chelated state, etc. Thus, the mercury, as a label in the tracer or releasable by the tracer, may be present as a mercuric salt or mercuric ion and the term "mercury" as used herein encompasses such a mercuric salt and/or ion.

In an immunoassay procedure, there is formed a bound tracer phase in which the tracer is either bound to a binder for the analyte or directly or indirectly to the analyte and a free or unbound tracer phase. In accordance with an aspect of the present invention, the presence and/or amount of analyte is determined by determining a change in at least one property or characteristic of a metal which interacts with mercury directly or indirectly from the free and/or bound tracer phase.

Thus, the presence and/or amount of analyte may be determined by causing the mercury to interact with a metallic surface and then determining a change in one of the properties which result from such interaction.

Mercury is known to interact or react with various metals. Such interaction may sometimes form what is referred to as an amalgam.

The term interact, as used herein, encompasses such amalgamation of the metal, as well as other reactions, reductions and/or oxidations. For example, the metal with which the mercury interacts may be part of an electrode or electrodes. Interaction of the mercury with the electrode or electrodes changes a property or properties of the electrode or electrodes such as adherence of protective surface film or layers. Changes in these protective films are manifest as current changes, changes in resistance or capacitance, electrolytic changes, etc., which may be measured. The presence and/or amount of analyte is determined by the measurement of one or more changes in the properties of the metallic surface with which the mercury interacts. Other means of determining interaction of mercury with a metal include measuring the amount of heat generated by the exothermic interaction between the unprotected metal and its environment; measuring the change of mass of the metal; and visual and/or optical changes associated with the mercury dependent reactions between the metallic surface and its environment.

It is known that most metals, with the exceptions of iron and platinum, interact with mercury. In a preferred embodiment, however, the metallic surface which interacts with the mercury is aluminum.

In accordance with a preferred embodiment, the mercury present in the bound and/or free tracer phase is released from the tracer and the released mercury is caused to interact with an appropriate metal. The mercury may be released from the tracer by the use of an appropriate releasing agent, such as a nickel salt, e.g. nickel chloride, nickel sulfate, nickel nitrate. Other releasing agents may include, for example, salts of sodium, iron, lithium, manganese or magnesium. A preferred salt is nickel chloride. It is believed that the metal ion of the releasing agent displaces mercury from the tracer. It is also possible to release mercury from the tracer by a releasing agent which changes pH; for example, reduction of pH to below 1 releases mercury from a PEI carrier agent, hereinafter described.

In a preferred embodiment, the releasing agent, in particular $NiCl_2$, is employed in conjunction with ammonium chloride. The presence of chloride ions is believed to form a complex with the released mercury and the presence of ammonium chloride as part of the releasing agent increases chloride concentration. It is to be understood, however, that the present invention is not limited to the presence of chloride ions as part of the releasing agent.

In accordance with a second embodiment, the label present in the tracer is a mercury releasing agent that causes, directly or indirectly, the release of mercury in a subsequent step. For example, the tracer may be composed of a ligand covalently attached to a suitable enzyme. The enzyme selected interacts with a mercury containing substrate, thereby releasing mercury or mercury containing polymers. These compounds further interact either directly with a suitable metallic surface, or with further releasing agents as previously mentioned (nickel chloride and ammonium chloride) and then with the metallic surface.

Other objects and features of the present invention will be apparent from the detailed description taken with reference to the accompanying drawings.

BRIEF DESCRIPTION OF THE DRAWINGS

FIG. 3 is a longitudinal cross-section of the cap of the instrument of FIG. 1 with the distal end thereof shown in its open, hinged position;

FIG. 4 is a fragmentary cross-sectional view of the proximal end of the instrument of FIG. 1 showing the battery, the battery bracket and the proximal cover plate;

FIG. 5 is a top plan view of a chain of frangible disposable sensors adapted to be inserted into the instrument of FIG. 1;

FIG. 6 is a cross-sectional view taken along lines 6—6 of FIG. 5;

FIG. 7 is a cross-sectional view taken along lines 7—7 of FIG. 5;

FIG. 8 is a fragmentary cross-sectional view taken along lines 8—8 of FIG. 5;

FIG. 10 is a fragmentary exploded perspective representation of components forming part of the sensor chain of FIG. 5;

FIG. 11 is a fragmentary plan elevational view, with certain parts removed for clarity, of the detent and release mechanism by which the sensor chain of FIG. 5 is held in a desired position and by which the sensor chain of FIG. 5 is advanced for removal of a used sensor and for disposition of an unused sensor for use;

FIG. 13 is an enlarged top plan view of a lancet in spring form, shown in its loaded position, one of which is present in each of the sensors of the sensor chain of FIG. 5;

FIG. 15 is a cross-section taken along lines 15—15 of FIG. 2;

FIG. 16 is a side view of a further embodiment of an assay package, or sensing device, in accordance with the present invention;

FIG. 17 is a cross-sectional view of the embodiment of FIG. 16;

FIG. 22 is a cross-sectional view of one more embodiment of a sensor in accordance with the present invention, showing a dual flow configuration;

DETAILED DESCRIPTION

General

Generally, the present invention relates to apparatus, and related methods, of quantitative detection of specific analytes in whole blood and other liquids at the sample acquisition site. Mercury (Hg) applied to Aluminum (Al) is known to destabilize the protective Aluminum Oxide ($Al_2O_3$) layer. The present invention is user-friendly and involves a mercury-aluminum dependent sensor wherein resulting activity at the aluminum surface, due to the interaction of aluminum and mercury is proportional to the quantity test analyte in the specimen. Mercury is not found in analytical quantities in physiological fluids and has been found to possess significant advantages as an analyte tracer.

Competitive chemistry, employing, preferably in dry format, the analyte mercury tracer and a complementary set of reagents for each specific assay, is used to deliver measurable and analytically meaningful quantities of mercury to an aluminum surface to produce the sensor activity correlative to the quantity of test analyte.

All chemistry reagents and sensor components are preferably prepackaged within a disposable sensor housing forming part of a hand-held instrument. Low cost materials are used, producing a unique interplay between organic and inorganic chemistry. The tracer, as stated, is a mercury containing specific molecule or mercury-containing synthetic polymer, which is selectively released by a chemical reaction with the test analyte within the sample liquid and is transported a minute distance within or by the sample liquid toward the aluminum surface. The released mercury then contact the aluminum surface. The released mercury interact with the aluminum surface and generate the activity, hereinafter more fully described, which is measured and a known function of the quantity or test analyte present in the specimen.

The instrument receives, identifies, and discharges one or more specific disposable sensors for a specific analyte. The presently preferred instrument also comprises a lancet associated with each sensor used to pierce the skin allowing transcutaneous blood flow for droplet sample acquisition. The inclusion of a lancet as part of the instrument is desirable but not critical, since independent finger-piercing means can be used in lieu of an instrument lancet. The sensor receives the blood sample, processes the test, and the electronics reduce and store the sample data in a cyclic buffer or the like, and report the results automatically in conjunction with both the date and time of the test, without human supervision or intervention, requiring only the sensor be momentarily touched to the blood sample droplet as it appears at the surface of the skin.

The Instrument

Reference is now made to the drawings wherein like numerals are used to designate like parts throughout. The presently preferred overall at-patient hand-held instrument, generally designated 50, is shown in FIGS. 1–15.

Figure 1:
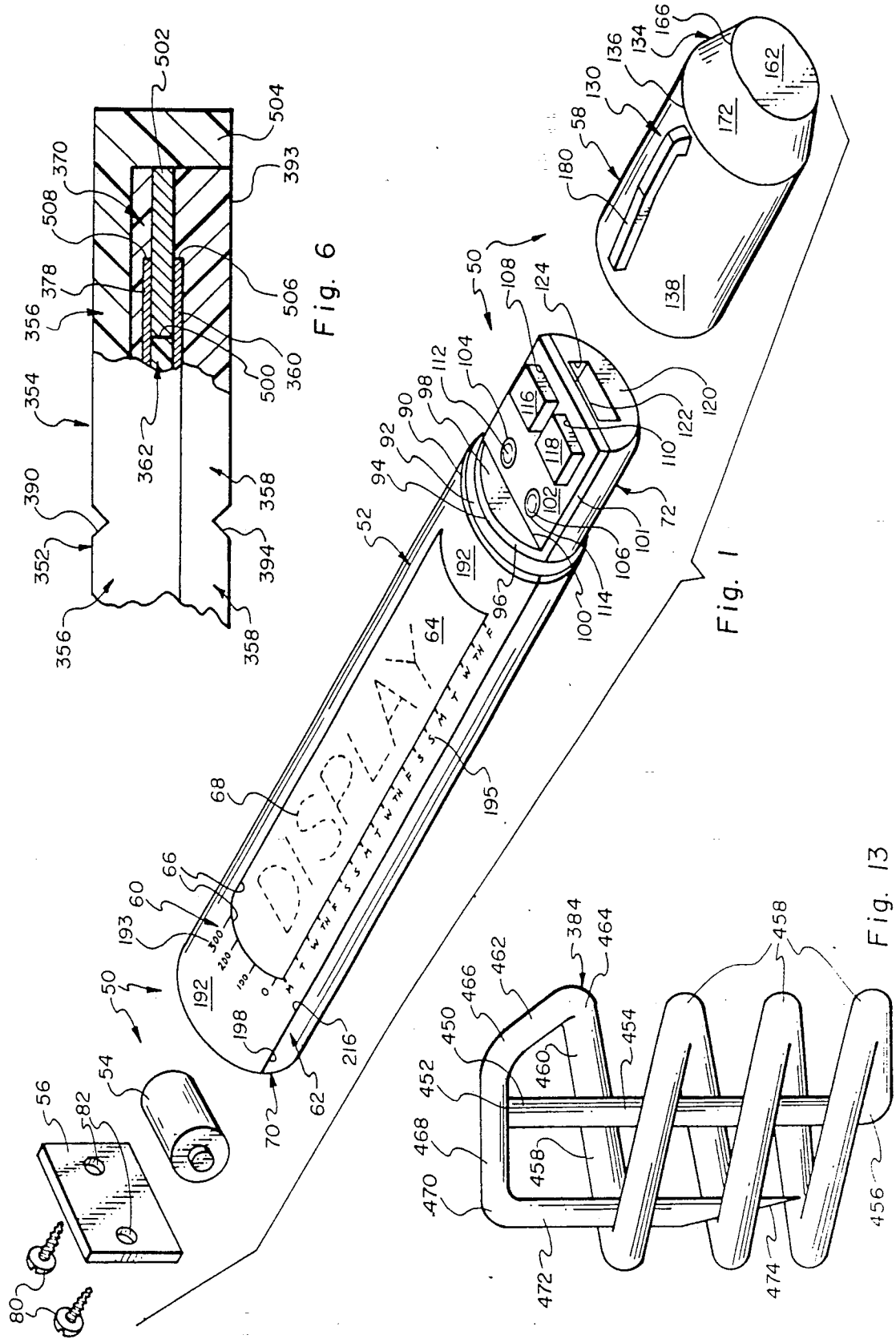
FIG. 1 is a partially exploded perspective of a presently preferred hand-held bioassay instrument embodying the principles of the present invention.

The illustrated instrument 50 comprises a main assembly, generally designated 52, of which battery 54 and proximal end cover plate 56 form a part thereof (see FIG. 1) and a distal end cap, generally designated 58. In FIG. 1, the main assembly 52 has a generally elliptical cross-sectional configuration defined by an exterior shell or housing which comprises a top cover, generally designated 60 and a bottom shell, generally designated 62, which are bonded or otherwise suitably secured together when assembled in fluid-tight relationship.

The main assembly 52, as viewed in FIG. 1, comprises a transparent window 64 recessed into the elongated somewhat rectangular opening 66 in flush relation with the top cover 60. See FIG. 15. The transparent window 64 is preferably of yieldable synthetic resinous material and is adhered along its edges to the edges of the cover 60 filling the opening 66 in fluid-tight relation. A liquid crystal display (LCD) 68 is carried by and forms a part of the main assembly 52, being disposed directly below the window 64 for visual observation by the user, as hereinafter more fully explained.

The main assembly 52 comprises a proximal end, generally designated 70, and a distal end, generally designated 72. As shown in FIGS. 1 and 4, a U-shaped battery bracket, generally designated 74, is carried at the proximal end 70 at compartment 76 within the lower shell 62. The battery 54 is held in press-fit relation within the bracket 74 in electrical communication with the electronics of the instrument 50, as explained in greater detail later. The proximal end 70 of the instrument 50 comprises a relatively large axially disposed rectangular aperture 78. Cover plate 56, which is illustrated as being generally rectangular in form, is adapted to cover the aperture 78, once the battery 54 has been installed, as illustrated in FIG. 4, in fluid-tight, lap joint relation with screw fasteners 80 securing the plate 56 in the assembled position shown in FIG. 4. The screws 80 respectively pass through apertures 82 in plate 56 and are secured in threaded blind bores 84 of radially directed flange 86 forming a portion of the proximal end 70 of the instrument 50. O-ring or other seals may be used between plate 56 and flange 86.

The distal end 72 of the main assembly 52 is inwardly stepped to form inwardly-directed radial shoulder 90. See FIGS. 1 and 2. Adjacent shoulder 90 is an O-ring 92 disposed in a groove 94 in surface 96. The O-ring is sized and shaped so as to seal against the interior of the cap 58, as hereinafter explained in greater detail. The surface 96 merges with a transverse inwardly directed flat radial surface 98, which in turn merges, at ninety degree corner 100, with an actuator panel wall 101 which comprises a top flat actuator panel surface 102 and a bottom surface 103. Wall 101 is illustrated as being interrupted by two circular apertures 104 and 106 disposed vertically therein and two rectangular apertures 108 and 110 also vertically disposed. See FIGS. 1 and 2.

Recessed actuator buttons 112 and 114 are exposed at apertures 104 and 106, respectively, and are disposed at a location generally below the surface 102 for manual actuation by a ball point pen or the like, as hereinafter explained in greater detail. Actuator buttons 116 and 118, respectively, project through apertures 108 and 110 to a location substantially above the surface 102, to be actuated by the user for purposes hereinafter explained.

The distal end 72 of the main assembly 52 comprises a distal edge of surface 120, which is illustrated as being transverse or normal to the longitudinal axis of the main assembly 52. Disposed through the wall 222 comprising the edge 120 is a slot 122 (FIG. 1) which opens at 124. The slot 122 is adapted to receive sensor chain, such as the one illustrated in FIG. 5, in a manner and for purposes hereinafter explained. Preferably, as delineated herein in greater detail, the cover 60 and bottom shell 62 are formed by injection molding of a suitable synthetic resinous material.

The interior of the main assembly 52 comprises a plurality of additional components which will be explained later.

The cap 58 is likewise preferably formed as a single piece from a suitable synthetic resinous material using conventional injection molding techniques. See FIGS. 1 and 3. As best illustrated in FIG. 3, the cap 58 is substantially hollow and comprises a main hollow body 130, a disinfecting swab 132, illustrated as being of generally cylindrical configuration constricted centrally to retain the same within the cylindrical body 130 and hinged lid generally designated 134. The lid 134 is hinged at site 136 to the hollow cylindrical body 130. See FIG. 3. Preferably, hinge 136 is a plastic hinge, sometimes called a living hinge.

The oval hollow body 130 comprises an exterior oval 360 degree surface 138 comprising part of a relatively thin wall 140 which also comprises an interior surface 142. Hollow body 130 comprises a proximal opening 144 and a distal opening 146. Opening 144 is transversely slightly larger than surface 96, but less than the transverse position of the O-ring 92 so that the lid, when placed upon the distal end 72 of the main assembly 52 creates a fluid-tight seal.

Interior surface 142 is inwardly stepped at radially directed shoulder 148, which merges with transversely reduced axially-directed surface 150. Surface 150 extends to the distal opening 146, but is centrally interrupted by an inwardly directed radial flange 152, illustrated as being of uniform thickness throughout. Flange 152 has an aperture 154 centrally disposed therein. The diameter of the aperture 154 is less than the unstressed, at-rest diameter of the cylindrical cotton swab 132. Thus, when the cotton swab is compressively inserted through the aperture 154, the central portion thereof is constricted to secure the swab 132 in the position illustrated in FIG. 3. The dimensions of the swab 132 are selected so that the leading edge 156 thereof is exposed beyond the distal opening 146.

The flange 152 merges with a proximally extending cup-shaped enclosure, generally designated 153. Enclosure 153 comprises a cup-shaped wall 155, illustrated as being of uniform thickness, which defines a closed hollow interior 157. Disinfectant is contained within the interior 157 to provide an extended supply where negligible leakage and evaporation occurs. Initially, disinfectant may be placed in the interior 157 (with the lid 134 open and the cap 58 vertically disposed) before the wick 132 is placed in aperture 154. However, at any time, with the wick 132 in place, the needle of a hypodermic syringe loaded with disinfectant may be placed through the wick 132 into the interior 157 and discharged to establish or replenish the supply.

The surface 150 at one side thereof adjacent the distal opening 146 is interrupted by a V-shaped notch 158.

The lid 134 comprises a blunt distal wall 160, illustrated as being of uniform thickness and comprising a flat transverse exterior surface 162 and a flat interior transversely directed surface 164. The wall 160 merges at an oval interface 166 with a tapered, generally oval wall 168, which comprises a tapered interior surface 170 and a tapered exterior surface 172. The proximal end of the wall 168 integrally merges with the hinge 136 along one side thereof.

At the opposed side, wall 168 comprises a generally S-shaped latch 174. Latch 174 is interiorly stepped to fit within the opening 146 and comprises a V-shaped lip 176, which is sized, located and shaped so as to be inwardly displaced when forceably caused to contact the hollow body 130, contrary to the memory of the synthetic resinous material from which the lid 134 is made and to radially move, under force of said memory, into contiguous relation with the V-shaped slot 158 in the surface 150 when in alignment therewith to create a releasable latch and a fluid-tight relationship between the lid 134 and the hollow body 130. The user may easily grasp the lid 134 of the cap 58 and displace the same between the closed and opened positions illustrated in FIGS. 1 and 3.

The absorbent wick 132 functions to accommodate application of a small amount of liquid disinfectant to the lancing site (the finger tip site, where a droplet of blood is to be the liquid specimen) prior to lancing. The body 130 and the lid 134 are constructed such that evaporation of the disinfecting liquid contained in the wick is no more than negligible, when the lid 134 is placed and retained in the closed position as illustrated in FIG. 1. The wick 132 may be manually replaced from time-to-time. It is presently preferred that the disinfecting liquid be isopropanol. The instrument user initially and subsequently adds his own disinfecting liquid to the wick, as required. Thus, the wick 132 is manufactured and stored prior to use in a dry state. The cap 58 and more particularly the hollow body 130 is illustrated as comprising an integral pocket clip 180, by which the entire instrument may be secured in the user's pocket. Of course, clips of different configuration and either integral or separate and fastened to the cap 58 may be used.

The construction of the cap 58 is such that the surface 142 engages and compresses the O-ring 92 so that the interface between the cap 58 and the main assembly 52 becomes fluid-tight.

Figure 2:
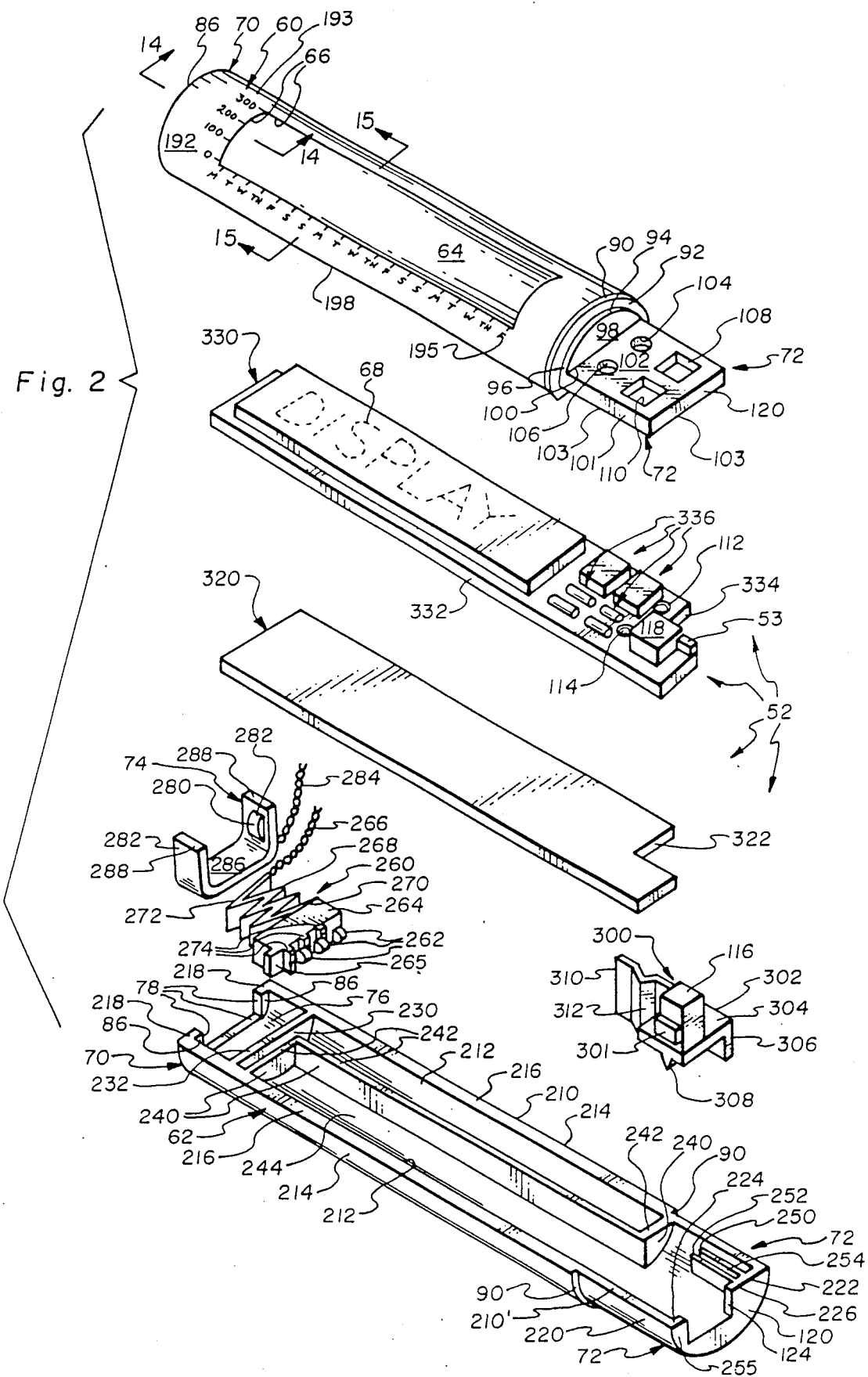
FIG. 2 is an exploded perspective of the bioassay instrument of FIG. 1 with the cap, battery and battery cover removed.
Figure 14:
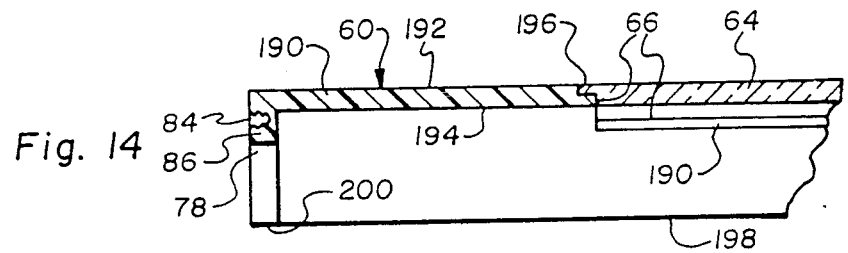
FIG. 14 is a cross-section taken along lines 14—14 of FIG. 2.

Reference is now made to FIGS. 2, 14 and 15 for the purpose of providing more detailed information in respect to the interior of the main assembly 52. FIG. 2 illustrates the main assembly 52 in exploded perspective. The main assembly 52 broadly comprises top shell or cover 60, electronics assembly 330, slide plate 320, slider/contact assembly 260, battery clip bracket 74, release/detent assembly 300 and bottom shell 62.

As can be seen from the top portion of FIG. 2 and from FIGS. 14 and 15, the top shell, top housing or cover 60 curvilinearly spans through 180 degrees in a direction transverse to the longitudinal axis of the main assembly 52. The cover 60 comprises an integral wall 190, illustrated as being of uniform thickness between proximal wall 86 and shoulder 90, and comprising a curvilinear exterior surface 192 and a curvilinear interior surface 194. The previously described elongated generally rectangular opening 66 is centrally disposed through the wall 190. The previously described transparent window is placed in the opening 66 in such a way as to create a butt joint, shoulders 196 preventing the window from being displaced inwardly. See FIGS. 14 and 15. Preferably a suitable bonding agent or adhesive is disposed at butt joint between the edges of the window and the edges of the opening 66. The wall 190 terminates in opposed horizontally-directed side edge faces or surfaces 198. It is to be appreciated that while the instrument is illustrated and sometimes described as being disposed in a horizontal position in the drawings, such an orientation is not essential or even recommended for use of the disclosed instrument. Proximal transverse end wall 86, as seen in FIGS. 14 and 15 terminates in a pair of opposed transversely directed horizontal edge surfaces 200. The edge surfaces 198 and 200 are secured, as hereinafter more fully explained, to the lower shell 62 in integral fluid-tight relation.

The actuator panel plate 101, extending distally from the cover 60, is essentially planar, disposed horizontally (as illustrated in the FIGS.), of uniform thickness and comprises top and bottom flat surfaces 102 and 103. The top cover or shell 60 and plate 101 are preferably formed of injection molded high strength synthetic resinous material. Currently, nylon and fiber-reinforced nylon are preferred.

The window 64 is preferably formed of polycarbonate or acrylic synthetic resinous material. Preferably, adjacent the transverse dimension of the window 64, in the face of the plastic shell 60 is disposed indicia 193 comprising the range of concentration of the test analyte, the quantity of which is being ascertained. Thus, graphic or bar information displayed upon LCD 68 is visually quantified by reference to the analyte concentration indicia. Furthermore, FIG. 2 illustrates that indicia 195 representative of the days of the week are also molded upon the top surface 192 for visual use in reading the LCD 68 in terms of the quantities of test analyte found in blood droplets from the same patient on a day-to-day basis, in accordance with the operation of the electronics and data processing capability of the instrument 50, hereinafter explained.

The bottom shell 62 is preferably of injection molded synthetic resinous material. Currently, nylon and fiber-reinforced nylon are preferred. The bottom shell 62 comprises a rigid longitudinally elongated wall 210 which, with the exception of the stepped distal end 72 is illustrated as being of uniform thickness throughout. Wall 210 curvilinearly, in somewhat of an elliptical configuration, spans transversely from side to side. The wall 210 comprises an interior curvilinear surface 212 and an exterior curvilinear surface 214. Surface 210 terminates in opposed horizontally directed side edges 216, which are sized, shaped and located so as to become flush with previously described edges 198 of the cover 60 when fully assembled. Transversely-directed horizontally-disposed opposed edges 218 are disposed in the same plane as edges 216 and are sized, shaped and located so as to become flush with the edges 200 of the cover 60 when assembled. Edges 218 and 200 are located at the proximal end 70 of the main assembly 52. A suitable bonding agent, adhesive, weld medium or the like permanently joins edges 218 and 200 and edges 216 and 198 so that the resultant exterior housing is fluid-tight along said interface. The wall 210 is stepped at shoulder 90 so that the wall thickness is transversely reduced at exterior surface 220 disposed near the distal end 72 of the shell 62.

Surface 220 comprises part of reduced wall 210'. Wall 210' integrally merges with the transverse wall 222 at the distal end 72 of the shell 62.

Wall 222 terminates in blunt transversely exposed vertically-directed distal end surface 120 and comprises transversely-oriented horizontally-disposed edge surfaces 224 and 226. Edge surfaces 224 and 226 are disposed in the same plane which contains surfaces 216 and 218 and are caused to be substantially flush with the lower surface 103 of the distal end panel plate 101 of the top shell 60 when assembled. Adhesive, bonding agent, a suitable weld medium or the like is preferably placed at the interface between edges 224 and 226 and surface 103 so as to integrally join the same. Likewise, the distal portion of edges 216 are adhesively or otherwise suitably secured to the lower surface 103 of the actuator panel plate 101.

Once the main assembly 52 is fully assembled, access to the interior of the shell 62 may be accomplished only through the battery opening 78 at the proximal end 70 of the assembly 52 and the sensor chain insertion slot 124 at the distal end of the assembly 52.

As illustrated and presently preferred, shell 62 is of one-piece construction, preferably formed of synthetic resinous material using conventional one-shot injection molding techniques. Internally, the bottom shell 62 comprises a transverse wall 230 illustrated as being of uniform thickness throughout and disposed in a transverse orientation to the longitudinal axis of shell 62. The wall 230 is integral with the wall 210 and comprises a top transverse edge 232, also disposed in the plane containing edge surfaces 216 and 218. The wall 230 defines the forward limit of the battery compartment 76.

The interior of the bottom shell 62 also comprises a Z-shaped wall 240, the staggered ends of which are integral with the surface 212 of the wall 210. The bottom of wall 240 is integral with the bottom portion of the wall 210 at surface 212. The wall 240 comprises a top edge 242 disposed in the plane containing edges 216 and 218. The Z-shaped wall 240 is constructed so as to define a chamber 244, which is sized, shaped and located to readily accept each sequentially inserted chain of sensors, preferably of the type illustrated in FIG. 5. Insertion into the chamber 244 occurs through the opening 124.

The distal end 72 of the shell 62, at the interior thereof, comprises a pair of longitudinally directed axially offset walls 250 and 252, defining a relatively narrow space 254 therebetween. The walls 250 and 252 are illustrated as being of uniform thickness and are integral with the wall 210 at the lower portions thereof and with the wall 222 at the distal ends thereof. The walls 250 and 252 are rigidly disposed, as illustrated in FIG. 2, so as to snugly and retainingly receive support structure for button actuator 116, as hereinafter more fully explained.

The short proximal transverse leg of the wall 240 forms an abutment surface for a slider/contact assembly, generally designated 260, as hereinafter described.

The slider/contact assembly 260 comprises electrical spring contacts 262, schematically illustrated in FIG. 2. A slider plate 264 carries the spring electrical contacts 262 in the orientation illustrated in FIG. 2. Plate 264 is constructed dimensionally to be capable of sliding axially to and fro within the sensor chain-receiving chamber 244 adjacent the transverse proximal wall 240. The dimensions of the plate 264 further do not extend beyond the wall edges 242 so that interference between the reciprocation of the plate 264 and other internal parts of the main assembly 52 does not occur.

The slider/contact assembly 260 further comprises electrical wires 266 and a fan-fold compression spring 268. The fan-fold compression spring 268 is sized similarly to plate 264 so as to fit within sensor chain-receiving compartment 244 for reciprocation without interference with other internal parts of the main assembly 52. The fan-fold spring 268 connects at site 270 to the back surface of the plate 264. A suitable adhesive, bonding agent, welding medium or other fastening medium may be used to so attach the distal end of the spring 268 to the back side of the plate 264.

The proximal surface 272 of spring 268 is essentially flat and, in the assembled position, is bonded, glued or otherwise suitably secured to the forward face of the transverse proximal wall 240 in the chamber 244.

The width of slider plate 264 is somewhat less than the width of the chamber 244, but does not become eccentric or skewed since plate 264 merely follows the packet 350 of sensors 352, after attachment, as the packet is incremented out of the main body 52 during periodic use. The slider plate 264 comprises a side stop abutment 265 (FIG. 2) which helps maintain the plate 264 true during proximal to distal axial displacement. Stop abutment 265 also engages wall segment 255, when all sensors 352 of a packet 350 have been used, preventing the slider plate 264 from leaving chamber 244.

The electrical contacts 262 are preferably of wiping construction and make electrical contact with the proximal contact/key tab of the chain of disposable sensors, which are illustrated in FIG. 5, as hereinafter explained. The plate 264 is designed to slide axially back and forth within the compartment 244 under action of the spring 268 and manually-applied pressure and detent forces, as explained in greater detail later.

The plate 264 is preferably formed of dielectric synthetic resinous material, which produces low friction and is strong. It is currently preferred that nylon and/or teflon be used to form plate 264.

The plate 264 also comprises integrally molded key protrusions 274 (FIG. 5). Protrusions 274 are broken away in FIG. 2 for clarity of schematic illustration of the electric spring contacts 262. Protrusions 274 are constructed so as to fit within aligned key slots 276 disposed in the proximal end 278 of the chain of disposable sensors, as illustrated in FIG. 5. In this way, only the proper strip sensor for a specific test analyte is compatible with a specific version of the instrument 50. Of course, there are other ways in which harmony or compatibility between an instrument and a chain of disposable sensors may be appropriately keyed to prevent erroneous use of improper sensors. For example, a series of customized matching keys and keyways in the chain or packet bottom 358 and opening 124 and/or along the bottom of the chamber 244, respectively, or in the bottom of the slider plate 264.

Electrical leads or conductors 266 are flexible and electrically connect between the electronics 336 carried by the assembly 330 and contained within the main assembly 52 and the spring contacts 262.

The spring 268 serves to bias the slider plate 264 away from the proximal end 70 of the main assembly 52. It is presently preferred that the force of spring 268 be on the order of 0.5 to 2.0 pounds.

The battery bracket 74 is illustrated in FIGS. 2 and 4. Bracket 74 is formed of dielectric synthetic resinous material and comprises opposed conductive spring contacts 280 conventionally carried at the inside surface of each of two vertically-directed legs 282 of the bracket 74. As is conventional, the battery 54 (FIGS. 1 and 4) is press-fit within the bracket 74 so as to be compressively retained between the two conductive spring contacts 280. Electrical leads or conductors 284 connect between the electrical contacts 280 and the electronics 336 carried by assembly 330 and contained within the main assembly 52. A horizontal bridge 286, integrally interposed between the vertical legs 282, is preferably bonded, glued or mechanically secured to the shell 62 in compartment 76. Alternatively, the bracket 74 may be molded integrally with the bottom shell 62. The top horizontal edges 288 of the bracket 74, in the assembled position, are illustrated in FIG. 4 as being disposed slightly below the plane containing edges 216 and 218.

The actuator button 116 comprises part of a release/detent assembly, generally designated 300. See FIGS. 2 and 11. The assembly 300 comprises an L-shaped spring 302, which comprises a horizontal leg 304 and a vertical 306. The L-shaped spring 302 is illustrated as being of uniform thickness throughout and is comprised of a metal or synthetic resinous material which is somewhat yieldable when manual force is applied to the actuator 116 but comprises memory which restores the spring 302 to the unstressed position illustrated in FIG. 2, when the manual force at actuator 116 is removed. The vertical leg 306 is sized and shaped so as to snugly and restrainingly fit within the slot 254 between the two bottom shell interior walls 250 and 252. Thus, the horizontal leg 304 is supported in cantilevered relation partially over the chamber 244 internally adjacent the slot 124. The exposed bottom of the horizontal leg 304 comprises a V-shaped downwardly projecting protrusion 308, which functions, upon manual depression of the actuator 116, to break a frangible region 480 (FIG. 8) of a juxtaposed disposable sensor, of the type shown in FIG. 5, whereby the finger of a patient, whose blood is to be tested for the existence and quantity of a test analyte, is pricked to produce a droplet sample of blood, as hereinafter more fully explained.

As explained later in greater detail, the assembly 300 also has a magnet 301 mounted on the button 116 such that, in the unstressed position, the magnet is adjacent to a normally closed magnetic reed switch S3 (FIGS. 2 and 28) mounted on circuit board 332. Depressing the button 116 moves the magnet away from the immediate proximity of the magnetic reed switch S3, momentarily closing the reed connection to signal the microprocessor 750 the lancet has been triggered and automatically triggering an electronic test cycle.

The assembly 300 also comprises an axially-directed detent plate 310, which is integrally joined to the leg 304 and comprises a V-shaped detent 312. Detent plate 310 is made of a resilient metal or synthetic resinous material which can be manually deflected having memory which tends to restore the detent plate 310 to the at-rest unstressed condition when the manual force is removed. As illustrated in FIG. 11, the detent 312 of the detent plate 310 is biased to engage a notch 530 disposed between two contiguous disposable sensors 352 of a chain of sensors 350, such as the sensor chain illustrated in FIG. 5, in a manner and for purposes hereinafter more fully explained. The present invention contemplates that other forms of release/detent mechanisms may be used to releasibly restrain a chain of sensors at selected locations from time-to-time to accommodate analyte testing.

As can be seen from FIG. 2, the top of the bottom shell 62 is substantially internally covered by a slide plate 320, with the exception the region in which walls or plates 250 and 252 are disposed within the interior of the bottom shell 62. With the exception of notch 322, plate 320 is substantially rectangular and comprises dimensions corresponding to the inside dimensions of shell 60, internal of edges 216, 218, 224 and 226. The plate 320 is illustrated as being of uniform thickness. Slide plate 320 is of a suitable synthetic resinous material, nylon being presently preferred. Slider plate 320 functions to close the sensor chain channel 244 and to protect the underside of the electronics assembly 330. Notch 322 accommodates placement of the release/detent assembly 300 whereby actuator 116 is operatively exposed beyond the aperture 108 at the actuator panel plate 101.

The electronics assembly 330 comprises a base comprising a printed circuit board 332, which is shaped identical or substantially identical to plate 320, is illustrated as being of uniform thickness throughout and is generally rectangular in configuration, comprising a notch 334 to accommodate placement of the release/detent assembly 300.

The electronics assembly 330 comprises the previously mentioned LCD 68 and analog and digital components 336, hereinafter explained in detail. The electronics assembly 330 also comprises previously mentioned mode actuator button 118 and select button actuators 112 and 114. The function of the electronics will be described later. The electronic components 336, the LCD 68 and the actuators 112, 114 and 118 are conventionally mounted on the printed circuit board 332.

The illustrated disposable sensor instrument 50 is preferably similar in size and shape to a vest pocket flashlight. The clip 180 releasibly secures the instrument in the pocket of the user, e.g. a medical attendant, during periods of nonuse.

The Sensor and Sensor Chain of FIGS. 5–13 and Instrument and Sensor Use

Reference is now made to FIGS. 5–13, which illustrate a presently preferred chain, packet or linkage of breakaway sensors, generally designated 350. The chain of sensors 350 comprises, as illustrated, eight sensors, each generally designated 352, each for quantitatively detecting a specific analyte in a liquid sample. The sensors of packet 350 are frangibly linked together, as later explained. The use of the instrument 50 in conjunction with any sensor 352 makes the combination a self-contained chemical laboratory, which produces quantitative analyte detection results at or near the site of sample acquisition. The illustrated and described chain of sensors 350 and each sensor 352 thereof are specifically constructed for percutaneous, whole blood, long shelf-life applications. Each sensor 352, as explained in greater detail herein, is easily calibrated, usually at the factory. Operation of the instrument 50 in conjunction with any one of the sensors 352 requires only two user steps, i.e. lancing of the skin and touching of the distal tip of the sensor to the resulting droplet sample of blood surfacing on the tip of the finger so lanced. Preferably, the lancing site is first cleansed using the disinfectant in the cotton swab 132, although conventional applications of disinfecting liquid may be used and the swab 132 eliminated from the instrument. In addition to the plurality of sensors 352, which are frangibly joined one to another, the chain of sensors 350 comprises the previously described proximal keyway end 278 and a distal insertion tab, generally designated 354.

The chain of sensors 350 and each sensor 352 in particular comprise a top housing, generally designated 356, and a bottom main electrode-carrying plate, generally designated 358. The main electrode 360 (FIG. 10) is adhered to and carried at the top surface 414 of the plate 358. Electrode 360 extends from near the distal to the proximal end 278 of the chain of sensors 350. This extension includes traversing about half way along the insertion tab 354. As also best shown in FIG. 10, a pad-receiving plate, generally designated 362 and comprising spaced rectangular apertures 364, is contiguously disposed above the main negative electrode 360. Certain tracer and reagent pads 366 and 368, respectively, are sized and shaped to snugly fit in contiguous superimposed relationship within each rectangular aperture 364.

The chain of sensors 350 further internally comprises a sample flow-accommodating plate, generally designated 370. Plate 370 comprises circular, capillary-sized apertures 372. Each aperture 372 is constructed and located to be vertically aligned with an adjacent rectangular aperture 364 in plate 362 whereby a liquid sample passes through aperture 372 of sensor 352 being used to infiltrate the pads 366 and 368, for purposes and in a manner hereinafter more fully described.

Adhered to the underside 374 are liquid sensing conductors or electrodes 376 and 378, which run the length of the linked sensor 352. The electrode 376 terminates at the interface between the first-to-be-used sensor 352 and distal insertion tab 354, while electrode 378 extends about midway through tab 354, for a purpose yet to be explained.

As can best be seen from FIG. 10, a part of each electrode 376 and 378 is exposed at each aperture 372. Consequently, for purposes later explained, an adequate liquid specimen flowing through a given sensor aperture 372 will contact and electrically bridge or interconnect the electrodes 376 and 378 to produce an audible signal confirming to the user the presence and adequacy of the sample for analyte testing purposes.

The top housing 356 of the chain of sensors 350 is generally of an inverted U-shaped configuration and surrounds the top and sides of the plates 358, 362 and 370. The bottom plate 358, at the edges thereof is contiguous with and integrally connected, by adhesive or other suitable techniques, to the side flanges 371 and 373 of the top housing 356. Thus, there is provided between the bottom plate 358 and the top U-shaped housing an elongated chamber 380, into which the plates 362 and 370 with electrodes 360, 376 and 378 are positioned along the entire length of the packet of sensors 350. Spaced lancet receiving compartments 382 (one for each sensor 352) exist in longitudinal spaced orientation.

Each compartment 382 houses a spring-shaped lancet, generally designated 384. See FIGS. 7, 8 and 13.

Each sensor 352 includes a top capillary passageway 386 each opening into chamber 380. Each capillary passageway 386 is illustrated as being rectangular in cross-sectional configuration and L-shaped in the axial direction. See FIGS. 9 and 10.

Top housing 356 is of injection molded synthetic resinous material, which is readily manually frangible. Housing 356 has spaced transverse V-shaped notches 390 interrupting the top surface 444 at the connection frangible sites 392 between the linked sensors 352. A similar notch 390 is interposed in the top surface of the housing 356 between the insertion tab 354 and the number one sensor 352. The bottom surface 393 of the lower plate 358 is likewise interrupted by V-shaped notches 394 which are respectively located in vertical alignment with the notches 390 below each weakened frangible region 392. Each notch 394 extends across the bottom edges of flanges 371 and 373. Thus, when the user applies an upward or downward force on the insertion tab 354 or on an exposed used sensor 352, the housing 356, the plate 358 and the components therebetween will fracture at the frangible site 392.

The capillary passageway 386 is illustrated as being in the form of a channel disposed in housing 356 at the distal end of each sensor 352. It is presently preferred that each capillary channel 386 be treated with a surfactant to make it hydrophilic.

The packet 350 of sensors 352, as shown in FIG. 5, is entirely internally hermetically sealed at the time of manufacture and, preferably subject to conventional sterilizing techniques prior to distribution to the user. When a given sensor 352 becomes located at the distal end 72 of the main assembly 52, as explained herein, the distal entry port 400 of the channel 386 (FIG. 9) adjacent broken edges 402 and 404 becomes exposed for the first time. More specifically, when the preceding sensor 352, following use, is indexed forward and fractured from the packet 350 along its distal frangible site 392 to create exposed distal edge 402 of housing 356 and edge 404 of plate 358, the entry port 400 to capillary 386 is initially exposed. Thereafter, when the leading end of the instrument is placed so that a droplet specimen of blood on the fingertip of a medical patient is contiguous with the distal end 402/404 of an activated sensor 352 in alignment with capillary opening 400, blood will aspirate though the opening 400, along the capillary 386, through the associated aperture 372, into contact with electrodes 376 and 378, through the tracer and reagent pads 366 and 368 and into contact with the main negative electrode 360. See FIGS. 7 and 9. Testing for a specific analyte thereafter automatically occurs as the blood first infiltrates the pads 366 and 368 and thereafter makes contact with the surface of the main electrode 360, as explained herein later in greater detail.

Electrode plate 370 is formed of a hydrophilic plastic or of a hydrophobic plastic treated with surfactants to make it hydrophilic. Plate 370 is bonded along its top surface 410 and its side edges to the housing 356 using glue, adhesive, bonding, heat fastening or any other suitable conventional technique.

The plate 370 partly covers the top of the pads 366 and 368 located in rectangular aperture 364 of plate 362 directly below each circular aperture 372 as well as the top surface 412 of plate 362.

The bottom surface 374 of the plate 370 carries the electrodes or conductors 376 and 378 in adhered relation at the locations previously described. Both the plate 370 and the electrodes 376 and 378 are frangible and sever readily when a frangible region 392 is manually broken. Preferably, the conductor 376 and 378 comprise aluminum strips which may be of foil or vacuum deposited metal. Also, the aluminum strip electrodes 360, 376 and 378 are treated for reactivity, as described later in this specification.

Reagent pad-receiving plate 362 is of hydrophobic synthetic resinous material and defines the previously described rectangular apertures 364. Plate 362 is bonded or otherwise suitably secured at the top surface 412 thereof and to the bottom surface 374 of the plate 370. The edges of the side plate 362 are bonded to the housing 356.

Bottom plate 358 is comprised of hydrophobic synthetic resinous material and is bonded or otherwise suitably secured along the surface 414 to the surface 416 of the plate 362. The plate 358 is further bonded or otherwise suitably secured along its side edges to the housing 356 in fluid tight relation. The described bonding of plates 370, 362 and 358 produces an integral and fluid sealed structure, as is illustrated best in FIGS. 7 and 9.

The main frangible electrode 360 is either bonded to or vacuum deposited on the top surface 414 of the plate 358. Electrode 360 extends from midway within the insertion tab 354 through each of the successive sensors 352. The synthetic resinous material from which bottom plate 358 is formed is readily manually frangible, to accomplish the objectives described above. The bottom plate has disposed in surface 414 a pair of grooves extending between each rectangular aperture 364 in plate 362 and an adjacent larger rectangular blind recess 420. The grooves 418 accommodate evacuation of air or other gas from within the associated capillary passageway 386, and the apertures 372 and 364 to accommodate capillary specimen flow, as described above. Rectangular blind recess 420 disposed in the top surface 414 of the plate 358, when disposed at the distal end 72 of the instrument is in communication with the atmosphere, i.e. through lancet opening 422 in the housing 356. See FIG. 10.

As stated earlier, a spring-shaped lancet 384 is confined to the hollow lancet compartment 382 of each sensor 352 of the series packet 350 of sensors 352. The lower portion of each compartment 382 comprises one of the rectangular blind recesses 420 in top surface 414 of the plate 385. The top of each compartment 382 comprises an irregular recess surface 438. The front surface 432 of each compartment 382 is in vertical alignment with the recess 420. The trailing surface 434 is vertically out-of-alignment with the recess 420 forming a shelf or shoulder 436. A portion (the trigger 468) of the spring-shaped lancet 384 rests upon ledge 436. Most of the top surface of 438 of each compartment 382 is disposed within a horizontal plane, with the exception that it is interrupted by a downwardly projecting tab 440, the purpose of which will be later explained. Note that the tab 440 of each lancet compartment 382 is vertically aligned with a recess 442 disposed in the top surface 444 of the housing 356 and with lancet rod 454.

Reference is now made primarily to FIG. 13 for the purpose of describing the spring-shaped lancet 384 which is contained in each compartment 382. The lancet 384, in its illustrated configuration, is formed of a single piece of high strength wire. The lancet comprises a proximal end 450 terminating in a blunt transverse proximal edge 452. Proximal end 450 comprises part of a linear segment or rod 454, which extends along the longitudinal axis substantially the full length of the lancet 384. Linear segment 454 terminates at 90 degree elbow 456, which merges with a reverse direction compression coil 458. The proximal end 460 of the coil merges with a diagonal segment 462 at elbow 464, which has an interior angle of about 45 degrees in respect the horizontal. Diagonal segment 462 merges at elbow 466 with transverse linear trigger portion 468. Trigger portion 468 in turn merges at ninety degree elbow 470 with a distal linear segment 472. Linear segment 472 is parallel to but off-set from linear segment 454. Nevertheless, linear segment 472 is diposed within the interior of the coil 458. Linear segment 472 terminates in a sharp beveled point 474.

Each lancet 384 is placed in its compartment 382 in a cocked position. More specifically, the spring configuration of each lancet 384, when placed in an unstressed state so that distal edge 452 is not contiguous and aligned with the trigger segment 468, due to the memory of the material from which the lancet 384 is made, will cause the trigger 468 to be forward of the proximal edge 452. At the time of manufacture of each lancet 384, the trigger segment 468 is forceably retracted in respect to the rod 454 until the trigger 468 passes the proximal edge 452. The assembler then merely brings trigger 468 into contiguous alignment with proximal edge surface 452, much like cocking the string of an automated bow. See FIG. 13. Note, in respect to FIG. 8 that the trigger portion 468 rests upon the housing shelf 436 and the linear rod portion 454 is adjacent the tab 440 so that the cocked relationship between the trigger 468 and the edge 452 is not inadvertently changed. Thus, the trigger 468 and the lancet tip 474 are restrained from movement by the engagement between the edge 452 and the trigger 468. This retraction of the trigger 468 and the tip 474 is counter to the memory of the material from which the lancet 384 is made. When released, as hereinafter explained in greater detail, the energy contained within the cocked trigger 468 causes the tip 474 to be driven through the hole 422 in housing 356 to penetrate the finger of the medical patient to a predetermined distance adequate to provide a droplet blood sample at the fingertip shortly after lancing. Restated, the spring segment 458 of the lancet 384 is wound in such a way as to permit the inertia of released caused lancet point 474 to overtravel its normal unstressed position to accomplish the aforesaid lancing. After lancing, the memory of the material from which the lancet is formed retracts the lancet tip back into compartment 382.

Prior to use each lancet 384 is located in its associated compartment 382 so that the point 474 is barely contained within the opening 422, in its cocked condition. Thus, the overtravel corresponds to the amount of the penetration desired into the finger. It is to be appreciated that other types of lancets or devices used to pierce a finger of a medical patient may be used.

As previously described, the release/detent assembly 300 comprises a cantilevered spring arm 304 defining a V-shaped downwardly directed projection 308. Projection 308 is disposed below button actuator 116. With assembly 300 properly positioned interiorly of the main assembly 52, button 116 and projection 308 are disposed directly above the unused distal sensor 352 in vertical alignment with the reduced thickness recess 442 of the sensor. See FIGS. 8 and 11.

Thus, when the finger of the patient to be lanced is placed contiguously at the distal edge 402/404 of the exposed sensor in alignment with opening 422, the user merely depresses button 116 to fire the cocked lancet 384 of the distal sensor 352. More specifically, button 116 is depressed manually causing downward deflection of the spring 304 counter to its memory causing projection 308 to first contiguously engage the aligned recess 442 and thereafter to fracture the reduced thickness site 480 (FIG. 8). The fracturing of site 480 downwardly vertically displaces tab 440 which in turn downwardly displaces rod 454 until it is out of alignment with the trigger portion 468 of the lancet 384. This terminates the engagement between trigger 468 and edge surface 452. The memory of the material from which the lancet 384 is made thus displaces the cocked trigger 468 and the rod 472 causing the point 474 to be driven through the opening for 422 and a predetermined distance into the finger of the patient. Once the energy within the lancet 384 has been so dissipated, the memory of the material forming lancet 384 returns the tip 474 to an at-rest position within the compartment 382. In this way a used sensor with a used lancet concealed therein may be safely discarded.

It is to be appreciated that the interior of each sensor is hermetically sealed until the previously used sensor 352 is snapped off. At that point in time the capillary 386 and the lancet opening 422 are exposed for the first time.

As best illustrated in FIG. 6, the insertion breakaway tab 354 comprises the top housing 356, the bottom plate 358, the electrode plate 370, the pad-receiving plate 362, which terminates at edge 500 disposed at about the midpoint at the insertion tab 354. An electrical conductor 502, illustrated as having the same vertical dimension as plate 362, is interposed between edge 500 and a downwardly extending exposed end flange 504 of housing 356, which is sealed to the forward edge of plate 358. The insertion tab 354 also comprises bottom plate 358 and a main electrode 360. Main electrode 360 is illustrated as being in lap electrical contact with conductor 502 but terminating at edge 506 well short of flange 504. Strip electrode 378, but not electrode 376 is extended along with plate 370 so as to be in lap electrical contact with conductor 502. Conductor 378 terminates at edge 508, well short of flange 504. The electrical interconnection of electrodes 360 and 378 across conductor 502 accommodates issuance of an audible signal when the packet 350 of sensors 352 is properly inserted into the instrument through the distal opening 124, as hereinafter explained.

The breakaway insertion tab 354 is primarily formed from frangible plastic. When the sensor packet 352 is initially and correctly inserted through the opening 124 into the chamber 244, electrical contact between conductors 262 of assembly 260 and the electrodes 378 and 360 is established. The electronics of the instrument, as hereinafter explained, measure the resulting current flow through conductor 502. The value of this current flow is factory set and is related to lot-to-lot variations found in sensors fabricated in accordance with the present invention. This value is read by the instrument and used, as explained later, to adjust the internal calibration of the instrument. This value remains in the instrument memory until updated by the current flow factor of the next sensor packet 350. When the breakaway insertion tab 354 of a packet 350 is snapped off prior to utilization of the first sensor 352, current flow between the electrodes 378 and 360 across conductor 502 stops. Note, that the illustrated packet embodiment of FIG. 5 depicts the packet 350 of sensors 352 such that the sensors are numerically identified in succession (i.e. 1, 2, etc.) so that the user will visually know how many sensors have been used at any one point in time.

One of each of the spring conductors 262 is in electrical communication with the respective electrodes 360, 376 and 378, when the distal tab 278 is properly physically interconnected, at recesses 276 with projections 278 of the slider/contact assembly 260. This union is diagrammatically illustrated in FIG. 12, in exploded relation. Any suitable approach may be used by which the electrodes 376, 378 and 360 are placed in electrical communication with the electronics 336 of the instrument 50. For example, one suitable method is to simply extend each electrode contained within the packet of sensors passed the proximal end of the housing 356 so that the spring contacts 262 simply slip over the protruding electrodes.

Figures 12, 12A:
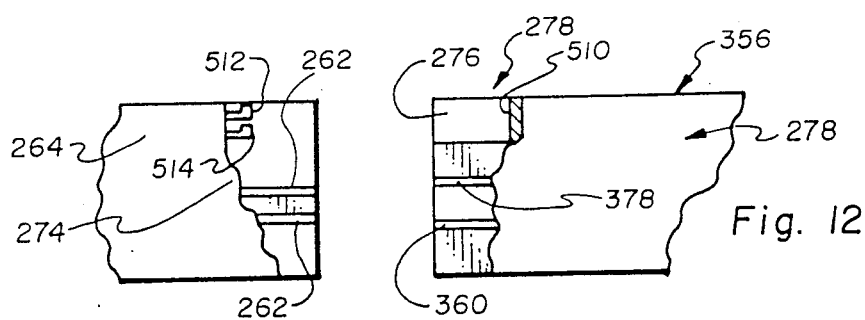
FIGS. 12 and 12A are fragmentary side elevational views schematically illustrating one way in which the sensor strip of FIG. 5 is placed in selected electrical contact with electronics components of FIG. 1.

With reference to schematic FIG. 12, a small conductive strip 510 is bonded to the proximal end of the housing 356 at the base surface of the slots 276. Conductor 510 is disposed opposite to a pair of L-shaped, spaced contacts 512 and 514 carried by the plate 264. Conductivity between contacts 512 and 514 through conductor 510 is achieved when the sensor packet is fully inserted into the chamber 244 and joined with the assembly 260. At this time, when electrodes 512 and 514 are in contact with conductor 510, an audible signal is issued informing the user that the sensor packet 350 has been correctly inserted into the instrument.

Assuming the instrument 50 to exist with the chamber 244 empty, either because the instrument 50 has not been used previously or because a prior packet 350 of sensors 352 has been used and removed, the instrument is loaded with sensor packet 350 by first removing the cap 58 from the main assembly 52, thereby exposing the opening 124 to the chamber 244. Disposable sensor packet 350 is linearly inserted manually through the opening 124 into the chamber 244, proximal end 278 first, with the snap-off grooves 390 face up. The side wall 240 of chamber 244 and the bias of spring 310 cause proximal tab 278 to be aligned with plate 264. The packet 350 is pushed all the way into the chamber 244 until the projections 274 fully engage the recesses 276 and electrical contact is respectively created between the electrodes 376, 378 and 360 and the spring contacts 262, whereby the electrodes are placed in electrical communication with the electronic components 336. Contact between conductors 512 and 514 across conductor 510 sounds a signal confirming proper insertion of the packet 350. When fully inserted, the breakaway distal insertion tab 354 is exposed. Also, approximately ¼ of one inch of the number one sensor 352 is projecting out of the slot 122. The breakaway insert tab 354 is manually snapped off at the point in time when the user desires to immediately thereafter use the number one sensor 352. The breaking away of the insert tab 354 exposes for the first time the capillary passageway 386 at opening 400 as well as the lancet aperture 422 of No. 1 sensor 352.

To use the instrument to quantitatively detect the amount of a predetermined analyte in a droplet sample of blood, for example, the instrument is removed from the pocket of the user or from its storage location. The hinged lid 134 is positioned in its opened condition, as illustrated in FIG. 3, and the wick 132, containing disinfectant, is used to sterilize the fingertip to be lanced. Thereafter, the lid 134 is returned to its closed position.

The entire cap 58 is next removed from the main assembly 52. This exposes either the tab 354 at slot 122 or the edge 402/404 of a used sensor 352 at the same location. In the event the tab 354 remains, it is snapped off, as described above. Where a used sensor 352 is exposed at edge 402/404, the used sensor is manually grasped and pulled forward until the disposable sensor packet 350 is indexed along detent plate 310 to the next unused sensor.

As can be seen in FIG. 11, the indicated indexing is controlled by the detent plate 310 and its detent 312. More specifically, each sensor packet 350 comprises one side edge 529 having spaced vertical notches 530 disposed therein in alignment with the notches 390 and 394 heretofore described. The detent plate 310 is disposed so that it cantilevers from front to rear. The at-rest position of detent plate 310 is such that, in the absence of a sensor packet 350 in the chamber 244, detent 312 extends somewhat into the travel path used by the packet 350 when inserted and removed. Thus, when a packet 350 is inserted, the detent plate 310 is deflected transversely away from the displacement path of the packet. The memory of the material from which the spring plate 310 is made urges the detent in the direction of the notched edge surface 529 of the packet 350.

Thus, as the packet 350 is displaced, the detent 312 rides along the notched edge 529. When the packet 350 is fully and correctly inserted, the detent 312 becomes biased contiguously and forcefully in the side V-shaped notch 530 between the insertion tab 354 and number one sensor 352. This constrains the packet 350 against inadvertent displacement.

When one is preparing to engage in a further analyte test, as mentioned, a used sensor protruding from the slot 122 is manually grasped and pulled axially and distally away from the slot 122 with a manual force exceeding the force of the detent 312 in engagement with the aforesaid side notch 530. The packet 350 is thus manually indexed forward with the detent 312 riding along the side 529 of the packet 350. When the detent 312 is in alignment with the next notch 530, it snaps under the force of its memory or bias into the notch 530, creating a greater resistance to continued displacement and sometimes producing an audible sound. At this point, the user discontinues packet displacement and snaps off the used sensor 352, safely disposing of the same, including the concealed lancet and any disease or contamination contained within the chamber 380 of the used sensor. The snapping off of the used sensor exposes the previously concealed and uncontaminated capillary 386 and lancet opening 422 at the distal edge 402/404. This also breaks all electrodes at the edge 402/404.

Thereafter, lancing of the fingertip occurs, as explained above, by depressing the actuator 116 thereby firing the precocked lancet tip 474, which pierces the skin and subcutaneous tissue of the patient. Typically, the fingertip is gently squeezed to produce a minimum 15 microliter sample of blood as the droplet specimen. The capillary opening 386 is touched to the droplet of blood and the blood specimen is aspirated through the sensor, as described above, the conductive bridge formed by the specimen between electrodes 376 and 378 is sensed by the software of the microcontroller (microcomputer) which in turn issues an audible "beep" indicating sufficient blood has been aspirated through the capillary tube 386 to connect the electrodes 376 and 378.

Thereafter, through reactions and interactions occurring within the pads 366 and 368 and at the surface of the aluminum electrode 360, the analyte testing proceeds automatically with the results being displayed at the LCD 68, typically within one-half to five minutes.

The LCD 68 is preferably of limited character length where the characters are of large enough size so that the sight-impaired can visually determine the results of the test. Preferably, something on the order of 60 tests, with time and date of each test and the results thereof for a given patient can be stored in the memory of the instrument itself, as explained hereinafter.

Each assay requires its own specific customized sensor and the instrument to be used with any specific custom sensor is keyed to the sensor so that incorrect sensors may not be used, as mentioned above.

The actuation of the lancet activates the measurement portion of the instrument, as explained later.

A short time after the liquid sensing "beep", a second audible signal, having a different sound pattern, is generated by the microcontroller software and emitted by the instrument, indicating completion of the assay and availability of the results.

Even though the electronics and data processing and storage portion of the instrument have not yet been described in detail, it will be helpful at this time to explain some of the functional features of the instrument 50.

The instrument 50 provides a variation in data review different than the result presentation described above. Assay results for many days, with the time and date of each assay, are stored in a cyclic buffer in the instrument's microcomputer memory. The data may be sequentially reviewed by the user by sequential actuation of button actuators. Another sequence is used to initiate a calibration cycle, when on-site calibration is appropriate. Combinations of depressions of the buttons can also be used to set the time or date or to send information to a remote personal or other computer. The buttons preferably operate in a manner similar to the control settings on a digital watch. In emergencies and/or under direction of a physician, the user can send the stored information automatically to the physician's computer.

This is conveniently accomplished by dialing the physician's office computer number via a telephone or communications link and listening for the tone. Upon hearing the tone, the instrument is held near the mouth piece portion of the phone. Appropriate button depression will send an audio signal to the physician's computer for data acceptance, storage and processing there.

The instrument 50 is designed for used in the home, doctor's office, work place, and at bedside. Instrument 50 is specifically meant for use in screening or monitoring, as opposed to diagnostic applications. Instrument 50 measures directly in whole blood and is for immediate, finger prick, at-patient analysis.

The instrument 50 is a self-contained on-site test laboratory and determines the concentration or relative concentration of a specific analyte, requiring only two or three operator steps.

The test results are preferably displayed as analyte concentrations in standard or international units, preferably selectable by the operator.

The instrument 50 comprises a piezo electric transducer directly connected to the microcontroller which outputs a sequence of activating electrical impulses at preprogrammed frequencies to provide the aforesaid status "beeps". The same transducer is activated by the microcontroller to provide tones for acoustic coupling of data to be sent from the instrument 50 to a receiving computer through telephone or communication links.

The instrument 50 has a one-way communication link into the microcontroller through the disposable sensor connections to allow new program, test program and data down loading to the microcontroller from a personal or other computer. This is accomplished through an appropriate interface outside the instrument which connects the instrument to a computer. The loading information will most often be calibrating standard curves or programs for designed sample disposables in the field. This link will be used in the factory to download programs. The other direction communication link outward from the instrument is through the audio generator.

The microcomputer of the instrument 50 has adequate power to acquire and process the signal from the sensor in real time. It is able to recognize the initiation of the signal and perform pattern recognition on the incoming signal at a rapid enough rate to determine the beginning and end of the sample waveform in real time. The microcomputer controls the following: memory including extended RAM, A/D converter, multiplexing circuits, keypad entry decoding, liquid crystal display, two way communications circuits, 300 BAUD audio output, and disposable sensor signal processing.

Sufficient RAM is provided to store a large number of samples of data, including date and time. Also contained in the memory is the instrument number, disposable sensor identifying resistance value, and analyte type. The RAM also contains a standard curve look-up table, current time and date, and other instrument status and scratch pad information. ROM and EEPROM provide storage for subroutines and programs.

The A/D converter is preferably eight bit (1:256).

The instrument microcomputer is capable of addressing eight analog channels, against one common lead. It has digital input channels, which interpret the status of the keys (actuators).

Push button keys or actuators are decoded and available for Mode at 118, Trigger at 116, and Set at 112 operations. Another released button 114 is not currently used, but has been reserved for future expansion in instrument control functions. Set is preferably a recessed key. The Mode switch initiates the data review and transmission modes. Other than the Trigger switch, the Mode key is preferably the only easily depressed and activated key/pad entry. The Trigger switch, shown in FIG. 2 just above plate 320, to clarify its position relative to notch 322, assembly 300 and button 118, is carried by the circuit board 332. The Trigger switch is a magnetic reed switch S3, activated, as hereinafter explained in greater detail, by depression of the button 116, which moves magnet 301 away from proximity of the reed switch S3 to momentarily close the normally closed switch S3 to cause commencement of the electronic test cycle.

The display 68 is preferably 16×84 pixels. It has other addressable display flags or enunciators, clock functions, units of measure for graphics, alarm set, etc. It is directly addressed by the instrument microcomputer. The character size is preferably at least 0.7 cm high.

A downloading digital interface uses the disposable sensor contacts. Using a conventional interface box, the instrument is able to receive data from one or more other computers, preferably at 300 BAUD rates. Under controlled conditions, it may be used to remotely upgrade the operating systems, calibration data, measured unit selection, and other applications programs.

A audio output is preferably via a piezoelectric transducer. It is buffer-driven and frequency-programmed by the instrument microcomputer. Its range is preferably at least 500 to 2500 Hertz. The volume is programmably variable, with a maximum loudness such that it can be heard in a quiet room at a distance of twenty feet and is able to transmit to standard 300 BAUD modems over standard dial-up telephone lines. The transmitter is used for user enunciator functions and for 300 BAUD telephone data transmission functions. It is also used for alarm indication. The audio volume is program variable via one of the instruments modes.

The computer processes up to three signal channels including the liquid detector, three switch inputs and battery voltage monitor.

Twelve and twenty-four hour clocks are provided. A crystal oscillator is used to provide time accuracies equivalent to that of a quartz watch. The time and date are recorded for each sample preferably to the minute. The date and time are displayed separately. When the instrument has not been in use for a short time, such as 5 minutes, the display defaults to a time of day display. An alarm mode is provided which allows the setting of the alarm on a time of day basis, to remind the patient and/or medical attendant to engage in further testing, for example.

The instrument has limited self test capability, which runs each time a lancet is triggered. It tests the electronics and connection of the disposable sensor and determines calibration constants when a new sensor packet has been inserted, before insertion tab 354 has been removed. The system also has an internal program which allows automatic final testing of the instrument by using disposable sensor connections and access to the keys, display, and mechanical release mechanism by the test fixture. The same keying mechanisms used to assure use of proper disposable sensor type are used by the tester to assure use of the correct final test.

A positive maneuver is provided to trigger the lancet firing mechanism. It is so positioned and requires sufficient force to assure the user that it will not be triggered inadvertently. Penetration and withdrawal velocities of the lancet are sufficiently rapid that it will be found to be substantially pain free. The depth of penetration is preferably between 2.0 and 4.0 mm.

The description of the mode selection and button utilization is presented later in the electronics section.

The data preferably will be presented in a tri-sequence defined below.

All test results (up to a certain number of samples) over the past several weeks are shown as bar graphs, with the current day of the week being included. The data are divided into four six hour periods for each day and presented as adjacent bars for each day. The high and low limits of the normal range of each assay are shown as two horizontal lines on the graph. If two or more tests are taken in the same period, an average value of the tests is presented. The days of the week are, for example, fixed position labels indicium to cover 60 at the bottom of the graph, requiring three weeks of data space be available. The graph shifts on the display to show a minimum of fifteen days, beginning with the current day of the week.

The display parameters for any six hour period may be shown without those of other periods, graphed the same as those for all test results, except only one bar per day is graphed.

After the graphical display sequence is complete, the time display program is reentered. If a length of time, such as five minutes, elapses between button depressions, when the instrument is in the review mode, the display is returned to the time display mode. The review mode is also interrupted by exercising the lancet firing arming mechanism, thereby initiating the sampling routine.

A resistor at 502 (FIG. 6) is preferably placed between the liquid level sensor leads in the insertion tab 354 to indicate calibration values for the disposable packet 350. The value of that resistor is determined using the A/D converter at the time of first insertion of the disposable packet 350. The resistance value is used as an addressing function to select the preselected stored standard curve to be used.

All test results will be presented as analyte concentrations. The signals from the disposable sensor contact shall be processed in a manner which requires no interaction with the operator. If desired, the time-to-result is displayed as a "countdown" or as a series of graphical dot or line pattern changes while processing is in progress. The processing is divided into real time pattern recognition and data reduction and storage. The real time pattern recognition process determines the effective start of the signal, performs any real time filtering and real time data reduction required, and determines the end of the data access cycle. The subsequent processing is preferably completed in less than 10 seconds. The final test results, date, and time of the test are stored in the test cyclic buffer and measured concentrations are displayed with units of concentration.

Quantitative Analyte Detection in Sensors

The foregoing description of the preferred embodiments of FIGS. 1–15 relates to a chain or packet of sensors of a definitive configuration. The present invention, however, embraces insertion and use of a single disposable sensor into the test instrument and variations in configurations. The ensuing description, directed to FIGS. 16–22, illustrates single sensors having configurations which vary in configuration but not in principle from the sensor embodiment of FIG. 1–15.

In all illustrated configurations, each sensor functions to ascertain the quantity of a predetermined analyte in a whole blood or other liquid sample, accurately and automatically using a hand-held instrument and a droplet-sized sample. Each sensor is stored dry, producing an expected minimum shelf life preferably of two years. While a number of whole blood analytes are of interest and within the scope of the present invention, glucose is of particular interest. There are approximately 6 million known diabetics in the United States and it is estimated that there are 7 million undiagnosed diabetics as well. The number of known U.S. diabetics grows annually at about the rate of 500,000. Diabetic testing commonly occurs in the home and at doctor's offices. Prompt, accurate and error free glucose test results are available using the sensors herein disclosed and the remainder of the associated instrument.

Broadly, a mercury tracer site is infiltrated by a test analyte of unknown presence and quantity within the liquid sample. The term mercury as used herein generally refers to mercury as a salt, and/or in an ionic form, and/or in a chelated state, etc. Thus, the mercury, as a label in the tracer, may be present as a mercuric salt or mercuric ion and the term "mercury" as used herein encompasses such a mercuric salt and/or ion. Competitively the tracer is released as a function of the quantity of the test analyte. The released mercury tracer is displaced by or within the liquid of the specimen to a site where reagent is available by which mercury, in ionic or salt form, from the released tracer is freed. The released mercury is transported by or within the liquid of the specimen to the surface of an aluminum body, where the released mercury interacts with said surface, measurably changing the characteristics thereof.

Reference is now made to FIGS. 16 and 17, which illustrate a sensor 552, in accordance with the present invention. Sensor 552 is comprised of a housing 570. Electrical connections 602 are illustrated as protruding from the one end 600 of housing 570. See FIG. 17. The electrical connections 602 are electrically connected as hereinafter explained in greater detail for determining the amount of analyte present. Extending from a second opposed end 604 of housing 570 is capillary tube 614 having an inlet opening 616.

A sample suspected of containing an analyte enters inlet opening 616 of capillary tube 614. The sample may be a body fluid, such as blood, cerebral spinal fluid, or urine. The sample travels upwardly through tube 614 by capillary movement. When the sample reaches and bridges the ends 623 and 625 of electrodes 621 and 622, which are connected to the electrical connections 602, the instrument to which the sensor 552 is connected emits an audible sound which indicates that a sufficient volume of sample has entered the sensor. Thus, the capillary tube size and electrode spacing is selected to require sufficient liquid volume in the specimen to trigger the initial signal and permit an accurate analyte test. The sample, therefore, acts as a conducting medium between electrodes 621 and 622, at the distal ends 623 and 625, which ends are exposed at the proximal end 617 of capillary tube 616. Electrode 621 also serves as a positively charged electrode of the sensor. Electrode 622 serves only as the negative electrode during the described liquid sensing phase. The sample then contacts a thin distributor pad 618 which spreads the flow of sample evenly across a tracer material pad 620.

The sample passes through distributor pad 618 and contacts a thin tracer pad 620. Tracer pad 620 is made of a material which permits or facilitates capillary flow of the sample through the tracer pad. Tracer pad 620 contains the tracer, which may be a graft copolymer of polyethyleneimine and polyethylene glycol having a mercury label, said copolymer also being attached to an appropriate ligand. The ligand used is dependent on the type of assay employed and the analyte being assayed. In a preferred embodiment, tracer pad 620 also contains a binder for analyte as well. In alternative embodiments, not shown, the tracer and binder may be on separate pads, the disposition of which being dependent upon the type of assay employed.

The tracer contained in tracer pad 620 should be soluble in the sample; for example, water, blood, serum, urine, and cerebral spinal fluid, etc. It also should be mobile in these liquids in order to insure that tracer contacts appropriate reagents. The tracer should, when a competitive assay is being employed, allow the ligand to remain chemically active and able to compete predictively with target analytes for a specific binder.

When a binder is contained on tracer pad 620, it is contemplated, in the present configuration, that the binder is not covalently attached to the tracer pad 620, but that the interaction between the binder and the tracer pad prevent the binder from leaving tracer pad 620.

Contact of the sample with tracer pad 620 thus sets in motion the assay process. Analyte, if present, competes with the tracer to release an amount of tracer which is a function of the analyte concentration. The released tracer, containing the mercury label, is freed to move from the tracer pad 620 to the releasing reagent pad 624, which releases mercury ions from the tracer. As tracer is released from tracer pad 620, the tracer and sample move upwardly through the sensor and contact releasing reagent pad 624. The pad 624 is preferably impregnated with a nickel salt, most preferably nickel chloride and ammonium chloride. Releasing reagent pad 624 is also made of a material which will facilitate capillary flow of the sample through releasing reagent pad 624. As the sample and tracer contact the reagent pad 624, the nickel chloride releases mercury ions from the tracer.

After the mercury is released from the tracer upon contact with reagent pad 624, the mercury ions contact a negatively charged electrode 626, which is also connected to electrical connectors 602. Electrode 626 is made of aluminum with a surface film of aluminum oxide/hydroxide plus surface-modifying agents. Upon contact with electrode 626 by mercury released from the tracer by releasing reagent pad 624, the mercury and aluminum surface interact eventually forming a mercury-aluminum product. Such reactions may occur at room temperature which results in changes which occur on the surface of the electrode 626.

In a preferred embodiment, the positive and negative electrodes are operated at about 0.2 volt. In general, the system, as presently configured, should not be operated at above 0.5 volt. In general, the positive electrode is smaller than the negative electrode. In a preferred embodiment, the positive electrode is also formed from aluminum.

The electrode 626, as above stated, has a barrier or protective surface layer, of aluminum oxide or $Al_2O_3$. When water is present, as during electrode surface modification, an additional porous $Al(OH)_3$ layer forms on the $Al/Al_2O_3$ layer. The mercury, upon contact with the electrode 626, interacts or reacts with the surface of the aluminum electrode to destabilize the protective oxide/hydroxide layers and eventually form a mercury-aluminum amalgam. The changes produced by or leading to the formation of the amalgam are measured, preferably electrically. The changes which can be measured include electrolytic changes, resistance changes, and capacitance changes. The measurements of these changes in the electrode properties can be used to determine the amount of analyte present in the sample being assayed.

Also contained in the sensor is vent hole 628. Vent hole 628 is positioned at the region where flow of sample occurs in the sensor, between releasing reagent pad 624 and electrode 626. Vent hole 628 provides for the release of air and/or gas so that the flow of the sample will not be impeded.

The pads employed in the sensor are those capable of holding the particular reagent and which induce or permit capillary flow. The pads may be formed from a porous material and as representative examples there may be mentioned porous paper, wettable cloth (woven and non-woven), porous hydrophilic plastics, etc.

The reagents may be simply soaked or dispensed onto the pad then oven dried, as in the case of the releasing agent. In the case of binder and/or tracer, the reagent may be applied to the pad and lyophilized. In the case of a binder, in some cases it may be necessary to bond or covalently attach the binder to the pad, rather than simply soaking the pad with the binder.

Instead of using a pad for supporting the binder and/or tracer, such reagents could be included in a capillary tube or other support capable of inducing flow. For example, tracer may be lyophilized on the interior wall of a capillary tube, and a sample introduced into the tube for subsequent flow and contact with a binder.

Figure 18:
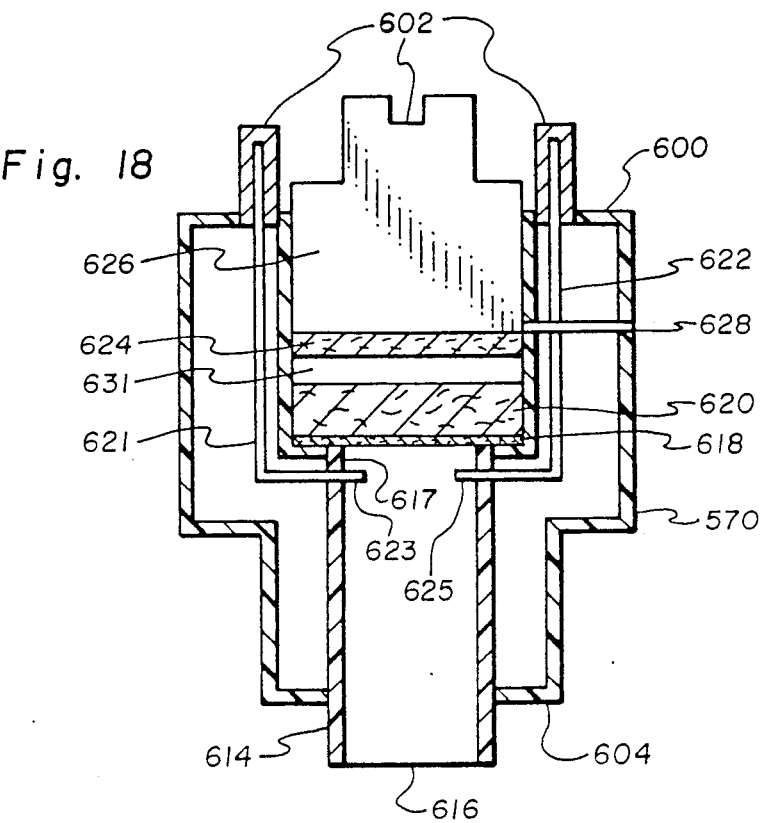
FIG. 18 is a cross-sectional view of another embodiment of a sensor in accordance with the present invention, showing a space between a tracer pad and a releasing reagent pad which releases mercury.

In one alternative embodiment, shown in FIG. 18, a sample enters inlet opening 616 of capillary tube 614, and travels upwardly through tube 614 by capillary movement. The sample then contacts and bridges electrodes 621 and 622 at distal ends 623 and 625, which electrodes are connected to the electrical connections 602. Electronics of an instrument to which the sensor is connected emit an audible sound, as explained hereinafter, when a sufficient volume of sample has entered the device so as to electrically connect ends 623 and 625. Electrode 621 also serves as a positively charged electrode of the sensor. The sample then contacts spreading pad 618 of the sensor, which spreads the flow of sample evenly across tracer pad 620. The sample contacts and is absorbed into tracer pad 620 which also includes binder for the analyte, which starts the assay process as described above, whereby analyte and tracer compete to release an amount of tracer as a function of the analyte concentration.

Disposed between tracer pad 620 and releasing reagent pad 624 is a space 631. Space 631 enables the device to be programmed so as to allow the sample and tracer to undergo an incubation period for a predetermined time. The predetermined incubation time allows for more control of the flow of the free tracer into the releasing reagent pad 624, and the subsequent generation of a more consistent signal from the device upon the release of mercury.

At the end of the predetermined incubation period, the device becomes compressed so as to enable tracer pad 620 and releasing reagent pad 624 to contact each other, thus enabling the flow of sample and tracer from tracer pad 620 to releasing reagent pad 624. Releasing reagent pad 624, which is impregnated with salt, such as nickel chloride and ammonium chloride, enables the mercury to be released from the tracer. The mercury then contacts negatively charged aluminum electrode 626, whereby the mercury interacts with the aluminum surface and changes at the surface of the aluminum electrode are measured electrically. The sensor also contains a vent hole 628 which is positioned between releasing reagent pad 624 and electrode 626 so as to provide for the release of air and/or gas from the device.

Figure 19:
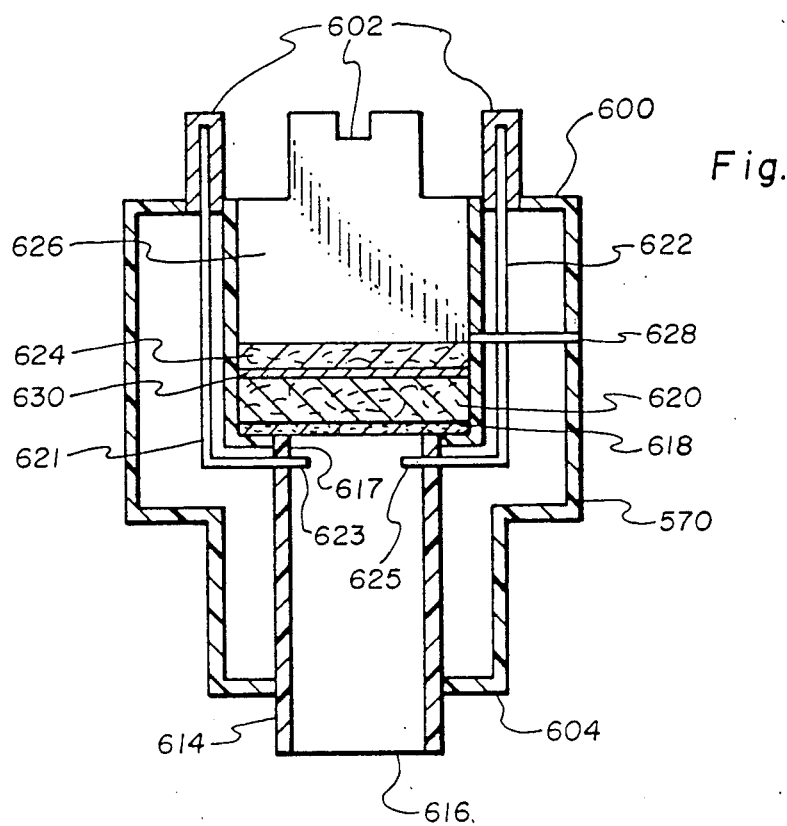
FIG. 19 is a cross-sectional view of still another embodiment of a sensor in accordance with the present invention depicting a water-soluble membrane between the tracer pad and the releasing reagent pad.
Figure 20:
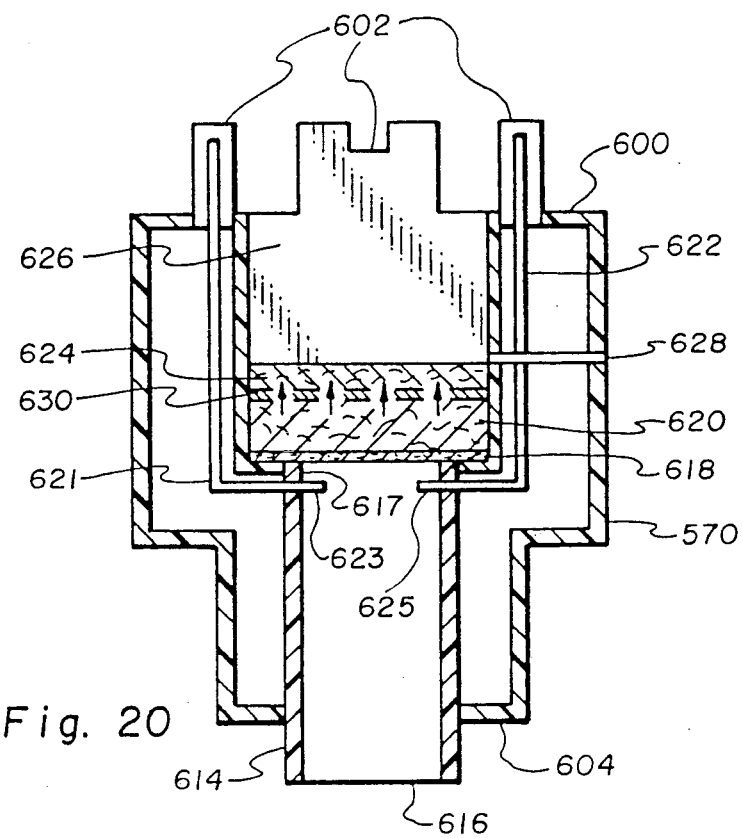
FIG. 20 is a schematic view depicting the operation of the sensor shown in FIG. 19.

Another alternative embodiment, shown in FIGS. 19 and 20, depicts a sensor having a water-soluble membrane 630 disposed between tracer pad 620 and reagent releasing pad 624. In this embodiment, a sample enters inlet 616 of capillary tube 614. The sample then contacts bridging electrodes 621 and 622 at distal ends 623 and 625, which are connected to the electrical connectors 602, which detect an adequate volume of sample within capillary tube 614 as described above. The sample then contacts spreading pad 618, which spreads the flow of sample evenly over tracer pad 620.

The sample then contacts tracer pad 620 which also includes binder for the analyte, whereby tracer is released into the sample as described above. Sample and tracer flow through tracer pad 620 by capillary flow.

The sample and tracer move through tracer pad 620 until the sample and tracer contact water soluble membrane 630. Membrane 630, as shown in FIG. 20, dissolves gradually upon contact of the sample and tracer. Membrane 630 is of a thickness such that it dissolves after a predetermined time period. Once membrane 630 is dissolved, the sample and tracer then contact releasing reagent pad 624. Membrane 630, therefore, provides for a limited time sample flow separation between tracer pad 620 and releasing reagent pad 624, thereby providing a predetermined incubation time of the sample and tracer within the tracer pad 620, the advantages of which have been described above.

Upon contact of the sample and tracer with releasing reagent pad 624, mercury is released from the tracer, and then contact aluminum electrode 626, whereby the mercury eventually amalgamates with the aluminum, and changes at the surface of the electrode are measured, preferably electrically as described.

Also positioned within the sensor is vent hole 628, which provides for the release of air and/or gas from the interior of the sensor, as described above.

Figure 21:
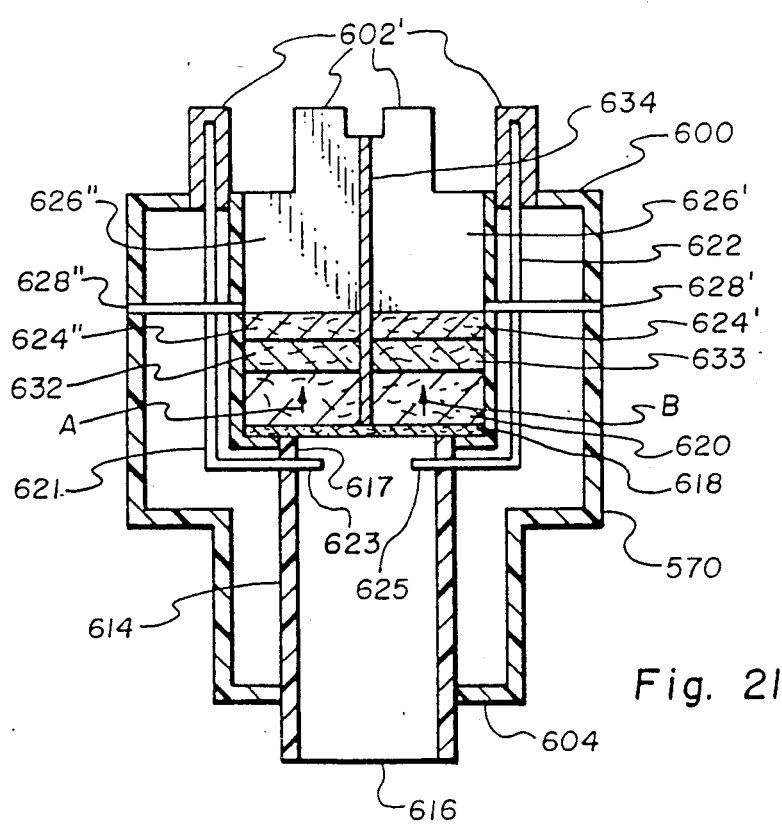
FIG. 21 is a cross-sectional view of an additional embodiment of a sensor in accordance with the present invention, showing a pad which contains a known amount of mercury ion.

FIG. 21 depicts an embodiment, which is known as a self-referencing sensor. A sample enters inlet opening 616 of capillary tube 614 and travels by capillary flow, as described above. The sample then contacts bridging electrodes 621 and 622 at distal ends 623 and 625. Electrode 621 is a positive electrode analogous to electrode 621 shown in FIG. 17. Electrodes 621 and 622 are connected to electrical connectors 602'. When a sufficient volume of sample has entered the sensor, an audible sound is emitted, as described above. The sample then contacts spreading pad 618.

As the sample moves by capillary flow through spreading pad 618, the flow of the sample is divided into two flow paths, A and B, by impervious divider 634. In flow path A, the sample flows from spreading pad 618 and contacts tracer only pad 632. Since tracer only pad contains no binder, the flowing sample dissolves all the tracer present in the pad. The sample flows through tracer only pad 632 and then contacts releasing reagent pad 624", which releases mercury ions from freed tracer, as described above. The released mercury ions then contact aluminum electrode 626"' and eventually amalgamate with the aluminum. Changes at the surface of the electrode 626" are then measured electrically.

Along flow path B, the sample leaves spreading pad 618 and contacts tracer pad 633 which also contains binder for the analyte, whereby tracer is released from the tracer pad 633 as described above. The sample plus tracer flows by capillary action into releasing reagent pad 624', which releases mercury.

The released mercury ions then contact aluminum electrode 626', whereby the mercury eventually amalgamates with the aluminum and changes of the surface of electrode 626' are measured electrically. The two flow paths, A and B, therefore, provide for an internal calibration or reference of the changes generated by the eventual amalgamation of mercury with the aluminum surfaces of electrodes 626" and 626'. This comparison may then be used to determine the presence and/or amount of analyte in the sample.

Also present are vent hole 628''', along flow path A, and vent hole 628', along flow path B, which provide for release of internal air and/or gas from the sensor, as described above.

A self-calibrating device is shown in FIG. 22. A sample enters the device through inlet 716 of capillary tube 714. The sample moves through tube 714 by capillary movement and contacts bridging electrodes 721 and 722 at 623 and 625, which are connected to electrical connectors 702. Electrical connection of the electrodes by the liquid sample cause an audible sound to be emitted when a sufficient volume of sample has entered the device.

After the sample has entered tube 714, the flow of the sample is divided into two flow paths, C and D, by impervious divider 732. In flow path C, the sample contacts spreading pad 718, which evenly distributes the sample for contact with blank pad 730. Blank pad 730 has no chemical function, but serves to balance the time flow of the flow paths. The sample in flow path C travels by capillary flow through blank pad 730 and then contacts tracer pad 720 which also includes binder for the analyte, which releases tracer into the sample, as hereinabove described. Sample and released tracer travel through tracer pad 720 by capillary flow, and then contact releasing reagent pad 724, which releases mercury ions from the released tracer, as explained. The mercury ions then contact aluminum electrode 726, whereby the mercury eventually amalgamates with the aluminum surface and changes in the surface of the electrode are measured electrically, as hereinabove described.

Along flow path D, the sample contacts spreading pad 718', which spreads the sample evenly upon pad 731. Upon contact with pad 731 by the sample, pad 731 releases a known concentration of analyte to the sample. The sample and the known concentration of analyte flow through pad 731 and contact tracer pad 720' which also includes binder for the analyte, which upon contact with the sample and known concentration of analyte, releases free tracer into the sample, as hereinabove described.

A dual assay sensor is represented by FIG. 22. In this embodiment two separate assays may be performed simultaneously. Flow path C, composed of electrode 721, wetting pad 718, tracer pad 730, mercury releasing pad 724, vent hole 728 and main electrode 726 operate to perform assay number 1 as previously described. Pad 720 serves no purpose in this embodiment and may simply be considered an extension of tracer pad 730. Flow path D, composed of electrode 722, wetting pad 718', tracer pad 731, mercury releasing pad 724', vent hole 728' and main electrode 726' operate to perform assay number 2. Pad 720' serves no purpose in this embodiment and may simply be considered an extension of tracer pad 731. Each pathway contains reagents specific for the intended assay. Electrode 721 and 722 function as sample detection electrodes on ends 623 and 625, as previously discussed. It is appreciated this embodiment, while describing a dual assay sensor, may be expanded with incorporation of additional assay flow paths to encompass performance of multiple simultaneous assays.

The sample and free tracer, travel through tracer pad 720' by capillary flow and contact releasing reagent pad 724', whereby mercury ions are released from the free tracer, as described above. The mercury ions then contact aluminum electrode 726', whereby the mercury eventually amalgamates with the aluminum surface, and changes at the surface of electrode 726' as a result of the interaction and amalgamation are measured electrically. The presence and/or amount of analyte in the sample is determined by comparing the measured changes at the surfaces of the electrodes 726 and 726' by electrical measurement.

Also contained within the device is vent hole 728, along flow path C, and vent hold 728', along flow path D, which provide for the release of air and/or gas from the device, as hereinabove described.

Figure 23:
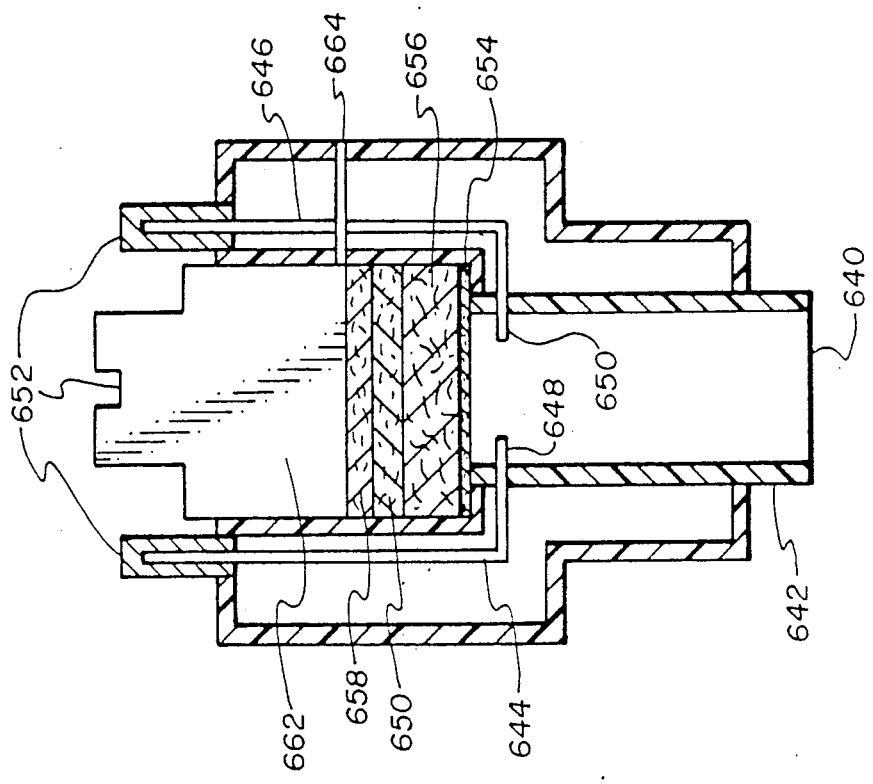
FIG. 23 is a cross-sectional view of a further sensor embodiment.

In one alternative embodiment, shown in FIG. 23, a sample enters inlet opening 640 of capillary tube 642 and travels upwardly through tube 642 by capillary movement. The sample then contacts and bridges electrodes 644 and 646 at exposed distal ends 648 and 650, respectively. Electrodes 644 and 646 are connected to the electrical connections 652. An audible sound is emitted when a sufficient volume of sample has entered the sensor. Electrode 644 also serves as a positively charged electrode of the sensor. The sample then contacts spreading pad 654 of the sensor, which spreads the flow of sample evenly across tracer pad 656. The sample contacts and is absorbed into tracer pad 656 which also includes binder for the analyte, which starts the assay process, as described above, whereby analyte and tracer compete to release an amount of tracer which is a function of the analyte concentration.

Disposed between tracer pad 656 and releasing reagent pad 658 is a mercury-containing substrate pad 660. Sample and tracer flow into mercury containing substrate pad 660 by capillary action. The tracer, in this embodiment labeled with a mercury copolymer releasing agent, most preferably an enzyme, causes cleavage and/or release of mercury copolymer containing substrate subunits, which dissolve into the sample present in the mercury-containing substrate pad 660. The liquid contacts releasing reagent pad 658 resulting in liquid flow from mercury-containing substrate pad 660 to releasing reagent pad 658. As hereinabove described the enzyme label may be alpha-amylase, the substrate may be insoluble amylose (which is cleaved by alpha-amylase) to which is attached mercury containing copolymer of the type hereinabove described. Releasing reagent pad 658, which is impregnated with a salt such as nickel chloride and ammonium chloride, enables mercury to be released from the soluble substrate subunits. The mercury then contacts negatively charged aluminum electrode 662, whereby the mercury interacts with the aluminum surface and changes in the surface of the aluminum electrode are measured electrically. The device also contains a vent hole 664, which is positioned between releasing reagent pad 658 and electrode 662 so as to provide for the release of air and/or gas from the device.

The examples contained herein are by way of example only and it is understood combinations arising therefrom are within the scope of these teachings. For example, an enzyme tracer-substrate system may be used in conjunction with water soluble membranes or deformable spaces to provide for controlled incubations (sample-tracer and/or tracer-substrate) and for self-referencing and/or self-calibrating features.

Although it is preferred that analyte be determined by electrical means resulting from mercury-induced protective surface film destabilization on the electrode surfaces, it is also contemplated that the presence and/or amount of analyte may be determined by other means resulting from mercury-induced protective surface film destabilization. These include heat generated from the exothermic reaction between unprotected aluminum and its environment, measurement of the change of mass of unprotected aluminum and its environment, and optical or visual quantification of surface reflectivity or other surface changes resulting from reaction between unprotected aluminum and its environment.

The preferred embodiments are not limited as hereinabove described, and changes may be measured other than by electrical means.

Thus, for example, a thin layer of aluminum (for example, a few atoms thick) may be deposited on a transparent support (such as glass or plastic) and a change in reflection from the aluminum surface resulting from interaction with mercury released from bound and/or unbound tracer may be determined.

The change in reflectivity is a result of mercury interaction and destabilization of the protective films present in the aluminum surface. Without the protective surface films, the aluminum reacts rapidly with its environment, in this case the water present in the sample. The reflectivity of the aluminum therefore changes rapidly due to changes in aluminum layer thickness brought about by mercury induced surface reactions. It is appreciated that the aluminum surface reflectivity may be measured from the transparent support side, thereby eliminating light attenuation that may occur in the liquid sample.

As a further alternative an aluminized thermistor may be employed, which would be sensitive to interaction between the aluminum surface and the mercury released from the tracer.

While sensors embodying the present invention are accurately characterized as not enzyme dependent, it should be appreciated from the foregoing that it is within the purview of the invention to use one or more enzymes to enhance the quantity of mercury ions reaching the negative aluminum electrode thereby increasing the sensitivity of the sensor.

Preferred Binder, Tracer, Assay Chemistry and Objectives Thereof

Assays which may be employed in accordance with the present invention include competitive assays, sandwich assays, and indirect sandwich assays.

In a competitive assay, the analyte and the tracer for the analyte compete for a limited number of binding sites on a binder, which is specific for the analyte and the tracer. The tracer, in accordance with the present invention, comprises the analyte or an appropriate analog thereof having a mercury or mercury releasing label. A change in at least one property of a metallic surface which interacts with mercury derived from the free and/or bound tracer phase is determined as a measure of the presence and/or amount of analyte.

In a sandwich assay, there is formed a complex of analyte bound to both a binder for the analyte and a tracer comprised of a ligand bound by the analyte labeled with mercury or mercury releasing means.

In an indirect sandwich assay, there is formed a complex of analyte bound to a first and second binder for the analyte and tracer bound to the second binder wherein the tracer is comprised of a ligand bound by the second binder labeled with mercury or mercury releasing means.

The sandwich or indirect sandwich assay may be accomplished by the forward, reverse or simultaneous technique.

In such assay procedures, there is formed a bound tracer phase and a free tracer phase and, in the assay, a change in at least one property of a metallic surface which interacts with the mercury is determined in the free and/or bound tracer to determine the presence and/or amount of analyte in a sample.

The binder used in the various assays is determined by the assay procedure. The binder is generally specific for at least the analyte and, in a competitive assay, the binder may be specific for both analyte and tracer. The binder may be an antibody and the antibody may be a monoclonal or polyclonal antibody. The binder may also be a naturally occurring substance. The binder may also be an antigen in the case, for example, where the analyte is an antibody. The selection of a suitable binder is deemed to be within the skill of the art from the teachings herein.

Similarly, the ligand portion of the tracer is determined by the assay procedure. Thus, for example, if the ligand of the tracer is to be bound to the analyte, the ligand may be an antibody (monoclonal and/or polyclonal) or in the case where the analyte is an antibody, the ligand portion of the tracer may be an antigen or an antibody. In an indirect sandwich assay, the ligand portion of the tracer may be an antibody or immunoglobulin bound by the second binder. The selection of a suitable ligand portion for the tracer is deemed to be within the scope of those skilled in the art from the teachings herein.

The binder for the analyte used in the assay may be supported on a solid support.

In some cases, the analyte may be captured on a solid support without the use of a binder for the analyte, and then the tracer is bound directly or indirectly to the analyte. Analyte is determined by measuring or determining a change in at least one property of a metallic surface which interacts with mercury derived from free and/or bound tracer.

In a preferred embodiment the ligand portion of the tracer is preferably labeled with mercury by the use of a carrier group comprised of a first portion to which mercury may be releasibly attached and second portion to which the ligand is attached. In accordance with a preferred embodiment, the carrier group is one to which a plurality of mercury may be attached whereby each tracer molecule is labeled with plurality of mercury. Thus, the carrier group has a backbone to which is releasibly attached a plurality of mercury whereby a single tracer molecule includes a plurality of mercury.

As representative examples of groups which can releasibly link mercury there may be mentioned primary, secondary and tertiary amines which may be present as a single group or multiple groups for releasibly linking mercury. Acid groups may also releasibly bind mercury. Sulfhydryl groups are also known to bind mercury; however, it is more difficult to release mercury ions from sulfhydryl groups. Although, in a preferred embodiment, the mercury is linked to groups from which it may be displaced by other metals, it is possible to link mercury to a tracer in a manner such that mercury is released therefrom by cleaving with an appropriate agent.

In accordance with one embodiment, there is provided a carrier group which is a copolymer of a polymer which provides multiple linking sites for mercury and a polymer which provides hydrophilic groups to render the copolymer, including attached mercury, water soluble. The hydrophilic polymer is preferably a non-ionic polymer to eliminate possible interference with mercury used as a label. As representative examples, there may be polyethylene glycol, or polymers which provide polyhydroxy groups, such as sorbitol, sugars, etc. The polymer to which multiple mercury labels may be attached may be, for example, polyacrylic acid or a polyimine, with polyethyleneimine being preferred.

The copolymer is preferably a graft copolymer of the two polymers.

The copolymer which includes a hydrophilic polymer portion and a polymer portion which is capable of releasibly linking or attaching mercury may be modified to include groups capable of reacting with an appropriate functional group of the ligand portion of the tracer, or substrate suitable for use with labeling enzyme.

In accordance with a preferred embodiment of the invention, there is provided a carrier group for attaching a plurality of mercury to a ligand, which is a copolymer of polyethyleneimine polymer and a hydrophilic polymer; in particular a polyoxyalkylene with polyoxyethylene being preferred. The polyoxyalkylene portion of the copolymer is provided with an end group which is capable of being linked to the ligand portion of the tracer; for example an amino, carboxy, sulfhydryl, or hydroxy group. In a preferred embodiment, the end group is a primary amine, derived from an epoxy group.

The polyethyleneimine portion of the copolymer serves as a backbone to which mercury may be attached and the hydrophilic polymer portion of the copolymer functions to provide compatibility with an assay system, and in particular blood as well as providing means for establishing specific assay identity by ligand attachment.

Although the present invention is not limited to any theoretical reasoning, it is believed that the hydrophilic polymer portion forms an outer hydrophilic shell around the polyethyleneimine polymer to which the mercury is attached, thereby providing compatibility with water-based assay systems.

Although, in a preferred embodiment, the mercury label is attached to a ligand through a carrier group and in particular a copolymer of the type described, it is to be understood that the overall invention is not limited to such coupling.

The tracer, is a preferred embodiment is comprised of a mercury label, a graft copolymer of polyethyleneimine and polyoxyethylene and a ligand attached to the polyoxyalkylene portion of the copolymer. A mercury label is displaceably bonded to the polyethyleneimine portion of the copolymer, and at least one epoxy group attached to the polyoxyalkylene portion may be opened so as to enable bonding to a ligand.

The polyethyleneimine portion of the copolymer has a structure as follows:

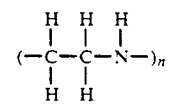

The polyethyleneimine polymer is capable of interacting with a mercury-containing compound, most preferably mercuric acetate, to link the mercury to the polyethyleneimine polymer. Although applicants do not intend to be limited to any theoretical reasoning, it is believed that the mercury is linked as mercuric ions in a chelated form.

In this example, a plurality of mercury may be reversibly linked to the polyethyleneimine polymer along the length of the polymer backbone. In a preferred embodiment, the polyethyleneimine polymer has a molecular weight of about 50,000. Compounds other than mercuric acetate may be used to attach the mercury to the polyethyleneimine polymer, but mercuric acetate is preferred because of its greater solubility.

It has been determined that the polyethyleneimine polymer with the mercury label, as described above, is not water soluble. Therefore, it is desirable to surround the polyethyleneimine with a hydrophilic surface.

To accomplish the above, the polyethylene glycol polymer is grafted to the polyethyleneimine polymer. The polyethylene glycol polymer preferably has a molecular weight of up to about 5,000, most preferably at about 1,000. The polyethylene glycol polymer, which is to be attached to the polyethyleneimine polymer, is prepared by coupling polyethylene glycol (PEG) with carbonyldiimidazole (CDI) to form PEG-di Carbonyl Imidazole (PEG-DCI), which is a structure with functional molecular end groups. To prevent cross-linking through the reactive imidazole rings on both ends of the PEG-DCI polymer, an epoxy compound, glycidol, is reacted with PEG-DCI to form a compound as follows:

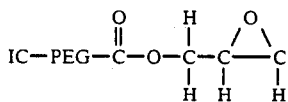

The epoxide group is introduced into the PEG-DCI to prevent cross linking since the Carbonyl Imidazole (CI) groups will react with —OH, —NH$_2$, etc. A group is reacted with one end of the molecule that is not reactive to CI groups; is not reactive with —NH— groups, yet can be made reactive after the graft copolymer is formed. Glycidol, being both an alcohol and epoxide, reacts with the PEG-DCI through the —OH. Although the epoxide will react with the —NH— of the PEI, it reacts considerably more slowly than do the CI groups. Cross linking is delayed due to the slow reactivity of the epoxide at room temperature with PEI.

It can be seen that the reaction of PEG-DCI with glycidol enables an epoxy group to be placed at the end fo the polyethylene glycol polymer chain. The polyethylene glycol polymer chain is then attached to the polyethyleneimine polymer. High salt concentrations may be used to control polymer conformation in solution. The resulting copolymer may be visualized as a polyethyleneimine central core surrounded by a polyethylene glycol shell with epoxide groups on the outside of the shell. The polyethyleneimine/polyethylene glycol graft copolymer is further reacted with ammonium hydroxide in order to open up the epoxy groups to produce an active site, which, in this embodiment is an amino moiety, onto which may be bonded an appropriate ligand. The epoxide may also be opened with other reagents to result in different end groups such as —OH, —COOH, —SH, which may be further modified by known techniques for ligand attachment.

Rather than glycidol, other agents may be employed to prevent cross linking yet allow future attachment.

A maleimide may be introduced into the PEG either before or after reaction with CDI. A molecule of the general form

where A is an amine reactive site (CI, active ester, etc.) and B is a non amine reactive, —SH or other reactive site (maleimide, etc.). A reacts with PEI while B cannot. B is then later reacted with a ligand of choice. Note in this case the reactive site in the ligand is something other than an amine. In the preferred method, previously described, A is CI and B is an epoxide from glycidol. While B will react slowly with —NH—, B is converted to —NH$_2$ rapidly (prior to cross linking). The ligand, then, must be modified to contain a reactive group (CI, active ester, etc.) that preferentially reacts with the terminal —NH$_2$ groups (stronger nucleophile, better position).

In this preferred embodiment, the ligand should not itself contain amines, as cross linking may occur. For protein attachment, a maleimide reaction, as described, or by reaction of an NHS or CI maleimide may be used.

Thus, for example, glucose tracer may be produced wherein maltose is dissolved in dry DMF (aprotic solvent) and CDI reacts to form Maltose-CI. This is a timed reaction, as the —CI groups will further react with other —OH in Maltose and cross link.

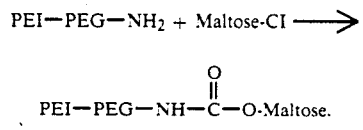

Maltose is used to provide an unmodified glucose-like end after the coupling reaction. A mercury label may then be linked to the PEI.

In forming a theophylline tracer 3-(-4-carboxybutyl)-1-methylxanthine (Clin. Chem. vol. 30, #7, 1984, page 1175) is converted to the active ester form by known techniques. This reacts directly with PEI-PEG-NH$_2$ to form the tracer. The resulting product may then be labelled with mercury.

A phenytoin tracer may be produced in which phenytoin active ester is formed by known techniques, and is reacted directly with PEI-PEG-NH$_2$.

A protein may be coupled to form a tracer in which the ligand is a protein. PEI-PEG-NH$_2$ is reacted with a commercially available bifunctional coupling agent (NHS-maleimide) to form PEI-PEG . . . maleimide.

The PEI-PEG-maleimide reacts directly with free sulfhydryl groups in proteins. It is possible to introduce —SH groups into proteins that do not possess available —SH groups by known techniques.

The tracer may then, in accordance with a preferred embodiment, be placed on a pad which is contained within a housing or package as hereinafter described. Also placed on the pad may be a binder for an analyte.

In accordance with a further embodiment of the invention, there is provided a substrate for a mercury releasing agent, said agent being attached to a ligand and thereby forming a tracer. The substrate releases mercury or mercury-containing polymer in proportion to the amount of tracer present.

In a preferred embodiment of this system, the tracer label (mercury releasing agent) is an enzyme that causes cleavage or dissolution of insoluble polymeric materials. Examples of such enzymes include cellulases, dextranases, amylases, agarases, proteolytic enzymes, etc.

Functionally, the substrate is comprised of mercury containing copolymer covalently attached to an insoluble polymeric substrate. The enzyme is attached to the ligand through known techniques, and is selected to be reactive with a modified, mercury polymer containing substrate.

By way of example, bacterial alpha-amylase is readily available. It is known to cleave both soluble and insoluble fractions of starch at intermediate points in the polymeric starch structure. Amylose (insoluble fraction in starch) is thought to be a linear polysaccharide of several million molecular weight. Amylase is known to cleave the insoluble amylose molecule into smaller, soluble fractions by reaction at intermediate points along the linear polysaccharide. Dye molecules are readily attached to amylose without limiting amylase activity. Amylase activity may be measured by quantification of soluble dye content after reaction. In a similar manner, mercury-containing PEI-PEG copolymer may be covalently attached to insoluble amylose. Amylase activity cleaves the insoluble amylose molecule into smaller, soluble units, each unit containing mercury-containing PEI-PEG copolymer. The mercury is released from these soluble, copolymer-containing polysaccharide units with agents, such as nickel chloride/ammonium chloride, as previously discussed. This second embodiment provides chemical amplification in the system, since a single tracer molecule is able to cleave many mercury copolymer-containing polysaccharide units per minute.

The preparation of the mercury-containing insoluble substrate generally follows the principles outlined herein for preparation of copolymer tracers. By way of example, a substrate for alpha-amylase may be prepared by activating insoluble amylose according to generally known techniques, for example, with CDI in dry DMF. PEI is allowed to react with the activated amylose, after which the amylose-PEI is reacted with methoxy-PEG-CI to improve liquid solubility, as previously discussed. Methoxy PEG-CI is used rather than PEG-DCI so as to eliminate cross-linking.

Alternatively, CI-PEG-NH$_2$, from CI-PEG-glycidol, may be used. The ratio of mercury copolymer to amylose is adjusted to allow amylase activity while providing for high molecular amplification.

In accordance with another aspect of the present invention, a reagent kit or package for determining analyte is provided, which includes a tracer comprised of ligand labeled with mercury or mercury-releasing means and a binder for at least the analyte. The binder may be supported on a solid support. The reagent kit or package may also include other reagents, such as a substrate pad and/or a releasing agent for releasing mercury label. The kit may also include standards, buffers, etc.

In accordance with yet another aspect of the present invention, there is provided a device or product for determining analyte which includes a tracer comprised of a ligand labeled with mercury, a binder for at least the analyte, and metallic surface which interacts with mercury and has at least one property thereof changed by such interaction. Aluminum is particularly preferred. The metal, tracer and binder are incorporated into a container or housing in a manner such that sample may be added to the housing or container and the presence and/or amount of analyte determined.

In accordance with yet another aspect of the present invention, there is provided a device or product for determining analyte which includes a tracer comprised of a ligand labeled with a mercury releasing means, a binder for at least the analyte, a mercury containing substrate, and a metallic surface which interacts with mercury and has at least one property thereof changed by such interaction. Aluminum is particularly preferred. The metal, tracer, binder, and substrate are incorporated into a container or housing in a manner such that sample may be added to the housing or container and the presence and/or amount of analyte determined.

In accordance with a preferred embodiment, the metallic surface which is to interact with mercury is present in the form of an electrode and mercury is released from a bound and/or free tracer or cleaved substrate phase formed in the assay and caused to interact with the electrode to change at least one property thereof.

In accordance with a particular embodiment, there is provided in a container or housing an electrode which is formed from a metal the surface of which interacts with mercury, a binder for the analyte, a tracer comprised of a ligand labeled with mercury and a releasing agent for releasing mercury label from the tracer, all of which are situated and positioned in the housing such that upon adding of sample, there is formed a bound tracer phase and a free tracer phase, with mercury being released from one of the free or bound tracer phase (preferably the free tracer phase) and caused to come into contact and interact with the electrode surface to change at least one property thereof.

In accordance with a preferred embodiment, there is provided a housing having an inlet means for receiving a sample suspected of containing analyte, a means for containing the mercury labeled tracer, means for containing a binder for at least the analyte, and means for containing a releasing reagent for releasing mercury label from the tracer and a metal electrode formed from a metal the surface of which interacts with mercury. The various means are situated in the housing in a manner such that analyte, binder, and tracer are contacted to form a bound and free tracer phase, with free tracer phase coming in contact with the releasing agent, and released mercury then coming in contact with the electrode.

In accordance with a further particular embodiment, there is provided in a container or housing an electrode which is formed from a metal the surface of which interacts with mercury; a binder for the analyte; a tracer comprised of a ligand labeled with mercury releasing means, a mercury containing substrate, a releasing agent for releasing mercury label all of which are situated and positioned in the housing such that upon addition of sample, there is formed a bound tracer phase and a free tracer phase, with mercury being released as a function of either the free or bound tracer phase (preferably the free tracer phase) and caused to come into contact and interact with the electrode surface to change at least one property thereof.

In accordance with a further preferred embodiment, there is provided a housing having an inlet means for receiving a sample suspected of containing analyte, a means for containing tracer, means for containing a binder for at least the analyte, means for containing a mercury containing substrate, and means for containing a releasing reagent for releasing mercury and a metal electrode formed from a metal the surface of which interacts with mercury. The various means are situated in the housing in a manner such that analyte, binder, and tracer are contacted to form a bound and free tracer phase, with free tracer phase coming in contact with a mercury containing substrate, the products of which contact a releasing agent, and released mercury comes in contact with the electrode.

The container or housing may also further include a means for determining a sufficient volume of sample within said inlet means. The inlet means may comprise a capillary tube.

The tracer-containing means may comprise solid absorbent such as a pad impregnated with at least said tracer, and the releasing reagent-containing means may comprise a solid absorbent such as a pad impregnated with the releasing reagent. The tracer-containing means may also include a binder for the analyte. The tracer-containing means and the releasing reagent containing means may each be comprised of an absorbent material that facilitates capillary flow through the material.

In a preferred embodiment, the metal surface which interacts with the mercury is aluminum.

The means for determining the presence of a sufficient volume of sample within said inlet means may include electrical means which are bridged by the sample being assayed. These electrical means may comprise a pair of electrodes, which determine the presence of an adequate volume of sample inside the inlet means.

In a preferred embodiment, the device contains an aluminum electrode, which is contacted with released mercury, and which is negatively charged and is complemented by a positively charged electrode, and thus incorporated as part of an electrical sensing means. The electrodes are bridged by a fluid sample. The positively charged electrode is preferably comprised of aluminum as well. The positively charged electrode may also be one of the electrodes which determines a sufficient volume of sample within the inlet means.

The aluminum electrode which is to be contacted with the released mercury, normally has a protective layer of $Al_2O_3$, which prevents rapid oxidation of the aluminum. Mercury serves to destabilize the $Al_2O_3$ layer. The changes in the electrical characteristics of the surface of the electrode, when the aluminum electrode is contacted by and the aluminum interacts with the mercury, may be measured in order to determine the presence and/or amount of analyte.

When water is present, an additional porous $Al(OH)_3$ layer will form on the $Al/Al_2O_3$ surface. Mercury and/or its ions are relatively permeable in the $Al(OH)_3$ layer; thus, the interaction can proceed in aqueous solutions. It must be noted, however, that if the porous aluminum hydroxide layer is too thick, the sensitivity of the interaction of the mercury with aluminum will be markedly diminished. The aluminum electrode, therefore, is preferably subjected to treatment which will provide for a suitable oxide/hydroxide thickness to enable adequate sensitivity of the interaction of the aluminum surface with mercury.

The housing may further include a water-soluble membrane disposed between said tracer-containing means and said releasing agent-containing means. The water-soluble membrane is capable of being dissolved upon contact of said membrane by said sample and said tracer. The membrane may be of a thickness such that the membrane is completely dissolved after a predetermined time period. This predetermined time period provides for an incubation period of sample and tracer on the tracer-containing means.

In another embodiment, the tracer-containing means and the releasing reagent-containing means are separated by a space. As with the water-soluble membrane, the spacer provides for an incubation period of sample and tracer on the tracer-containing means. At the end of the incubation period, the device is compressed so as to enable the tracer-containing means and the releasing reagent-containing means to contact each other and to enable the flow of sample from the tracer-containing means to the dissociating reagent-containing means.

It is understood that the above-described water soluble membrane and spacers are also applicable to an embodiment utilizing a mercury releasing tracer in conjunction with a mercury containing subsrate to provide, for example, an extended incubation period for tracer and/or substrate reactions.

In alternative embodiments, the housing may further contain means for dividing sample flow into two paths. In one embodiment, a first flow path includes a tracer and binder, a releasing reagent, and a metal electrode as described above. The second flow path includes a tracer, a binder, a predetermined amount of mercury label independent of ligand, and a metal electrode. In a preferred embodiment, the first flow path also includes a spacer means, such as a blank pad, in order to balance the flow time of the sample paths.

In another embodiment, having a divider which divides the sample flow into two paths, the first flow path includes a tracer and binder means, a releasing reagent, and a metal electrode. The second flow path includes a predetermined amount of analyte, a tracer and binder means, a releasing reagent, and a metal electrode.

In yet a further embodiment, a first flow path in the device includes binder, tracer, releasing agent, and electrode. The second path includes tracer, releasing agent and electrode. The presence and/or amount of analyte is determined by comparing changes in the properties of the two electrodes; for example, such changes can be sensed electrically.

It is understood that the above-described self-referencing technologies are also applicable to the embodiment of the invention utilizing a mercury releasing tracer in conjunction with a mercury containing substrate.

As stated above, the device of the present invention may be used in connection with various types of assays, including competitive assays, sandwich assays, and indirect sandwich assays. Also, as above-mentioned, in most cases these assays require the use of at least one binder for the analyte in addition to the tracer. The exact method of placing binder and tracer on a releasing pad or pads within the sensor, and the order of contact of the tracer and binder by the sample depends, therefore, on the type of assay employed, and may vary within the scope of this invention.

Thus, for example, in a sandwich assay procedure, sample and tracer (a ligand which is bound by the analyte labeled with mercury) may be initially contacted in the capillary tube portion of the device to form a free tracer phase and a bound tracer phase in which tracer is bound to analyte. Thereafter, such phases are contacted with a binder for the analyte whereby the bound tracer phase is bound to the binder. The free tracer phase, which remains unbound then contacts releasing agent and released mercury interacts with the electrode.

The present invention is also applicable to DNA (RNA) determination in which case the tracer is appropriate DNA (RNA) labeled with mercury.

After hybridization, mercury is released from the hybridized probe and caused to interact with a metal, as hereinabove described.

Accordingly, the term "tracer" or "ligand labeled with mercury" as used herein includes a DNA (RNA) probe labeled with mercury.

The following are examples of the present invention. The scope of the invention, however, is not intended to be limited thereby.

EXAMPLE 1—GLUCOSE TRACER

Polymer

A. Fluorescent Polyethyleneimine (PEI)

In a 200 mL beaker, add 20.00 grams PEI solution (50% aqueous solution, molecular weight of 50,000, Aldrich #18,197-8); add 80.00 mL distilled water, mix and/or sonicate until homogeneous. Add 10 mg (1 vial) lissamine rhodamine B (LRB, Molecular Probes #L1908) to glass scintillation vial; add 0.5 mL dry Dimethyl Formamide; stir until LRB is dissolved. Add 4.5 mL distilled water rapidly; mix well; and transfer immediately to rapidly stirring PEI solution. Mix at room temperature for 15 minutes. Add 30.0 grams NaCl to solution and mix until dissolved. Filter through glass filter (Whatman 934AH). Dilute solution by adding 200 mL aqueous saturated NaCl solution; mix until homogeneous. Volume approximately 300 mL.

B. glycidol-PEG-CI

In a 500 mL flask, add 100 mL dry acetone and 6.5 grams 1,1'-Carbonyldiimidazole (CDI, Aldrich #11,553-3); mix in water bath at 30° C. for 15 minutes. Add 20.0 grams polyethylene glycol (PEG, molecular weight=1,000, Sigma #P-3515) as waxy solid. Stir for 15 minutes at 30° C. The PEG should dissolve within approximately 5 minutes.

To the above solution add 1.330 mL glycidol (1.482 grams, Sigma #G-0887) and mix for 1.0 hour at 30° C.; evaporate acetone from solution at 30° C., under reduced pressure.

C. Graft polymer

Dilute glycidol-PEG-CI solution from B above with 50 mL aqueous saturated NaCl. Mix rapidly. Add this solution to the PEI solution from A above while rapidly stirring. Stir for 2 minutes at room temperature, then add 10.00 mL distilled water while continually stirring. Solution clarifies in approximately 2 minutes. Continue stirring for 10 minutes total, then add 100 mL ammonium hydroxide (Fisher #A669C). Stir for approximately 1 minute; add 5.00 mL 6N NaOH to raise pH to 12.0. Stir at 32° C. for 20 hours.

Dialyze in Spectra/Por 1 tubing (D1614-4, molecular weight=6-8,000) against distilled water of pH 10.7 (NaOH) for 10 days at room temperature and 2 changes per day. After dialysis, evaporate excess water from polymer solution under reduced pressure (40° C.) to 200 mL final volume (50 mg/mL initial PEI concentration). Store at 4° C. until used.

D. glucose tracer

In a glass scintillation vial, dissolve 0.5 gms maltose (hydrate, Sigma M-5885) into 2.0 mL dry DMF. To this solution, add 1.333 mL of a solution of 0.5 gms CDI dissolved in 2.00 mL DMF. Add with rapid mixing. Mix for 60 seconds; then add 10 mL distilled water; mix rapidly; then add to a previously prepared solution of 10 mL of graft copolymer (C above) diluted with 20.0 mL distilled water.

Mix at room temperature for 1 hour; then dialyze as before for 2 days. After dialysis, evaporate as before to 25.0 mL total volume.

Dissolve 400 mg. Mercuric acetate (Fisher M-143 75797) into above solution. Adjust pH to 7.0 to 7.1 with addition of aqueous NaOH. This solution may be frozen until used.

EXAMPLE 2—GLUCOSE ASSAY

Aluminum Preparation

The aluminum used was 1145-0 (Davidson Metals, Inc., Specialty Metals Division) at 0.005 inch in thickness. A sheet approximately 3.5 inches by 9 inches is immersed in 600 mL of 1.0M NaOH (EM Science) in distilled $H_2O$ and allowed to react for 5 minutes at 20° C. The foil is removed with forceps and thoroughly rinsed with distilled $H_2O$. It is then wiped dry on both sides with a soft cotton cloth, paper towel or tissue.

The foil is next immersed in 300 mL of a (92° C.) solution of 0.42M $H_3PO_4$ (J T Baker), 0.59M $CrO_3$ (Mallinckrodt) for 10 minutes. It is then removed with forceps; the acid is allowed to initially drain off then it is thoroughly washed with distilled $H_2O$. The foil is then wiped dry as in the previous step.

The last treatment immerses the foil in 300 mL of a boiling solution of 10% (w/v) methoxypolyethyleneglycol, molecular weight 1900 (Sigma) for 10 minutes. It is removed with forceps; washed thoroughly with distilled $H_2O$ and wiped dry.

The prepared foil is stored under ambient conditions in plastic bags.

Sensor Base Assembly

The base for the sensor is assembled by utilizing a disposable glass microscope slide (Abco), 1" by 3". This provides rigidity and support for subsequent manipulations. To this is applied 2 strips of double stick tape (Scotch) which cover the entire surface as well as overlaps one end by approximately ½". The treated foil is then applied to the tape and the slide is pressed onto the foil. The ½ inch overlap is then cut approximately 0.33 inches on both sides of the slide and folded over to form a contact point for attachment of a clip to the foil. The foil plate will become the negative electrode in the system. The foil layer is insulated from the positive electrode by overlaying No. 33 electrical tape (Scotch), 0.007 inch thick, through which 6, 0.245 inch diameter holes have been punched that are 0.5 inch apart, center to center. The tape is pressed down to insure a seal around the edges of the holes. The positive electrode is attached by using the same treated aluminum which is cut into small pieces 0.05 inch wide by 0.75 inch in length. The positive electrode is then placed onto the insulating tape and overlapped onto the exposed aluminum by 0.025 inch. The positive electrode is held in place with a plastic self-adhesive, 0.26 inch diameter reinforcement (Avery Label). An overlap of 0.008 inches occurs around the insulating tape.

Releasing Pad Preparation

The component used to release the mercury ion from the glucose tracer is prepared by manufacturing 0.245 inch diameter circles of Eaton Dikeman 937-20 paper (0.010" thick). A solution of 0.1M $NiCl_2$—$6H_2O$ (Sigma) plus, 5.0M $NH_4Cl$ (Fisher) is prepared in distilled $H_2O$. The paper circles are then placed on a 1" by 3" disposable glass microscope slide (Abco) in rows 3 by 10. To each of these circles, 0.007 mL of the $NiCl_2$6-$H_2O$/$NH_4Cl$ solution is dispensed. The entire glass slide is placed in a 60° C. oven and allowed to dry for 30 minutes. The releasing pads are then stored desiccated at 20° F.

Concanavalin A/Glucose Tracer Pad Preparation

The component used to selectively react with glucose is prepared by manufacturing 0.245 inch diameter circles of Eaton-Dikeman 939-39 paper (0.028" thick). The paper has a "coarse" and a "smooth" side. The circles are placed, coarse side down, on a disposable polystyrene petri dish (Fisher). The solution applied to the paper is made by dissolving Type V Concanavalin A (Sigma) at 0.05 g/mL in distilled $H_2O$. The glucose tracer is diluted 20% with saturated NaCl (Sigma). The components are added to a 12 by 75 mm disposable glass test tube (Scientific Products) as follows: (1) 1.0 mL Concanavalin A (50 mg/mL), (2) 0.286 mL of distilled $H_2O$, and (3) 0.857 mL of the NaCl diluted glucose tracer. The components are mixed and then allowed to react for 15 minutes at 20° C. The solution is then dispensed onto the previously prepared paper circles at 0.0175 mL/circle. The plastic petri dish is then placed in a dry ice/isopropyl alcohol (JT Baker) bath and allowed to freeze thoroughly (30 Minutes). The paper disks are then lyophilized for 16 hours. Subsequent storage of the prepared paper is at 20° C., desiccated.

Final Sensor Assembly

The sensor base plate has added to each of the 0.245 inch diameter exposed aluminum surface, a single releasing pad paper circle. The releasing circle is overlayed directly on the aluminum surface (negative electrode) and the small positive electrode is repositioned on the upper surface of the paper. When dry, the releasing circle acts to insulate these electrodes from one another.

Directly on top of the releasing pad and positive electrode, the Concanavalin A/Tracer pad is directly overlayed.

Performance of Glucose Assay

The assembled sensor is connected to the electronic circuitry by a negative electronic lead, to the common aluminum surface and, positive lead, to the small individual strip.

The electronic circuit maintains a constant 0.2 volts between the positive and negative electrodes, averages the current flow between electrodes for 60 seconds after blood addition and displays the average value in microamps.

Glucose in whole blood is measured by compressing the paper pads together with forceps, and, while maintaining this pressure, dispensing 0.04 mls of whole blood onto the Concanavalin A/Tracer pad. Pressure is maintained for 1 minute while the current generated is measured.

A typical standard curve for glucose is shown below in tabular form:

| Glucose Concentration | Measured Current |
|---|---|
| (mM) | (uA) |
| 0.0 | 2.4 |
| 6.0 | 8.6 |
| 12.0 | 17.4 |
| 24.0 | 34.6 |

Electrode Preparation

A procedure for treating each aluminum electrode includes treating the electrode in order to remove $Al_2O_3$ and other impurities, allowing restoration of the $Al_2O_3$ and $Al(OH)_3$ layers under controlled conditions, and then adding a wetting agent to the electrode surface so as to make the surface uniformly hydrophilic. The surface layers of oxide/hydroxide of the electrode should be kept sufficiently thin so that it can react properly with the released mercury ions.

A preferred treatment of the aluminum electrode is as follows:

Aluminum is reacted in approximately 1.0 molar sodium hydroxide solution for 5 minutes at room temperature in order to dissolve the surface of the aluminum, as well as to remove any impurities. The aluminum is then rinsed with deionized $H_2O$.

The aluminum is then reacted in 0.4 molar $Cr_2O_3$ with 0.6 molar $H_3PO_4$ for 10 minutes at 88° to 92° C. This removes the oxide layer from the aluminum and neutralizes the surface, which had been basic as a result of the previous addition of sodium hydroxide. The aluminum is then rinsed again with deionized water, and then boiled in 0.05 molar methoxy polyethylene glycol solution for 10 minutes. Methoxy polyethylene glycol serves as a wetting agent for the surface and provides a uniform hydrophilic $Al_2O_3$ and $Al(OH)_3$ surface. Although methoxy polyethylene glycol is a preferred wetting agent, it is to be understood that other wetting agents may also be employed, e.g. PEG, surfactants, polyhydroxy compounds, etc. After the aluminum is boiled in the methoxy polyethylene glycol solution it is air dried. The product is an aluminum electrode or plate having a uniformly hydrophilic surface layer having a proper sensitivity for interaction with mercury. Although the above treatment procedure is illustrative of the preparation of an aluminum electrode having a surface layer of a desired thickness, it is to be understood that other procedures may be employed and that the scope of the invention is not to be limited by the above teaching. It is believed that the wetting agent treatment fulfills two purposes. First, it provides a strong wetting agent near the surface, and second, it acts as a porogenic agent, causing small pathways or cracks (voids) in the $Al(OH)_3$ layer.

Sensor Signals

As explained earlier, the tracer released mercury interacts and ultimately amalgamates with the surface of the large negative aluminum electrode, of the sensor as a function of the quantity, if any, of test analyte present in the liquid specimen introduced into the bioassay instrument. The interaction and ultimate amalgamation changes the surface characteristics of the aluminum electrode, which changes can be measured electrically, producing current signals, which are representative of the quantity of test analyte in the specimen.

Figure 24:
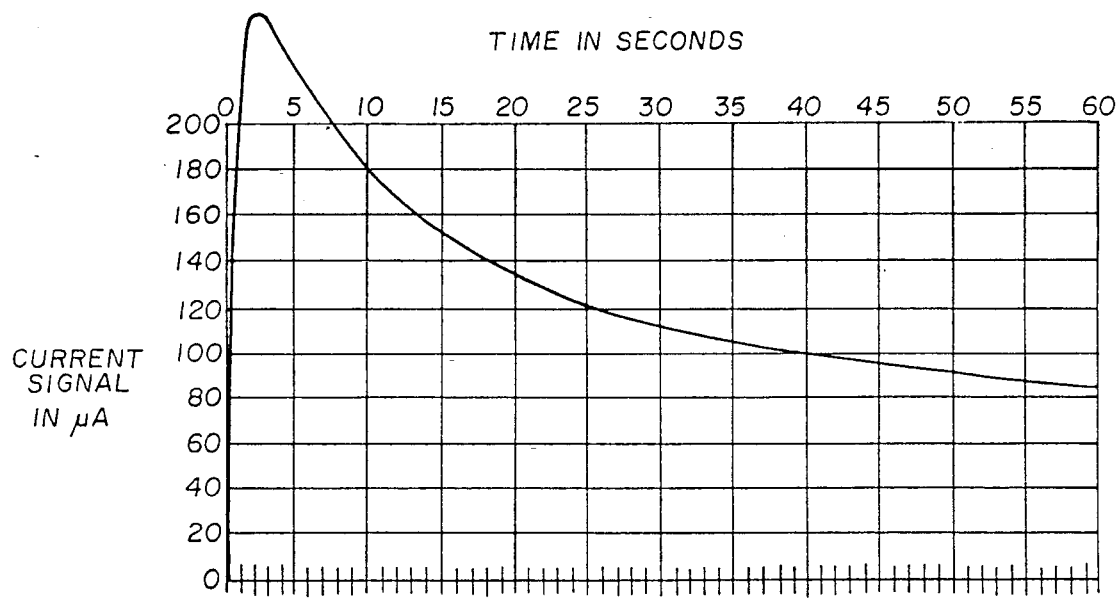
FIGS. 24 and 25 are graphic representations of empirically derived glucose curves showing the sensor output current signal in respect to time.
Figure 25:
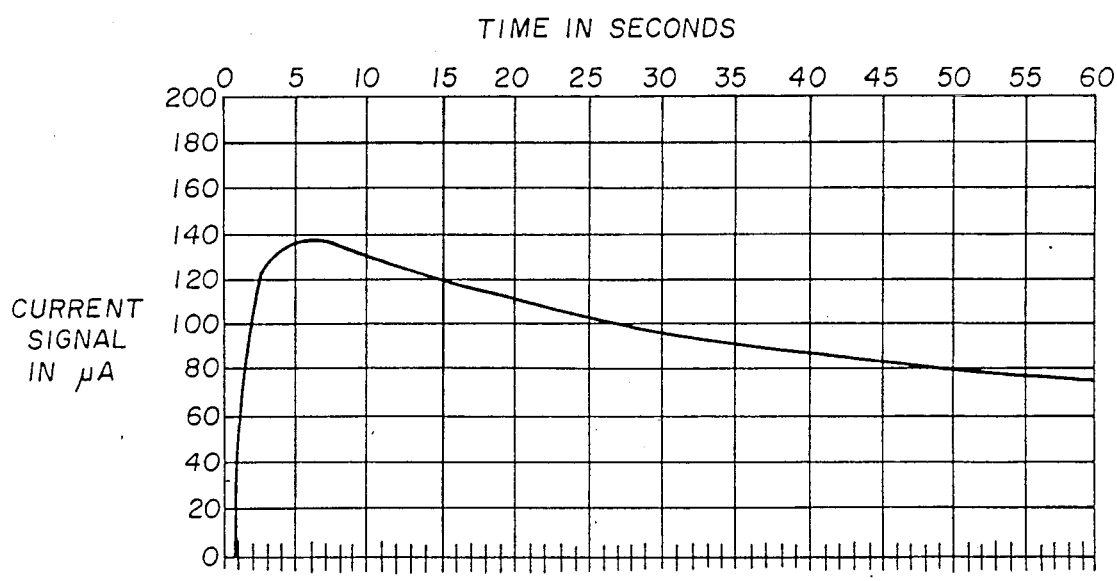

Typical samples of amplifier current signal waveforms from a single output sensor for the analyte glucose are shown in FIGS. 24 and 25. Empirical studies have known that portions of glucose curves typified by FIGS. 24 and 25 are driven asymptotically toward a value which is proportional to the concentration of mercury released from free tracer in the liquid specimen, at the reagent pad. The area under each curve is also related to analyte concentration.

Figure 26:
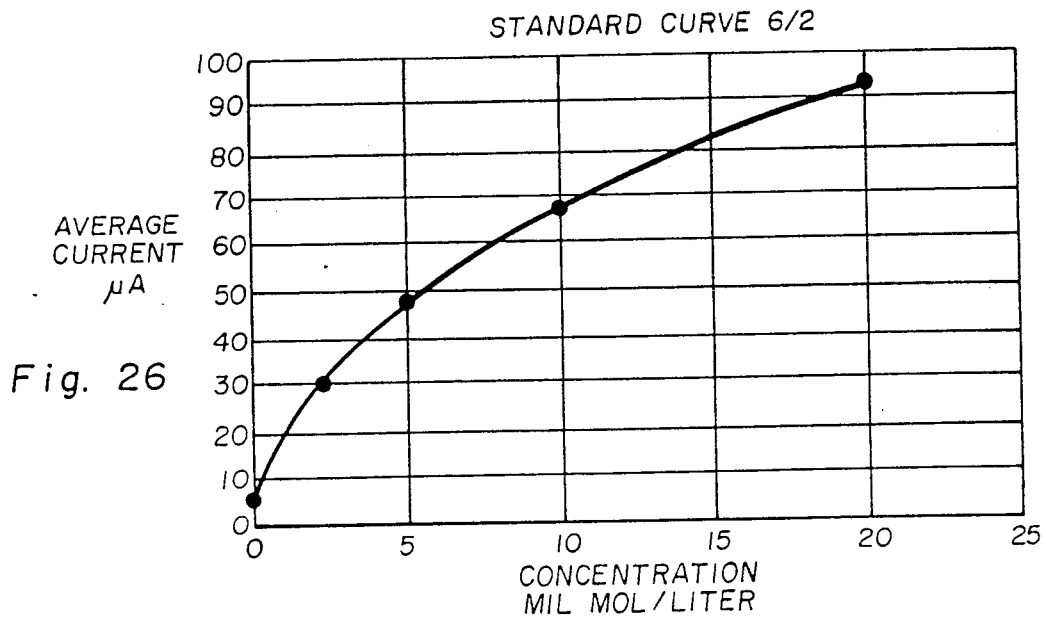
FIG. 26 is a graphic representation of an empirically derived relationship between the sensor output current signal and the released tracer concentration.

The stated empirical studies have also shown there is a monotonically increasing relationship between the sensed current and the released mercury concentration in the processed specimen. The relationship is graphically shown in FIG. 26.

The waveforms in question are capable of conventional mathematical expression and said mathematical expression is used in a well known manner to create either single output sensor or multiple output sensor software for each specific instrument which is programmed into the microprocessor of the hand-held instrument, as hereinafter explained.

Two sensor output waveforms result, when a dual output sensor is used, each of which is amplified. The relationship between the two output waveforms is a measure of the quantity of mercury released from the free tracer and, thus, a measure of the concentration of test analyte (glucose, for example) present in the liquid specimen. The mathematical expression of said waveform difference is used to create the dual output sensor software programmed into the microprocessor.

The sensor current signals, derived as explanined above, are electrically communicated to the proximal tab 278 and thence across spring contacts 262 (FIG. 2) along leads 266 to the input site of the electronics 336 (FIG. 2) carried by the circuit board 332 (FIG. 2).

Instrument Electronics

Figure 27:
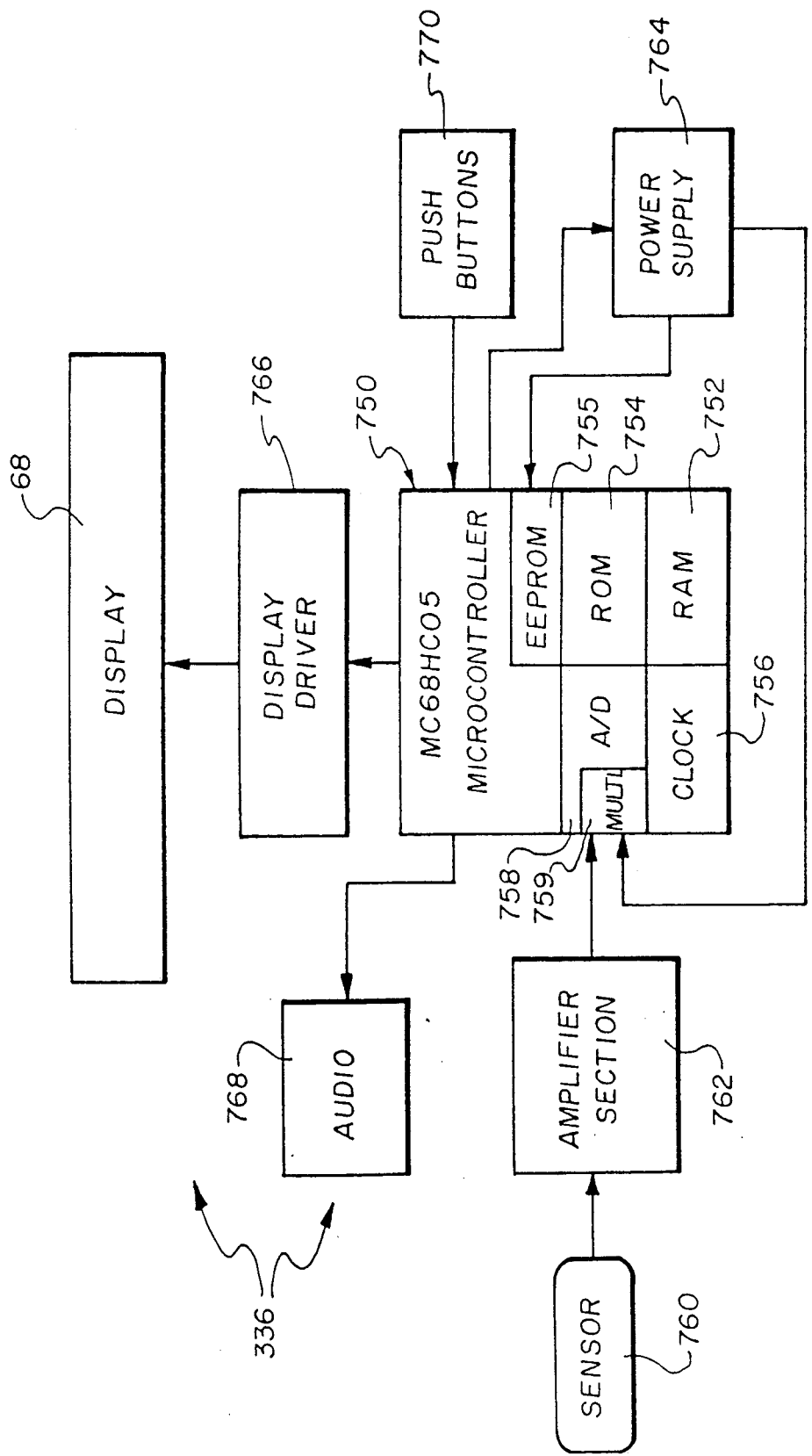
FIG. 27 is a block diagram of the preferred electronics of the instrument.

Referring to block diagram FIG. 27, the electronics are comprised of 8 major blocks or sections. An MC68HC05 microcontroller 750, furnished by Motorola, is an eight bit microprocessor with on board random access memory (RAM) 752, electrically erasable programmable read only memory (EEPROM) 755, read only memory (ROM) 754, CLOCK 756 and an eight channel analog to digital (A/D) converter 758. The A/D converter comprises an internal multiplexer 759. The MC68HC05 microcontroller is a ROM masked part and comprises software programmed into the ROM. As described in greater detail hereafter, the sensor 760 may be configured with one or more negative electrodes, one common positive electrode and a liquid sensing electrode L. Multiple electrode design may be used to compensate for temperature, hematocrit or other error-inducing common-mode conditions.

The amplifier section 762 provides a 0.2 VDC potential across the sensor and converts the resulting current flow to a voltage signal. The voltage signal output of amplifier section 762 is a known function of analyte concentration. These voltages as well as the battery voltage from the power supply circuit 764 are multiplexed at 759 within the 8 bit analog to digital converter 758. These digitized voltage signals are then analyzed by the software stored in ROM 754 and the result is stored in RAM 752 or EEPROM memory 755. The system clock 756 controls the timing of the microcontroller 750 and creates a series of regular pulses used to measure the progression of time.

At the user's request and/or under software control, time, date, and analyte values can be called up, and displayed either numerically or graphically on the custom 16×84 pixel liquid crystal display 68. The display is driven by two 1503F drivers which comprise display drive circuit 766, manufactured by SMOS Inc. An audio transducer 768 is also connected to the microcontroller 750 to signal the user of various conditions such as end-of-assay or as an alarm clock function (beeps). This transducer is also used as an acoustical coupler to facilitate telephone data transfer.

Several push buttons, designated collectively as 770 in FIG. 27, are interfaced to the microcontroller to allow the setting of time, date and the retrieval of information. Magnetic reed switch S3 (shown schematically in FIGS. 2 and 28) is activated by magnet 301 carried by button 116. When the lancet is triggered by depression of button 116 thereby piercing the skin, the reed switch S3 closes momentarily signaling the start of a new assay.

The power supply 764 comprises a 3.0 VDC battery. Part of the supply current is regulated to +2.5 VDC at 764B for the A/D reference and further divided to 0.2 VDC for the sensor biasing. The regulated part of the power supply 764B is controlled by the microcontroller 750 so the voltages used to power the analog circuits can be turned off for energy conservation.

Circuit Operation

Figure 28:
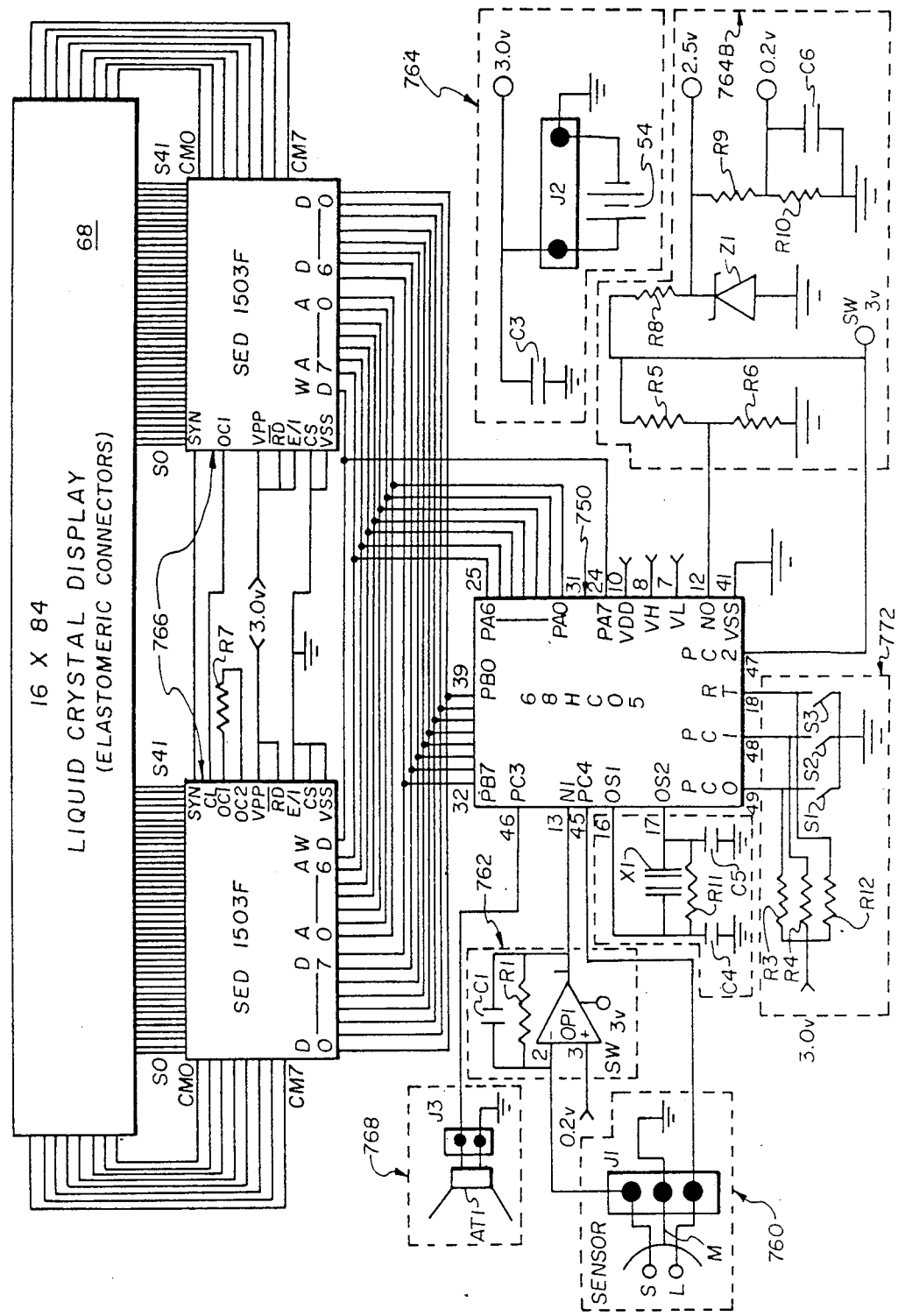
FIG. 28 is a circuit diagram of the preferred electronics of the instrument for a single output sensor.

FIG. 28 illustrates a presently preferred single channel sensor circuit, generally designated 336, which corresponds to the block diagram of FIG. 27. Component labels are denoted as follows: R—resistor, C—capacitor, and J—jack (connector).

Circuit 336 of FIG. 28 is powered (via J2) by a 3.0 volt direct current (VDC) battery 54. C3 filters out any stray transients induced by the digital circuits. The microcontroller (MC) 750 at terminal VDD and the display drivers 766 at terminals VPP are powered directly from power source 54. Terminals VSS for each integrated circuit of 766 are connected to circuit ground, consistent with the manufacture's instructions.

Under software control, microcontroller 750 can turn on or off port PC2 providing a switchable 3 VDC (SW 3.0) to power the sensor 760, the amplifier section 762 and the voltage reference circuits. Thus, the total current usage by the circuit can be greatly reduced by turning off noncritical circuitry when not needed. R5 and R6 divide the SW 3.0 voltage in half. The resulting voltage is monitored by the microcontroller's A/D converter 78 via terminal NO. Thus, the system can sense low battery voltage and display an appropriate user message. R8, in series with the 2.5 VDC voltage reference Z1, creates a 2.5 VDC source used by the microcontroller 750 as an A/D high reference (VH). This regulated 2.5 VDC is also divided by R9 and R10 to 0.2 VDC. C6 is provided for transient filtering. The 0.2 VDC forms the microcontroller's A/D converter low reference (VL) and the sensor bias voltage applied to the amplifier OP1 on pin 3.

As per the manufacturer's data, a crystal X1, shunted by R11 and bypassed to ground by C4 and C5, is connected to terminals OS1 and OS2 of microcontroller 750 to form the system clock circuit.

S3, the aforementioned normally closed magnetic reed switch, is connected between the reset pin RT of MC 750 and ground. The reed switch S3 is mounted on circuit board 320 to be adjacent to magnet 301 carried by push button 116 of assembly 300. Switch S3 is a normally-closed switch but is held open by the magnet placed in close proximity thereto. When the button 116 is depressed, the switch S3 is allowed to close. When button 116 is manually released, after the lancet has been triggered, the magnet 301 is displaced by the memory of spring 306 to the proximity of switch S3, thus causing switch S3 to open. While S3 is opened by proximity of magnet 301, current through R12 pulls the rest of MC 750 high. Thus, when the button 116 is depressed and mechanical triggering occurs, S3 closes and resets MC 750. S1 and S2, with their appropriate pull up resistors R3 and R4, are connected to pins PC0 and PC1 of MC 750. The state of these momentary-contact normally-open push button switches are read by MC 750 to allow the user to input control data. As per the software, hereinafter described, mode selection, setting of time and date, and transmission of data are controlled by these push button switches S1 and S2. As mentioned before, button 114 is unused and available for future use. The sensor 760, connected to the circuit via J1, in its simplest electronic configuration consists of three aluminum electrodes. The large electrode M, where most of the chemical reaction takes place, is connected to ground. One small electrode used to sense the presence of liquid L is connected to pin PC4 of MC 750 such that a software controlled 3 VDC can be applied or not to electrode L. The current sensing electrode S is connected to amplifier OP1. OP1 performs four functions. First, it provides a buffered +0.2 VDC to electrode S of the sensor thus maintaining a 0.2 VDC bias between S and M of the sensor 760. Second, it amplifies the sensor output signal, which is in the form of current flow from electrode S to electrode M (conventional current flow). Third, it converts the current signal to a voltage signal which is in turn read by A/D via pin N1 of MC 750. Fourth, it low pass filters the sensor signal to eliminate high frequency noise. The cutoff frequency of amplifier OP1 is established by R1 and C1 and, in a presently preferred embodiment, is approximately 1.5 Hertz.

The display drivers 776 are interfaced to the microcontroller MD 750 by ports PA0 through PA7 for pixel addressing and port PB0 through PB7 for display data. The other connections to the display drivers are conventional, in accordance with the SMOS application guide for the SED1503 series for display drivers.

The 16×84 pixel liquid crystal display LCD 68 is custom fabricated using current state-of-the-art technology. The display 68 is interfaced to the display drivers 766 by elastomeric connectors or zebra strip connectors.

Figure 29:
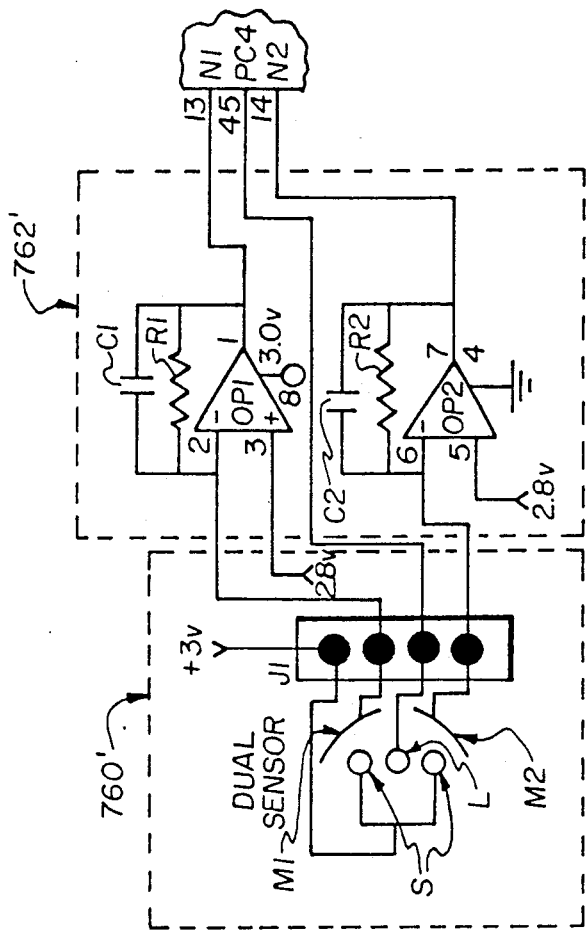
FIG. 29 is a fragmentary circuit diagram of the preferred electronics of the instrument for a dual output sensor.

FIG. 29 shows a modified sensor/amplifier circuit used to accommodate a dual output sensor. Note that the configuration is similar to FIG. 28 but with two electrodes M1 and M2 and their associated amplifiers OP1 and OP2. The positive electrode S is common and connected to +3 VDC. Amplifiers OP1 and OP2 comprise noninverting inputs which are connected to a +2.8 V source creating a buffered +2.8 VDC potential on M1 and M2. This results in 0.2 VDC across sensor electrodes S and M1 and S and M2, respectively, with the proper polarity. The output of each amplifier is read by the A/D 758 of MC 750 and compared by software programming into MC 750. Table I comprises a list of component values associated with the aforementioned circuits.

TABLE I

| COMPONENT | SOURCE | VALUE |
| --- | --- | --- |
| 68HC05 | MOTOROLA | MC68HC05 |
| SED1503F | SMOS | SED1500F |
| OP1 | INTERSIL | ICL7621 |
| Z1 | MOTOROLA | LM336Z 2.5 V REF |
| X1 | MULTIPLE | 32.768 KHZ XTAL |
| R1 | MULTIPLE | 5 KΩ |
| R2 | MULTIPLE | 5 KΩ |
| R3 | MULTIPLE | 10 KΩ |
| R4 | MULTIPLE | 10 KΩ |
| R5 | MULTIPLE | 220 KΩ |
| R6 | MULTIPLE | 220 KΩ |
| R7 | MULTIPLE | 10 KΩ |
| R8 | MULTIPLE | 20 KΩ |
| R9 | MULTIPLE | 2.2 MΩ |
| R10 | MULTIPLE | 180 KΩ |
| R11 | MULTIPLE | 1.0 MΩ |
| R12 | MULTIPLE | 10 KΩ |
| C1 | MULTIPLE | 22 μf |
| C2 | MULTIPLE | 22 μf |
| C3 | MULTIPLE | 0.1 μf |
| C4 | MULTIPLE | 20 pf |
| C5 | MULTIPLE | 20 pf |
| C6 | MULTIPLE | 0.01 μf |
| S1 | MULTIPLE | BOARD SWITCH |
| S2 | MULTIPLE | BOARD SWITCH |
| S3 | MULTIPLE | MECHANICAL REED SWITCH |
| J1 | MULTIPLE | SENSOR CONNECTION |
| J2 | MULTIPLE | BATTERY CONNECTION |
| J3 | MULTIPLE | AUDIO CONNECTION |
| AT1 | MULTIPLE | AUDIO TRANSDUCER |
| B1 | MULTIPLE | 3V LITHIUM BATTERY |
| LCD | MULTIPLE | DOT MATRIX DISPLAY |
| EC | MULTIPLE | ELASTOMERIC CONNECTORS |
| PCB | MULTIPLE | CIRCUIT BOARD |

Mechanical Layout

Figure 9:
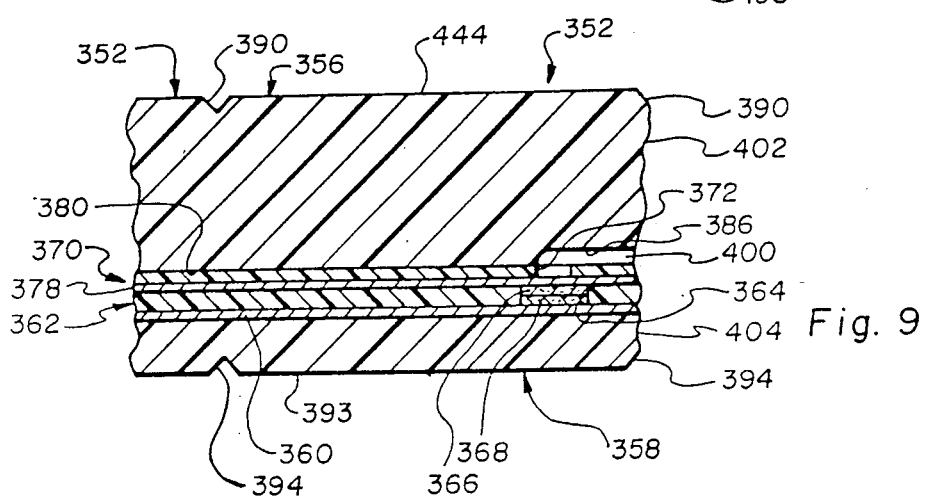
FIG. 9 is a cross-section taken along lines 9—9 of FIG. 5.

Referring to FIGS. 2 and 9, the electronics circuit board 332 is mounted at the approximate center of the instrument housing. The mechanical parts of the instrument 50 as well as the disposable sensor strip 350 are below the circuit board with the electronic components 336 being mounted on the upper side of the circuit board 332. The liquid crystal display 68 is preferably attached to the circuit board by conventional elastomeric connectors. The audio transducer 768 (piezo electric type) is bonded to the bottom side of the circuit board. Some of the electronic components 336 are preferably sandwiched between the circuit board 332 and the display 68. All semiconductors are preferably either in surface mount packages or in tab auto bonded dies. Chip resistor, chip capacitors and micro sized switches are preferably employed. The dot matrix Liquid Crystal Display 68, with 16 rows and 84 columns of pixels that are driven by display driver chips to form alphanumeric characters as well as graphics, including time, date and analyte test result bar graphs.

Software—Main Flow Chart

Figure 30:
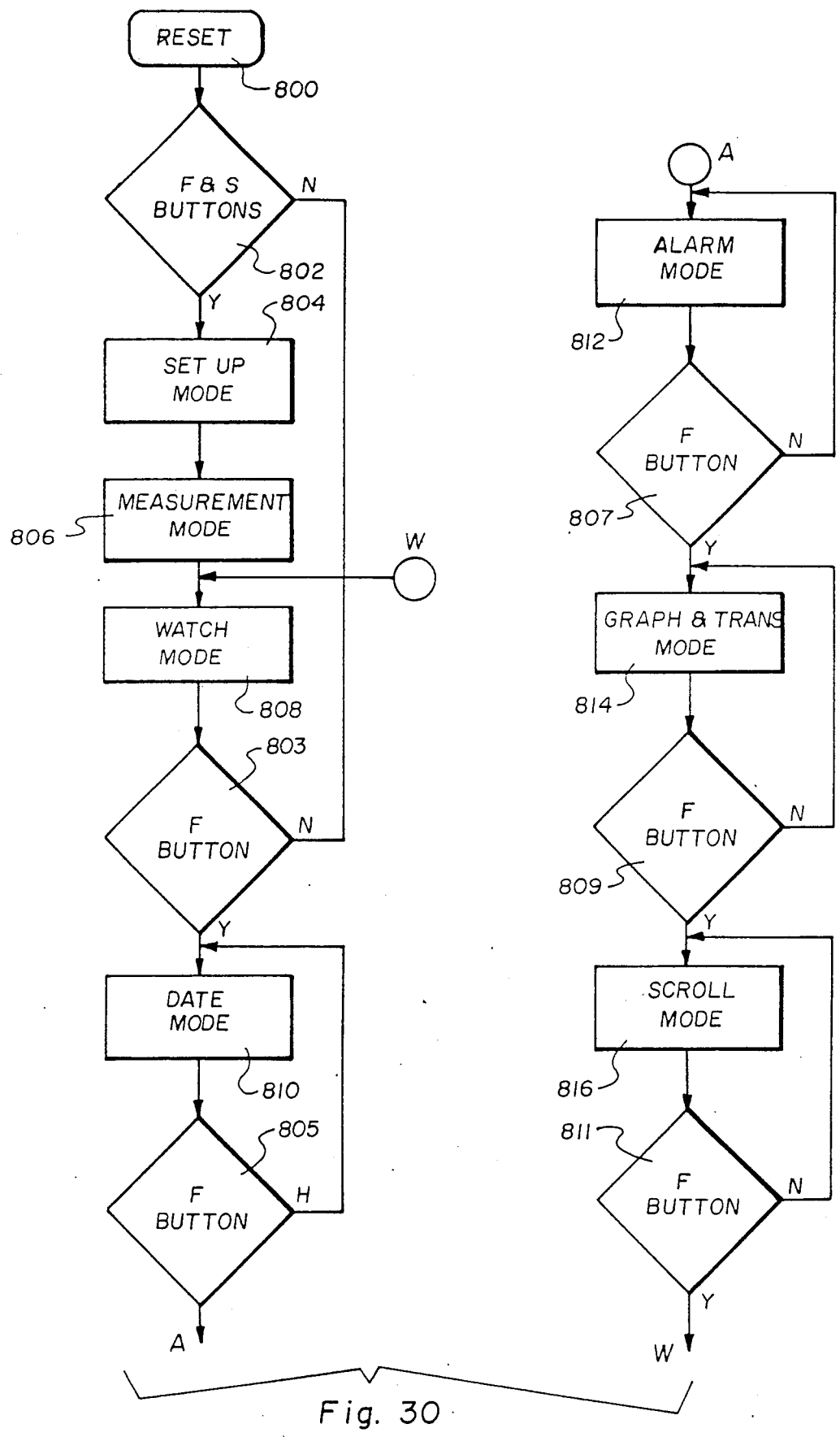
FIGS. 30–38, inclusive, are instrument software flow charts.

Main Software Flow Chart, shown in FIG. 30, illustrates the basic software for the instrument. In the presently preferred embodiment, there are three user actuators that determine the systems's mode of operation. The reset actuator is mechanically connected to the lancet firing button and is activated each time a lancet 384 is triggered by button 116 (FIG. 1). The function button F, aka button 118, allows the user to scroll through different functions of the device. The set button S, aka button 112, allows the user to change device attributes and set time and date.

A reset at 800 occurs when the system is first powered up and each time the lancet firing button 116 is pressed. If both F and S buttons, at 802, are pressed, the SET UP mode at 804 is entered. The SET UP mode at 804 will be used at the factory or other locations to customize each instrument as to the specific characteristics. These characteristics may include, but are not limited to: serial number, date of manufacture, type of analyte, 12 or 24 hour clock, United States or International displa format, units of concentration, look up tables, etc.

In the MEASUREMENT mode at 806, analog circuitry is turned on and approximately 30 seconds of data are taken. These data are then processed to determine the corresponding analyte concentration. The algorithm used depends upon the specific analyte being measured and can vary from a simple averaging technique to elaborate curve fitting. The resulting concentration value is then stored in memory and displayed in numerical form.

After the measurement is completed, stored and displayed, the system goes into the WATCH mode at 808. The WATCH mode at 808 is the normal wait mode of the system. In this mode, the time of day, in either 12 or 24 hour format, is displayed and the microcontroller 750 functions are minimized to conserve electrical power consumption. As described hereafter, the S button can be pressed while in this mode to set the time of day and to select 12 or 24 hour display format.

The system stays in WATCH mode at 808 until the F button at 803 takes the system into the DATE mode at 810, where the date is displayed. While in this mode, depressing the S button in this mode allows the user to set the day and month (no year display is presently preferred).

From the DATE mode at 810, the F button at 805 takes the system into the ALARM mode at 812. In this mode, the alarm time is displayed and can be changed and turned on or off using the S button. Independent of mode, the alarm, if turned on, will alert the user by an alarm time audio signal (beeps) at 973. The alarm signal continues until either a button is pressed or 30 seconds have expired.

From the ALARM mode at 812, the F button at 807 takes the system into the GRAPH mode at 814. In this mode, the results of up to preferably 21 days of measurements are displayed graphically, preferably in a bar format. Different display formats can be selected by using the S button.

While in the GRAPH mode, pushing of the F button at 809 takes the system into the SCROLL mode at 816. This mode allows the user to scroll through previous assay values and date and time acquired.

From the SCROLL mode at 816, pressing the F button at 811 returns the system to the WATCH mode at 808. If the system is left without user inputs for a period of 5 minutes (no button actuation) the system automatically returns to the WATCH mode at 808.

In the GRAPH mode at 814, if the F button is pressed and held for 5 seconds, the TRANSMIT mode at 814 is entered. In this mode, the stored data can be serially transmitted over a standard telephone or the like by way of the audio transducer 768. A 300 baud, Bell Telephone standard format is utilized so that commercially available modems and common computers can be used to receive the data.

Software—Set Up Mode

Figure 31:
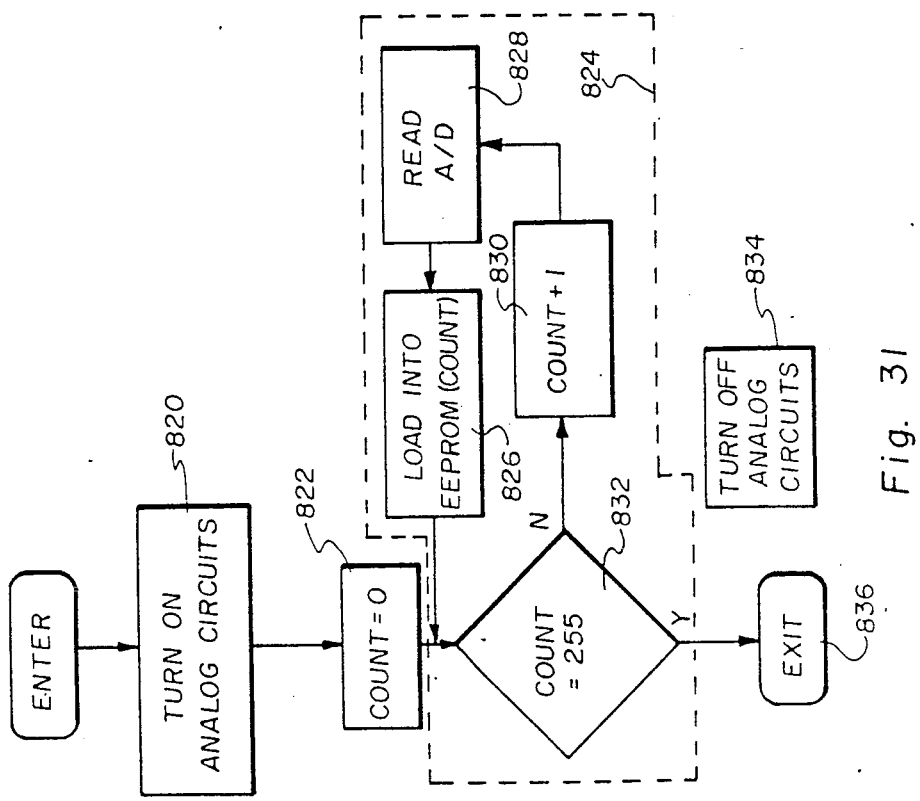

Referring to FIG. 31, when entering the SET UP mode at 804 in FIG. 30, the analog circuits, which include amplifiers, voltage references, and A/D 758, are turned on at 820 and counter (COUNT) at 822 is set to zero. COUNT at 822 is used as a loop counter for loop at 824 and is tested to allow 256 samples of sensor data to be taken by the A/D at approximately 0.1 second intervals. During this loop, until COUNT 822 is greater than 255, COUNT is incremented at 830, an A/D 758 reading is made at 828 and stored in electrically erasable programmable read only memory at 826. When COUNT is greater than 255 (at 832), the analog circuits are turned off at 834, and the program exits at 836 to the main routine FIG. 30.

Software—Measurement Mode

Figure 32:
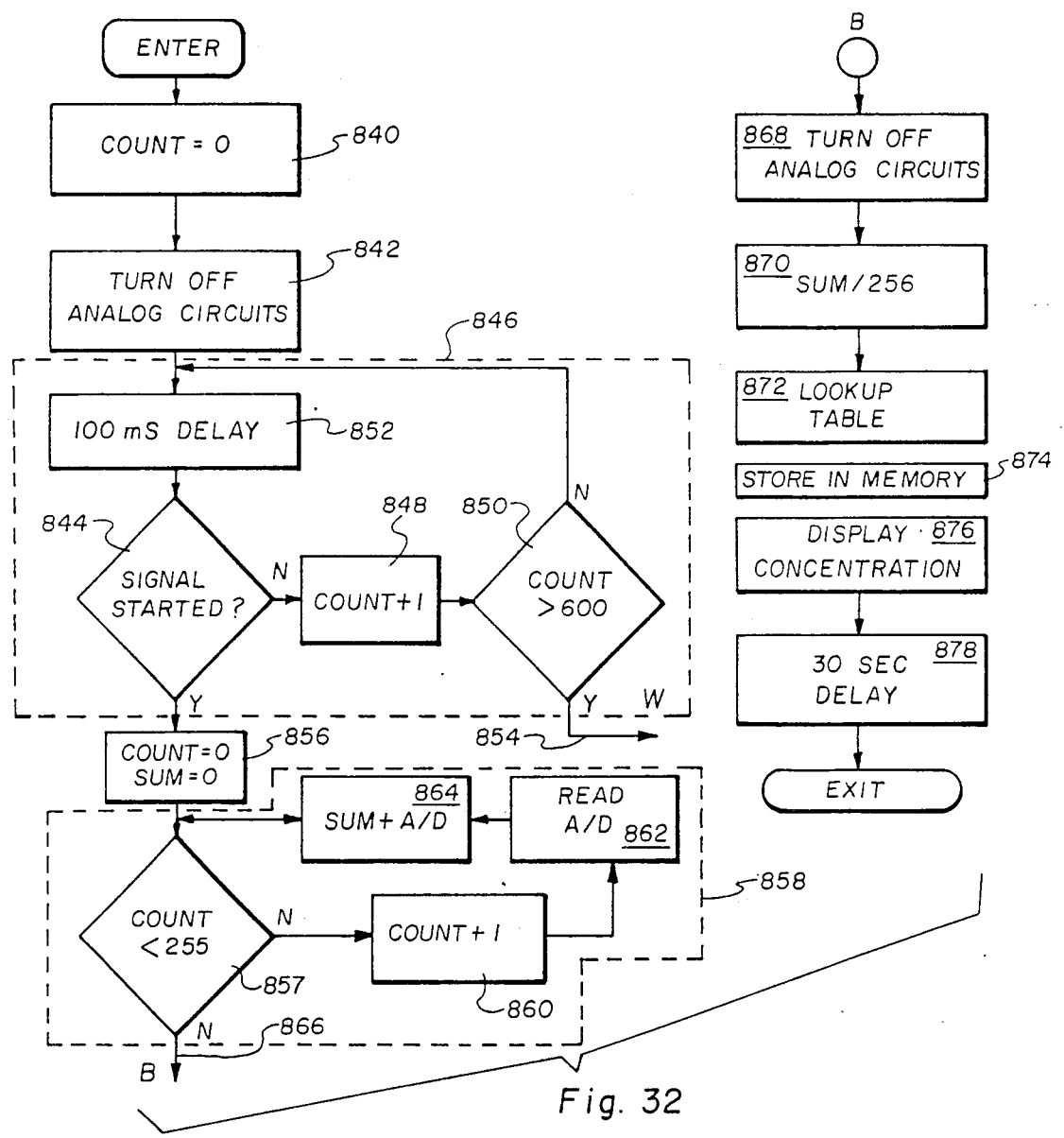

Referring to FIG. 32, upon entering the MEASUREMENT mode at 806 in FIG. 30, COUNT at 840 is set to zero, the analog circuits, which include amplifiers, voltage references and A/D, are turned on at 842. COUNT at 840 is used as a loop counter and is tested to allow a maximum of 600 no signal iterations at 844 of loop 846. Each iteration determines if there is signal coming from the liquid detector or the sensor, increments COUNT at 848, determines if COUNT is greater than 600 at 850, and delays 100 milliseconds at 852. In the event that COUNT is greater than 600 at 850, which indicates over 60 seconds has expired since lancet firing with no signal resulting from the sensor, the program exits to WATCH mode at 854.

In the event that a sensor signal is recognized at 844, COUNT and SUM at 856 are set to zero. When the COUNT at 857 is less than 255, loop at 858 comprises a loop counter. During the loop, COUNT is incremented at 860, a sensor reading is made by the A/D at 862, the reading is added to SUM at 864, which becomes a running total of sensor readings, the COUNT is tested at 857 to be less than 255. After 256 iteration of loop 858, SUM at 864 contains the SUM of 256 sensor reads over approximately a 26 second period.

Upon exiting loop 858 at 866, the analog circuits are turned off at 868 and SUM is divided by 256 at 870 to form a simple mean of the sensor readings acquired. The corresponding concentration is found in look-up table at 872 or by use of logit fit routine. The concentration value is stored in memory at 874 and displayed at 876 for 60 seconds at 878 before exiting at 880 to the main program (FIG. 30).

Software—Watch Mode

Figure 33:
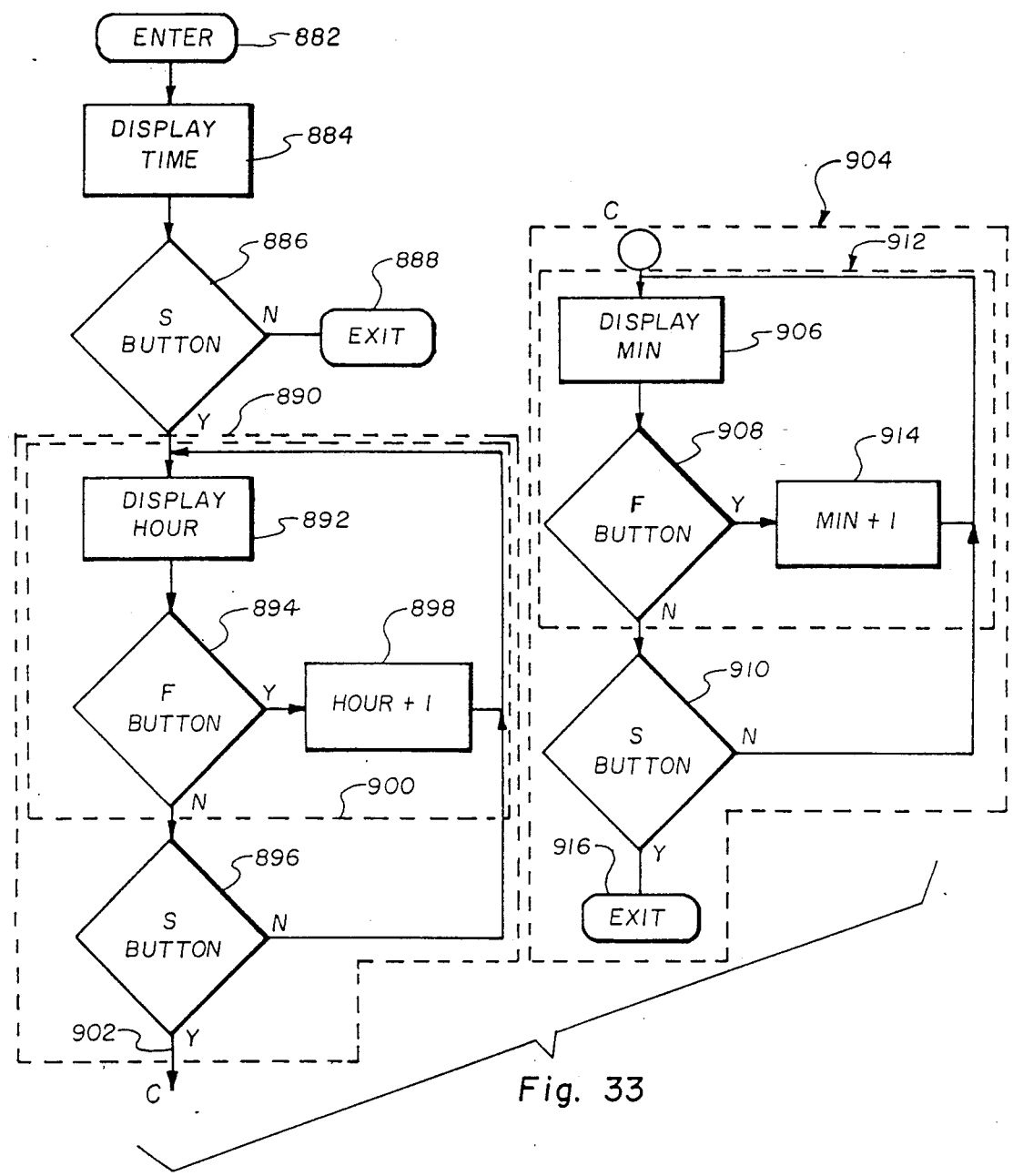

The WATCH mode (FIG. 33) is the low current mode of the electrical system. When the system is idle it reverts to this mode. When entering this mode at 882, the time of day is displayed at 884 and the S button at 886 is tested to determine if it is depressed. In the event the S button is not depressed, the program exits at 888 to the main routine. In the event the S button is depressed, the loop at 890 is entered. This loop is the HOUR setting loop which continuously displays the hour of the day at 892 and tests buttons F at 894 and S at 896. In the event the F button is actuated, HOUR is incremented at 898 through a subloop at 900. An S button actuation at 896 creates an exit of loop at 902 and an entrance to loop at 904. Loop 904 is the minute (MIN) setting loop. In this loop, MIN is displayed at 906 and F and S buttons, at 908 and 910, respectively, are monitored. When actuation of the F button occurs at 908, subloop at 912 is followed, incrementing MIN at 914. A depressing of button S at 910 will exit the time setting mode at 916 and will return to the main routine.

Software—Date Mode

Figure 34:
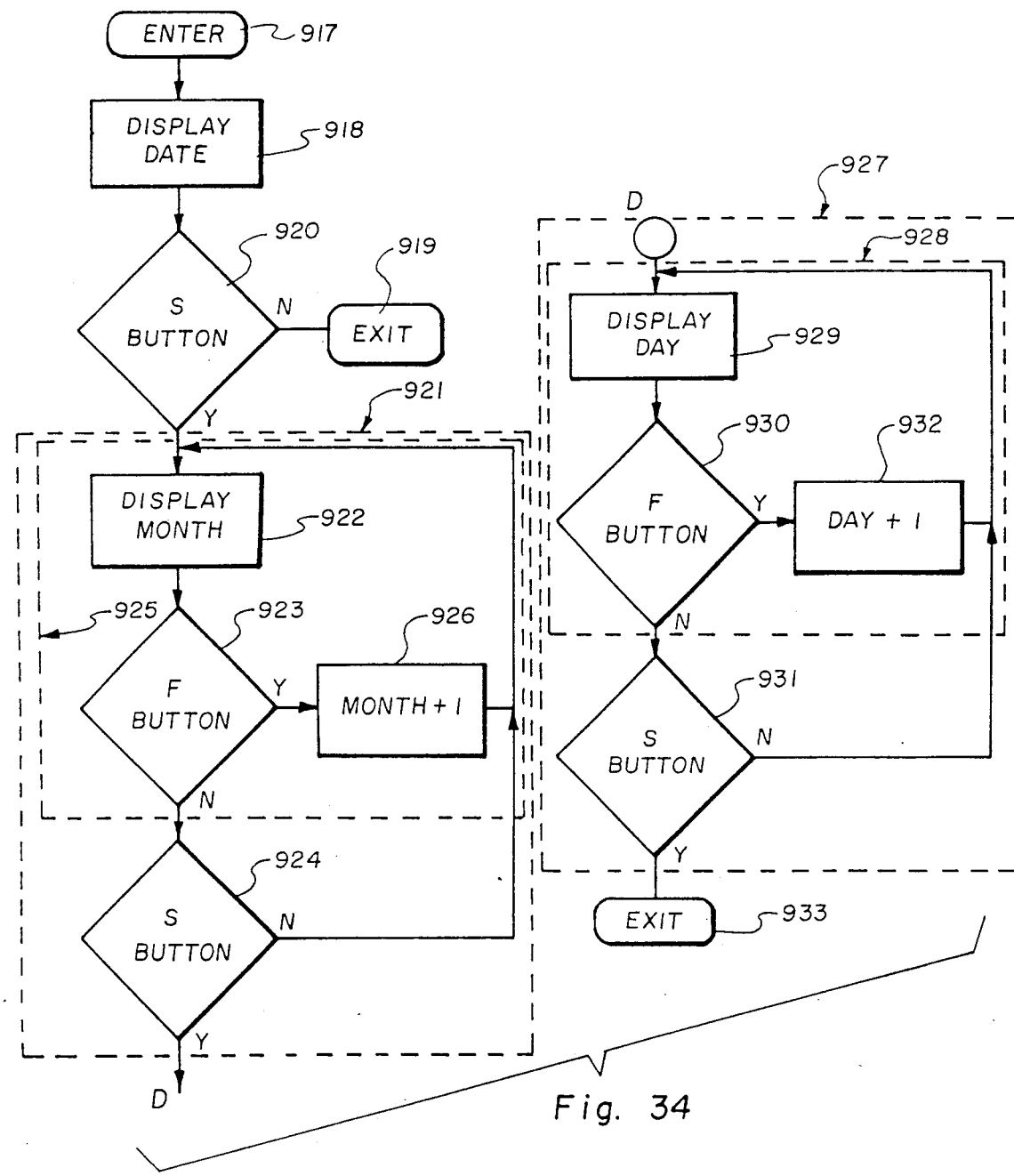

The DATE mode (FIG. 34) is entered at 917 from the main routine. This mode displays the month and day of the month at 918 and exits to the main routine at 919 unless button S is depressed at 920. On event S (when the S button is actuated), the MONTH setting loop at 921 is entered. This loop displays MONTH at 922 and monitors the user buttons F and S at 923 and 924, respectively. If depression of the F button occurs, MONTH is incremented at 926, using subloop 925. When the S button is depressed, there is an exit from loop 921 and an entrance to the DAY-OF-THE-MONTH setting loop 927. Loop 927 displays the DAY-OF-THE-MONTH at 929 and monitors the F and S buttons at 930 and 931. Subloop 928 is branched so that when actuation of the F button occurs at 930, DAY at 932 is incremented. When the S button is actuated at 931, loop 927 is broken and the program exits at 933 to the main routine.

Software—Alarm Mode

Figure 35:
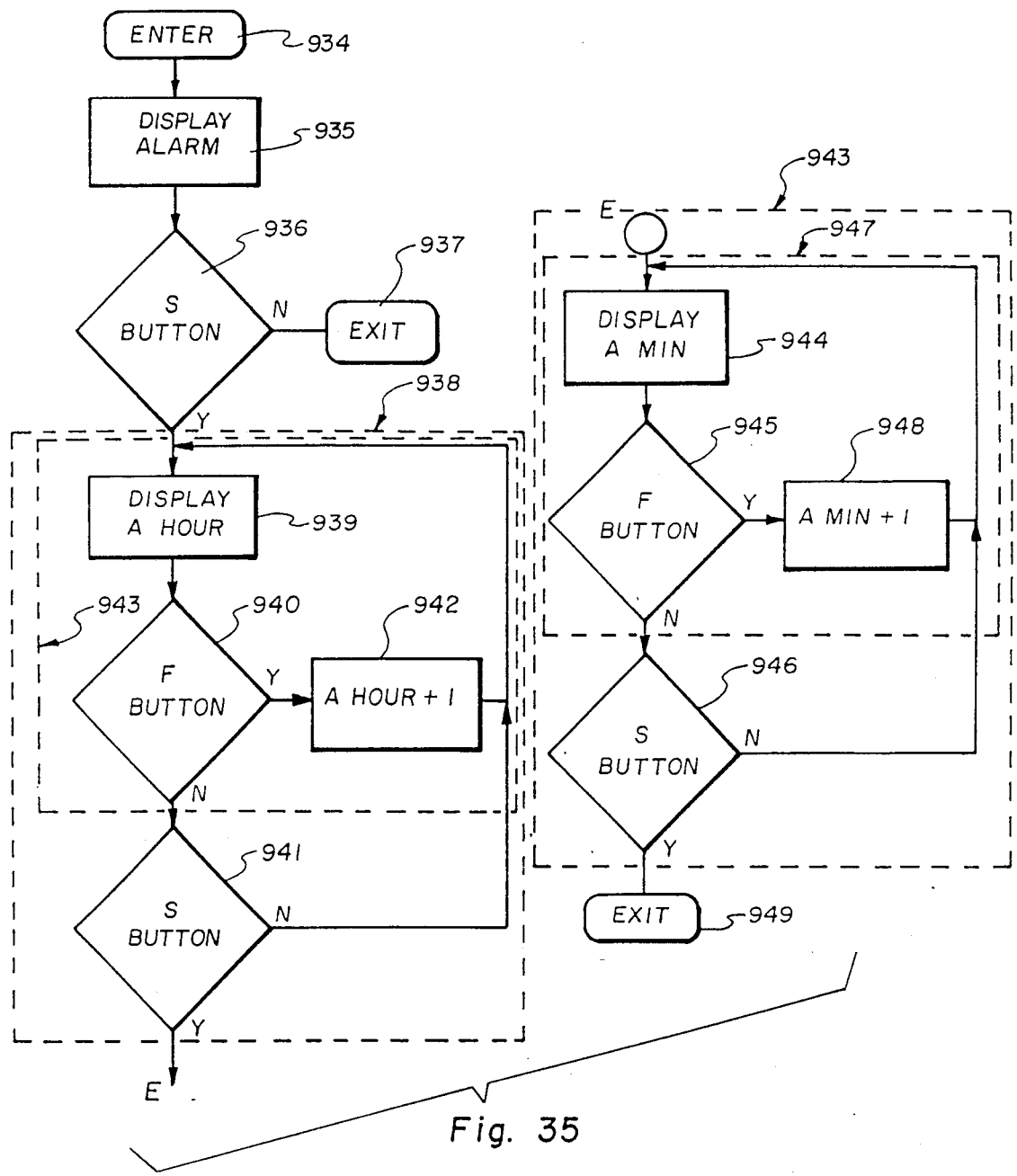

FIG. 35 depicts the ALARM mode software of the system. When entering ALARM mode at 934, the time of ALARM is displayed at 935 and the S button is tested at 936 to determine if it is depressed. In the event the S button is not depressed, the program exits to the main routine at 937. In the event the S button is depressed, loop 938 is entered. This loop is the alarm-hour (AHOUR) setting loop, which continuously displays at 939 the hour of the ALARM and tests buttons F and S at 940 and 941, respectively. In the event the F button is depressed, AHOUR is incremented at 942 through subloop 943. An S button activation at 941 creates an exit of loop 938 and an entrance to loop 943'. Loop 943' is the alarm minute setting loop. In this loop, alarm minute (AMIN) is displayed at 944 and the F and S buttons are monitored at 945 and 946, respectively. If event depression of the F button occurs at 945, subloop 947 is followed, incrementing AMIN at 948. A depression of button S at 946 will exit the time setting mode at 949 and will return to the main routine.

Software—Graph and Transmit Mode

Figure 36:
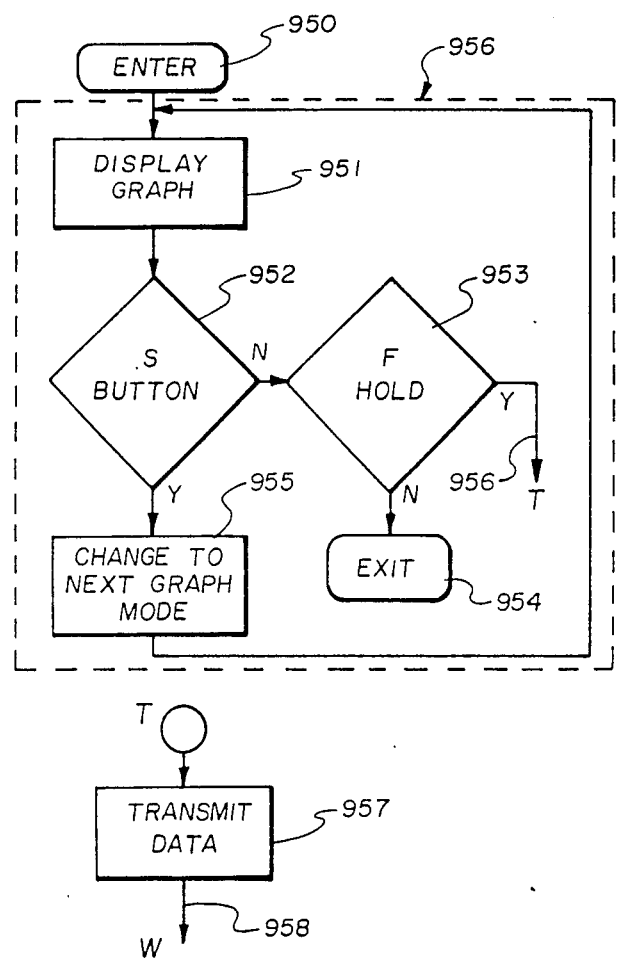

Referring to FIG. 36, upon entering the GRAPH mode at 950, stored assay values are displayed at 951 in one of the available graphical forms. If neither the S nor F button is pressed at 952 and 953, respectively, the program exits at 954 to the main routine. Depression of the S button at 952 will result in the selection of a new graphical display format at 955 and will instigate a loop back at 956 to the beginning of the routine. If the F button at 953 is held down for 5 seconds, the TRANSMIT mode is entered at 956. This mode TRANSMITS at 957 previously stored assay data via 300 baud Bell Telephone standard format. After transmission of data at 957, the program exits at 958 to the WATCH mode routine.

Software—Scroll Mode

Figure 37:
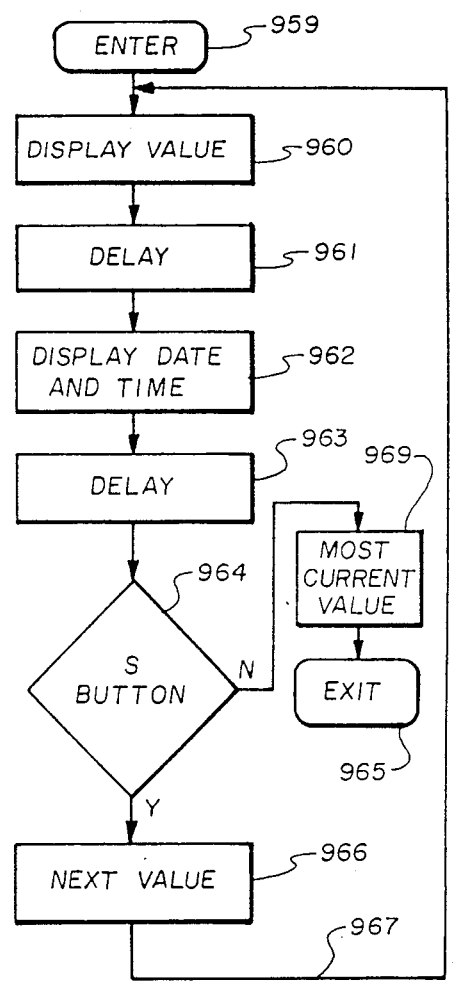

The SCROLL mode (FIG. 37) allows the user to display individual assay results along with the associated date and time of acquisition. Upon entering this mode at 959, the most recently acquired assay value is displayed at 960. After an appropriate delay at 961, the date and time of acquisition are displayed at 962. After another delay at 963, if no depression of the S button has occurred at 964, the program exits at 965 to the main routine. If the S button is depressed at 964, the previously acquired assay value and its associated date and time of acquisition are loaded at 966 for display. The program then loops at 967 to the beginning of the routine to repeat the procedure, displaying acquired assay value with its date and time. This process repeats until the earliest stored value has been shown when the next value displayed is again the most recent value 969.

Software—Real Time Clock

Figure 38:
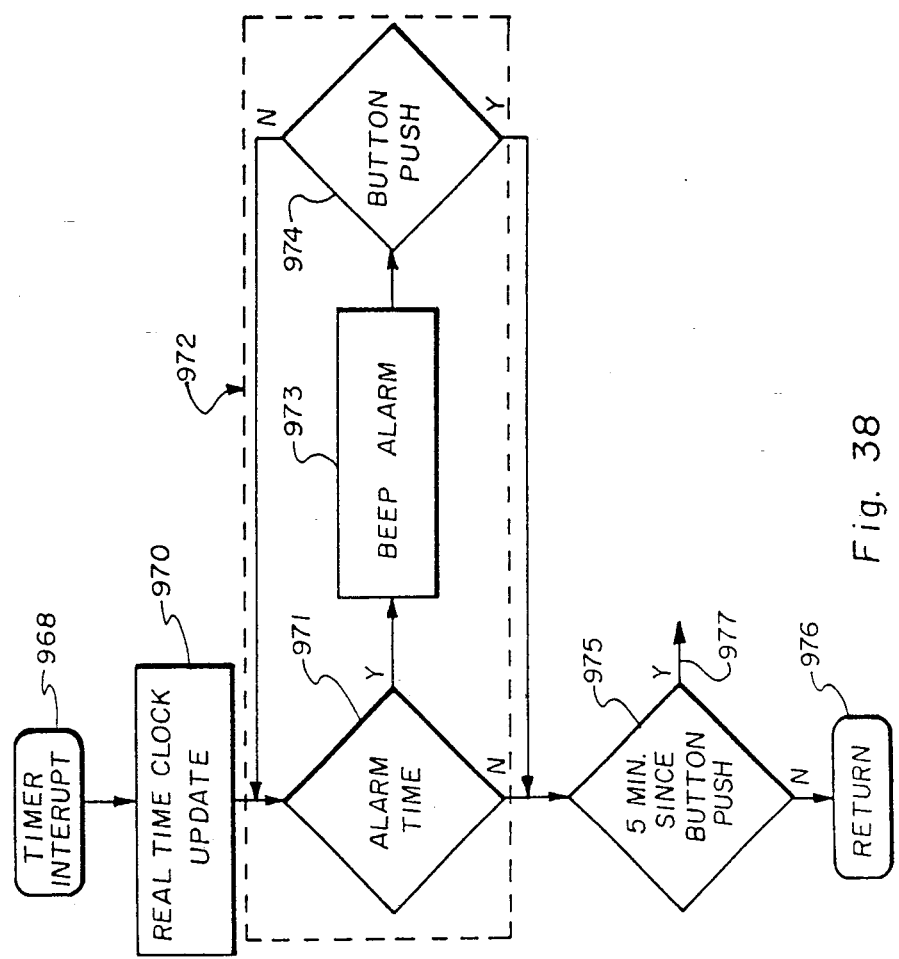

The REAL TIME CLOCK (FIG. 38) of the system runs asynchronously to all other program routines. The Motorola MC68HC05 microcontroller 750 provides a 16 bit presetable counter which issues an interrupt when its value equals zero. Upon receipt of this interrupt at 968, the CLOCK registers for seconds, minutes, hours, days and months are updated at 970. The appropriate value is also loaded into TIMER INTERRUPT register to facilitate the next timer interrupt. Alarm values of AHOUR and AMIN are compared with HOUR and MIN, respectively, to determine at 971 if the alarm time has been reached. When the alarm time matches the present clock time, an audible beep at 973 is created. Loop 972 continues to sound the alarm at 973 until either the present clock value changes to the next minute at 971 or until a user button is depressed at 974. If the alarm time is not matched at 971 or after the alarm has completed its function, a test for user inactivity is made at 975. In the event of button actuation during the previous five minutes, the program returns at 976 to the interrupted routine. If a five minute or more time of user inactivity is determined, the program exits at 977 to the WATCH mode for power conservation.

Preferred Electronic Operation During An Assay

Before starting an assay, the normal operational mode for the electronics will be the WATCH mode 808, as described here in the Software sections. In this mode, the sensor 760, amplifier section 762, voltage reference generated in 764B, and A/D 758 of the circuit 336 are turned off to conserve battery life. The microcontroller 750 is put into a "wait" mode, as described by Motorola literature for the MC68HC05 microcontroller 750. In this mode, the microcontroller 750 runs at a reduced clock speed, thus conserving even more power.

The user advances the packet 350 of sensors 352 and removes the insert tab 354 or the previously used sensor 352. See FIG. 5. When the user presses the lancet triggering button 116, the magnet 301 mounted on the side of button 116 moves with button 116 away from the proximity of normally-closed magnetic reed switch S3. The resulting closure of S3 drops the voltage on reset pin RT of microcontroller MC 750. As per the software flow chart of FIG. 30, the circuitry 336 enters either the SET UP mode 804, if both button switches S1 and S2 are pressed, or into the MEASUREMENT mode if not. In the SET UP mode 804, digital information present at the sensor connector J1 (FIG. 28) will be down-loaded into microcontroller memory. This mode is used at the factory or other locations to customize the characteristics of each instrument. These characteristics may include, but are not limited to, serial number, date of manufacture, type of analyte, 12 or 24 hour clock, United States or International display format, units of concentration, look-up tables, etc.

In the MEASUREMENT mode 806, the sensor 760, amplifier 762, voltage references generated by 764B, and the A/D 758 of MC 750 are activated. The circuit 336 also applies 3 VDC to sensor electrode L and 0.2 VDC to electrode S. The large electrode M is connected to circuit ground and thus is at 0.0 VDC at all times. Before blood or other liquid enters the sensor 760, there will not be significant current flow between the electrodes. After lancing the finger, the user places the capillary opening 386 of the sensor 352 into the resulting droplet of blood. By capillary action, blood is drawn into the sensor 352 filling the void between and electrically connecting electrodes L and S. The liquid sample thus acts as a conductor bridge between electrode L, which is at 3 VDC, and electrode S, which at 0.2 VDC. The resulting current flow is amplified by amplifier OP1 and associated circuitry and sensed as a voltage change by the A/D 758 at pin N1 of MC 750. This signals the microcontroller 750 that sufficient liquid sample has entered the sensor to begin an assay. The 3 VDC on electrode L is then turned off and the current flow between electrodes S and M is amplified by OP1 and measured by the A/D 758 via pin N1. In the presently preferred embodiment, 256 measurements are taken over approximately 26 seconds. See FIGS. 24 and 25 for typical waveforms, 60 seconds in duration. The simple mean of these values are then converted to a concentration value by the software, either a look-up table or a logit fit routine. The sensor, amplifier, voltage references, and A/D are then turned off and the concentration of analyte displayed. After a given time, the circuit then goes into the WATCH mode 808 where time of day is displayed.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. Multiple lancet structure comprising:
   instrument means;
   packet means associated with the instrument means and comprising a plurality of closely associated individually usable and disposable finger piercing elements for respective sequential acquisition of blood droplets, biasing means associated with each finger piercing element by which the associated finger piercing element when in a ready to use position in the instrument means is displaced to penetrate a fingertip or other patient site and thereafter retracted.

2. Multiple lancet structure according to claim 1 wherein the biasing means comprise a single element.

3. Multiple lancet structure according to claim 1 wherein the packet means comprises means encapsulating each associated finger piercing means and biasing means and frangible linkage means serially joining together the encapsulating means.

4. Multiple lancet structure according to claim 3 wherein tab means are disposed at the distal end of at least one encapsulating means.

5. Multiple lancet structure according to claim 1 further comprising connector means by which the packet means are accurately matched to and aligned with the instrument means.

6. Multiple lancet structures according to claim 1 wherein the packet means comprise housing means encapsulating each associated finger piercing element and biasing means, in substantially concealed relation, each housing means comprising port means by which the encapsulated finger piercing element is displaced and retracted.

7. Multiple lancet structure according to claim 1 wherein each biasing means are disposed within the packet means in a cocked condition counter to memory of each biasing means.

8. Multiple lancet structure comprising:
   disposable encapsulating means;
   a plurality of individually usable and disposable finger piercing elements each carried within the encapsulating means for respective sequential acquisition of blood droplets;
   a plurality of biasing means one associated with each finger piercing element within the encapsulating means by which the associated finger piercing element is selectively actuated to leave the encapsulating means and penetrate a fingertip or other patient site and thereafter retract under reverse force of the associated biasing means into the encapsulating means.

9. Multiple lancet structure according to claim 8 wherein the biasing means comprise a single biasing element.

10. Multiple lancet structure according to claim 8 further comprising instrument means into which the encapsulating means with finger piercing means and biasing contained therein are inserted.

11. Multiple lancet structure according to claim 10 wherein the encapsulating means further comprise detent means by which the encapsulating means are held in a selected position in respect to the instrument, the detent means accommodating indexing of the encapsulating means in respect to the instrument.

12. Multiple lancet structure according to claim 11 wherein the detent means comprise spaced notches in the encapsulating means.

13. Multiple lancet structure according to claim 8 wherein the encapsulating means comprise frangible segments each containing one finger piercing means with its associated biasing means.

14. Multiple lancet structure according to claim 13 wherein manual separation of one frangible segment from another exposes pathway means in the encapsulating means for selective reciprocation of finger piercing means.

15. Multiple lancet structure according to claim 8 wherein each biasing means are disposed within the encapsulating means in a cocked condition counter to memory of each biasing means.

16. Multiple lancet structure according to claim 8 further comprising actuator means carried by the encapsulating means adjacent each biasing means for selectively causing the biasing means to displace the associated finger piercing means.

17. A method of accommodating the provision of sequential droplet samples of blood comprising the steps of:

placing a packet of individual encapsulated separately biased finger piercing elements in a receptacle of an instrument;

securing the packet in a releasably restrained condition within the receptacle so that one end of the packet is exposed at the distal end of the instrument;

uncovering egress/ingress pathway means to one finger piercing element at the distal end of the sensor encapsulating packet;

selectively actuating the distal finger piercing element by releasing said bias whereby said distal finger piercing element is reciprocated along the egress/ingress pathway means to penetrate a fingertip or the like of a medical patient and thereafter to retract the distal finger piercing means into the encapsulation;

indexing the packet distally against said restraint until the distal encapsulated finger piercing element and at least part of the next encapsulating finger piercing element is exposed beyond the distal end of the instrument;

manually breaking the packet between the two exposed piercing elements to uncover the egress/ingress pathway means to the next enclosed encapsulated piercing element.

18. A method according to claim 17 wherein the recited steps are repeated until the supply of the encapsulated piercing elements of the packet are exhausted.

* * * * *

UNITED STATES PATENT AND TRADEMARK OFFICE
CERTIFICATE OF CORRECTION

PATENT NO.   :   5,047,044
DATED        :   September 10, 1991
INVENTOR(S)  :   ROGER E. SMITH It is certified that error appears in the above-identified patent and that said Letters Patent is hereby corrected as shown below:

On Title Page, Item 75, Inventors: ROGER E. SMITH, Bountiful, Utah.

Delete "Mark E. Astill, Centerville; Jay L. Smith, Ogden; Gale H. Thorne, Bountiful, all of Utah.

Signed and Sealed this

Twenty-eighth Day of January, 1992

Attest:

HARRY F. MANBECK, JR.

*Attesting Officer*  *Commissioner of Patents and Trademarks*